United States Patent
Li et al.

(10) Patent No.: US 9,833,520 B2
(45) Date of Patent: Dec. 5, 2017

(54) LABELED, NON-PEPTIDIC, MULTIVALENT INTEGRIN ANTAGONIST COMPOUNDS; METHODS FOR SYNTHESIS AND USES THEREOF

(71) Applicant: The Methodist Hospital Research Institute, Houston, TX (US)

(72) Inventors: King Chuen Li, Houston, TX (US); Zheng Li, Houston, TX (US); Feng Li, Houston, TX (US)

(73) Assignee: The Methodist Hospital Research Institute, Houston, TX (US)

( * ) Notice: Subject to any disclaimer, the term of this patent is extended or adjusted under 35 U.S.C. 154(b) by 64 days.

(21) Appl. No.: 13/952,576

(22) Filed: Jul. 26, 2013

(65) Prior Publication Data
US 2014/0044646 A1 Feb. 13, 2014

Related U.S. Application Data

(63) Continuation of application No. PCT/US2012/022712, filed on Jan. 26, 2012.

(60) Provisional application No. 61/436,527, filed on Jan. 26, 2011.

(51) Int. Cl.
| | |
|---|---|
| A61K 51/00 | (2006.01) |
| A61M 36/14 | (2006.01) |
| A61K 49/00 | (2006.01) |
| A61K 47/48 | (2006.01) |
| A61K 51/04 | (2006.01) |
| A61K 45/06 | (2006.01) |
| C07D 403/14 | (2006.01) |
| C07D 239/14 | (2006.01) |
| A61K 9/127 | (2006.01) |
| A61K 9/51 | (2006.01) |
| A61K 31/505 | (2006.01) |
| A61K 31/506 | (2006.01) |
| A61K 47/60 | (2017.01) |
| A61K 47/55 | (2017.01) |

(52) U.S. Cl.
CPC .......... *A61K 49/0021* (2013.01); *A61K 9/127* (2013.01); *A61K 9/51* (2013.01); *A61K 31/505* (2013.01); *A61K 31/506* (2013.01); *A61K 45/06* (2013.01); *A61K 47/481* (2013.01); *A61K 47/48215* (2013.01); *A61K 47/55* (2017.08); *A61K 47/60* (2017.08); *A61K 49/0052* (2013.01); *A61K 51/0459* (2013.01); *C07D 239/14* (2013.01); *C07D 403/14* (2013.01)

(58) Field of Classification Search
CPC .... A61K 49/00; A61K 49/0052; A61K 45/06; A61K 47/481; A61K 47/48215; A61K 51/00; A61K 51/0459; A61K 9/00; A61K 9/127; A61K 49/0021; A61K 9/51; A61K 31/00; A61K 31/505; A61K 31/506; C07D 403/14; C07D 239/14
USPC .......... 424/1.11, 1.49, 1.65, 1.69, 1.73, 1.81, 424/1.85, 1.89, 9.1, 9.2, 9.3, 9.4, 9.5, 9.6, 424/9.7; 514/1, 1.1, 19.2, 19.3, 19.4, 514/19.5, 19.6
See application file for complete search history.

(56) References Cited

U.S. PATENT DOCUMENTS

| | | | |
|---|---|---|---|
| 6,102,884 A | 8/2000 | Squitieri | |
| 7,255,682 B1 | 8/2007 | Bartol, Jr. et al. | |
| 7,563,433 B2* | 7/2009 | McBride et al. | ............ 424/1.89 |
| 7,829,064 B2* | 11/2010 | Griffiths et al. | ............ 424/1.21 |
| 2004/0010304 A1 | 1/2004 | Weber et al. | |
| 2006/0064159 A1 | 3/2006 | Porter et al. | |
| 2011/0223102 A1* | 9/2011 | Pandey | ............ A61B 5/02007 424/1.11 |

FOREIGN PATENT DOCUMENTS

WO   WO 97/23451   7/1997

OTHER PUBLICATIONS

Jang et al, Nuclear Medicine and Biology, 2007, vol. 34, pp. 363-370.*
Li et al, Bioorganic & Medicinal Chemistry Letters, Sep. 2010, vol. 20, pp. 6577-6580.*
Li et al, Bioconjugate Chemistry, 2010, vol. 21, pp. 270-278.*
Allison, RC et al., "Thermodilution measurement of lung water," Clin. Chest Med., 6(3):439-457 (Sep. 6, 1985).
Arap, Wadih et al., "Cancer treatment by targeted drug delivery to tumor vasculature in a mouse model," *Science*, 279(5349):377-380 (Jan. 16, 1998).
Bernard, B et al., "Radiolabeled RGD-DTPA-Tyr3-octreotate for receptor-targeted radionuclide therapy," Cancer Biother. Radiopharm., 19(2):173-80 (Apr. 2004).
Boerman, O.C., "A Dota-Conjugated peptidomimetica, $\alpha_v \beta_3$ integrin-binging agent for targeting tumors," Proceedings of the SND 50th Annual Meeting, Scientific Papers, 44(5): BNSDOCID:<XP 8105408A, 1 page, (May 2003).

(Continued)

*Primary Examiner* — D L Jones
(74) *Attorney, Agent, or Firm* — Haynes and Boone, LLP

(57) ABSTRACT

Disclosed are multivalent, integrin-receptor antagonists that are useful in a variety of therapeutic, prophylactic, and/or diagnostic imaging modalities. In illustrative embodiments, such compounds have been prepared and utilized in the imaging, detection, localization, and/or quantitation of one or more samples of biological interest. Similarly, these compounds, as well as formulations comprising them, find utility in the prevention, treatment, and/or amelioration of one or more symptoms of a disease, abnormal condition, dysfunction, etc., including, for example proliferative diseases such as cancer in affected animals. In certain embodiments, fluorescently- or radio-labeled-non-peptidic, multivalent integrin $\alpha_v \beta_3$ compounds are provided. Compositions including such compounds have been shown to have utility in detecting, localizing, quantitating, and/or imaging integrin $\alpha_v \beta_3$ receptor-expressing cells, including, for example, cancer cells in vitro, in vivo, and/or in situ.

9 Claims, 27 Drawing Sheets

(56) References Cited

OTHER PUBLICATIONS

Bradbrook, M et al., "X-ray and molecular dynamics studies of concanavalin-A glucoside and mannoside complexes; relating structure to thermodynamics of binding," J. Chem. Soc., Faraday Transact., 94(11):1603-1611 (1998).
Brooks, PC et al., "Requirement of vascular integrin αvβ3 for angiogenesis," Science, 264(5158):569-571 (Apr. 22, 1994).
Broxterman, HJ et al., "Resistance to cytotoxic and anti-angiogenic anticancer agents: similarities and differences," Drug Resist. Updat., 6(3):111-127 (2003).
Burnett, Christopher A. et al., "Synthesis, in vitro, and in vivo characterization of an integrin $β_vβ_3$-targeted molecular probe for optical imaging of tumor," Bioorg. Med. Chem., 13(11):3763-3771 (Jun. 2005).
Capello, Astrid et al., "Increased cell death after therapy with an Arg-Gly-Asp-linked somatostatin analog," J. Nucl. Med., 45(10): 1716-1720 (Oct. 1, 2004).
Carlson, Coby B. et al., "Selective Tumor Cell Targeting Using Low-Affinity, Multivalent Interactions," ACS Chem. Biol., 2(2):119-127 (Feb. 9, 2007).
Case, David A. et al., "AMBER 11," University of California, San Francisco (2010), 302 pages.
Chen, Xiaoyuan, "Integrin targeted imaging and therapy," Theranostics, 1:28-29 (Jan. 12, 2011).
Chen, Kai and Chen, Xiaoyuan, "Integrin targeted delivery of chemotherapeutics," Theranostics, 1:189-200 (Feb. 17, 2011).
Chen, Xiaoyuan et al., "In vivo near-infrared fluorescence imaging of integrin $α_vβ_3$ in brain tumor xenografts," Cancer Res., 64:8009-8014 (Nov. 1, 2004).
Chen, X et al., "MicroPET and autoradiographic imaging of breast cancer αv-integrin expression using 18F- and 64Cu-labeled RGD peptide," Bioconjug. Chem., 15(1):41-49 (Dec. 30, 2003).
Chen, Xiaoyuan et al., "Pegylated Arg-Gly-Asp peptide: $^{64}$Cu labeling and PET imaging of brain tumor $α_vβ_3$-integrin expression," J. Nucl. Med., 45(10):1776-1783 (Oct. 2004).
Chen, X et al., "Pharmacokinetics and tumor retention of 125I-labeled RGD peptide are improved by PEGylation," Nucl. Med. Biol., 31(1):11-19 (2004).
Chen, X et al., "MicroPET imaging of breast cancer αv-integrin expression with $^{64}$Cu-labeled dimeric RGD peptide," Mol. Imaging Biol., 6(5):350-359 (2004).
Cheng, Zhen et al., "Near-infrared fluorescent deoxyglucose analog for tumor optical imaging in cell culture and living mice," Bioconjug. Chem., 17(3):662-669 (Apr. 21, 2006).
Cheng, Zhen et al., "Near-infrared fluorescent RGD peptides for optical imaging of integrin $α_vβ_3$ expression in living mice," Bioconjug. Chem., 16(6):1433-1441 (Oct. 29, 2005).
Cieplak, Piotr et al., "Application of the multimolecule and multiconformational RESP methodology to biopolymers: Charge derivation for DNA, RNA, and proteins," J. Comput. Chem., 16(11):1357-1377 (Nov. 1995).
Conforti, G et al., "Human endothelial cells express integrin receptors on the luminal aspect of their membrane," Blood, 80(2):437-46 (1992).
Darden, Tom et al., "Particle Mesh Ewald—an N•log(N) method for Ewald sums in large systems," J. Chem. Phys., 98(12):10089-10092 (Jun. 15, 1993).
Dayam, Raveendra et al., "Discovery of Small Molecule Integrin $α_vβ_3$ Antagonists as Novel Anticancer Agents," J. Med Chem., 49(15): 4526-4534 (Jul. 1, 2006).
Delbaldo, C et al., "Phase I and pharmacokinetic study of etaracizumab (Abegrin), a humanized monoclonal antibody against αvβ3 integrin receptor, in patients with advanced solid tumors," Invest. New Drugs, 26:35-43 (2008).
Denardo, SJ et al., "Neovascular targeting with cyclic RGD peptide (cRGDf-ACHA) to enhance delivery of radioimmunotherapy," Cancer Biother. Radiopharm., 15(1):71-79 (2000).
Duan, Y et al., "A point-charge force field for molecular mechanics simulations of proteins based on condensed-phase quantum mechanical calculations," J. Comput. Chem., 24(16):1999-2012 (2003).
Dupradeau, Francois-Yves et al., "The R.E.D. tools: advances in RESP and ESP charge derivation and force field library building," Phys. Chem. Chemical Phys., 12(28):7821-7839 (Jul. 2010).
Folkman, J, "Angiogenesis in cancer, vascular, rheumatoid and other disease," Nat. Med., 1:27-31 (1995).
Garanger, E et al., "Tumor targeting with RGD peptide ligands-design of new molecular conjugates for imaging and therapy of cancers," Anticancer Agents Med. Chem., 7(5):552-8 (2007).
Gestwicki, JE et al., "Influencing receptor-ligand binding mechanisms with multivalent ligand architecture," J. Am. Chem. Soc., 124:14922-14933 (2002).
Gilbert, Mark R. et al., "Cilengitide in patients with recurrent glioblastoma: the results of NABTC 03-02, a phase II trial with measures of treatment delivery," J. Neurooncol., 106(1):147-53 (Jan. 2012).
Goncalves, V et al., "Rational design, structure, and biological evaluation of cyclic peptides mimicking the vascular endothelial growth factor," J. Med. Chem., 50:5135-5146 (2007).
Goodsell, DS and Olson, AJ, "Automated docking of substrates to proteins by simulated annealing," Proteins, 8:195-202 (1990).
Guerrero, Carlos A. et al., "Integrin $α_vβ_3$ mediates rotavirus cell entry," Proc. Natl. Acad. Sci., 97(26):14644-14649 (Dec. 19, 2000).
Halekoh, Ulrich et al., "The R Package geepack for Generalized Estimating Equations," J. Stat. Soft., 15(2):1-11 (Jan. 2006).
Harris, TD et al., "Design, synthesis, and evaluation of radiolabeled integrin αvβ3 receptor antagonists for tumor imaging and radiotherapy," Cancer Biother. Radiopharm., 18(4):627-641 (2003).
Haubner, Roland et al., "Glycosylated RGD-containing peptides: tracer for tumor targeting and angiogenesis imaging with improved biokinetics," J. Nucl. Med., 42(2):326-336 (Feb. 2001).
Haubner Roland et al., "Radiolabeled $α_vβ_3$ integrin antagonists: a new class of tracers for tumor targeting," J. Nucl. Med., 40(6):1061-1071 (Jun. 1999).
Haubner, Roland et al., "Structural and functional aspects of RGD-containing cyclic pentapeptides as highly potent and selective integrin antagonists," J. Am. Chem. Soc., 118(32):7461-7472 (Aug. 14, 1996).
Honig, B and Nicholls, A, "Classical electrostatics in biology and chemistry," Science, 268(5214):1144-1149 (1995).
Hood, John D. et al., "Tumor regression by targeted gene delivery to the neovasculature," Science, 296(5577):2404-2407 (Jun. 28, 2002).
Hynes, RO, "Integrins: versatility, modulation, and signaling in cell adhesion" Cell, 69(1):11-25 (1992).
Izaguirre, J et al., "Langevin stabilization of molecular dynamics," J. Chem. Phys., 114(5):2090-2098 (2001).
Janssen, Marcel et al., "Improved tumor targeting of radiolabeled RGD peptides using rapid dose fractionation," Cancer Biother. Radiopharm., 19(4): 399-404 (Sep. 24, 2004).
Jorgensen, W et al., "Comparison of simple potential functions for simulating liquid water," J. Chem. Phys., 79(2):926-935 (1983).
Kanu, OO et al., "Glioblastoma multiforme: a review of therapeutic targets," Expert Opin. Ther. Targets, 13(6):701-18 (2009).
Kim JH et al., "Self-assembled glycol chitosan nanoparticles for the sustained and prolonged delivery of antiangiogenic small peptide drugs in cancer therapy," Biomaterials, 29(12):1920-30 (2008).
Kollman, PA et al., "Calculating structures and free energies of complex molecules: combining molecular mechanics and continuum models," Accounts Chem. Res., 33(12):889-897 (2000).
Liu Zhaofei et al., "$^{68}$Ga-labeled cyclic RGD dimers with $Gly_3$ and $PEG_4$ linkers: promising agents for tumor integrin αvβ3 PET imaging," Eur. J. Nucl. Med. Mol. Imaging, 36(6):947-57 (Jan. 22, 2009).
Magrath, IT, "Targeted approaches to cancer therapy," Int. J. Cancer, 56(2):163-166 (Jan. 15, 1994).
Mammen, Mathai et al., "Polyvalent Interactions in Biological Systems: Implications for Design and Use of Multivalent Ligands and Inhibitors," Angew. Chem. Int. Ed., 37:2754-2794 (1998).

(56) References Cited

OTHER PUBLICATIONS

Mittra, Erik S. et al., "Pilot pharmacokinetic and dosimetric studies of 18F-FPPRGD2: a PET radiopharmaceutical agent for imaging $\alpha_v\beta_3$ integrin levels," Radiology, 260(1):182-91 (Jul. 2011).

Morris, GM et al., "Automated docking using a Lamarckian genetic algorithm and empirical binding free energy function," *J. Comput. Chem.*, 19:1639-1662 (Nov. 15, 1998).

Morris, Garrett M. et al., "Distributed automated docking of flexible ligands to proteins: parallel applications of AutoDock 2.4," *J. Comput. Aided Mol. Des.*, 10:293-304 (1996).

Mulder, A et al., Multivalency in supramolecular chemistry and nanofabrication. Org. Biomol. Chem., 2:3409-24 (2004).

Nabors, L. Burt et al., "A safety run-in and randomized phase 2 study of cilengitide combined with chemoradiation for newly diagnosed glioblastoma (NABTT 0306)," *Cancer*, 118(22):5601-5607 (Nov. 15, 2012).

Noiri E et al., "Biodistribution and clearance of $^{99m}$Tc-labeled Arg-Gly-Asp (RGD) peptide in rats with ischemic acute renal failure," *J. Am. Soc. Nephrol.*, 7(12):2682-2688 (Dec. 1, 1996).

Ntziachristos, Vasilis et al., "Fluorescence imaging with near-infrared light: new technological advances that enable in vivo molecular imaging," *Eur. Radiol.*, 13(1):195-208 (Jan. 2003).

Onthank, David C. et al., "90Y and 111 in complexes of a DOTA-conjugated integrin $\alpha_v\beta_3$ receptor antagonist: different but biologically equivalent," *Bioconjug. Chem.*, 15(2):235-241 (Feb. 2004).

Park, Kyeongsoon et al., "Antiangiogenic effect of bile acid acylated heparin derivative," *Pharm. Res.*, 24(1):176-85 (Jan. 2007).

Parsons, D. Williams et al., "An integrated genomic analysis of human glioblastoma multiforme," *Science*, 321(5897):1807-12 (Sep. 26, 2008).

Pasqualini, R et al., "Alpha v integrins as receptors for tumor targeting by circulating ligands," Nat. Biotechnol., 15(6):542-546 (1997).

Pierschbacher, Michael D. and Ruoslahti, Erkki, "Cell attachment activity of fibronectin can be duplicated by small synthetic fragments of the molecule," *Nature*, 309(5963): 30-33 (May 3, 1984).

Rao, J. et al., "A trivalent system from vancomycin. D-ala-D-Ala with higher affinity than avidin.biotin," *Science*, 280(5364):708-11 (May 1, 1998).

Ruoslahti, Erkki and Pierschbacher, Michael D., "Arg-Gly-Asp: a versatile cell recognition signal," *Cell*, 44(4):517-518 (Feb. 28, 1986).

Ryckaert, Jean-Paul et al., "Numerical integration of the Cartesian equations of motion of a system with constraints: molecular dynamics of n-alkanes," *J. Comput. Phys.*, 23(3):327-341 (Mar. 1977).

Schnitzer, JE, "Vascular targeting as a strategy for cancer therapy," New. Engl. J. Med., 339:472-474 (1998).

Schottelius, Margret et al., "Ligands for mapping $\alpha v\beta 3$-integrin expression in vivo," *Acc. Chem. Res.*, 42(7):969-80 (Jun. 2, 2009).

Sevick-Muraca, EM et al., "Fluorescence-enhanced, near infrared diagnostic imaging with contrast agents," Curr. Opin. Chem. Biol., 6:642-50 (2002).

Shi, Jiyun et al., "Improving tumor uptake and excretion kinetics of 99mTc-labeled cyclic arginine-glycine-aspartic (RGD) dimers with triglycine linkers," *J. Med. Chem.*, 51(24):7980-90 (Dec. 25, 2008).

Sivolapenko, GB et al., "Imaging of metastatic melanoma utilizing a technetium-99m labeled RGD-containing synthetic peptide," Eur. J. Nucl. Med., 25:1383-1389 (1998).

Smolarczyk, Ryszard et al., "Antitumor effect of RGD-4C-GG-$_D$(KLAKLAK)$_2$ peptide in mouse B16(F10) melanoma model," *Acta Biochim. Pol.*, 53(4):801-805 (2006).

Takagi, J and Springer, TA, "Integrin activation and structural rearrangement," Immunol. Rev., 186:141-163 (2002).

Van Hagen, P. M. et al., "Evaluation of a radiolabelled cyclic DTPA-RGD analogue for tumour imaging and radionuclide therapy," *Int. J. Cancer*, 90(4):186-198 (Aug. 20, 2000).

Wang, J et al., "Development and testing of a general amber force field," J. Comput. Chem., 25(9):1157-74 (2004).

Wickham, Thomas J. et al., "Integrins $\alpha_v\beta_3$ and $\alpha_v\beta_5$ promote adenovirus internalization but not virus attachment," *Cell*, 73(2):309-319 (Apr. 23, 1993).

Wu, Yun et al., "MicroPET imaging of glioma integrin $\alpha_v\beta_3$ expression using $^{64}$Cu-labeled tetrameric RGD peptide," *J. Nucl. Med.*, 46(10):1707-1718 (Oct. 1, 2005).

Xie, Jianwu et al., "Tumor angiogenic endothelial cell targeting by a novel integrin-targeted nanoparticle," *Int. J. Nanomedicine*, 2(3):479-85 (Sep. 2, 2007).

Xiong, Jian-Ping et al., "Crystal structure of the extracellular segment of integrin $\alpha V\beta 3$ in complex with an Arg-Gly-Asp Ligand," Science, 296(5565):151-155 (Apr. 5, 2002).

International Search Report and Written Opinion for International Application No. PCT/US2009/52608, dated Sep. 9, 2009, 13 Pages.

International Preliminary Report on Patentability for International Application No. PCT/US2009/52608, dated Feb. 10, 2011, 2 Pages.

\* cited by examiner

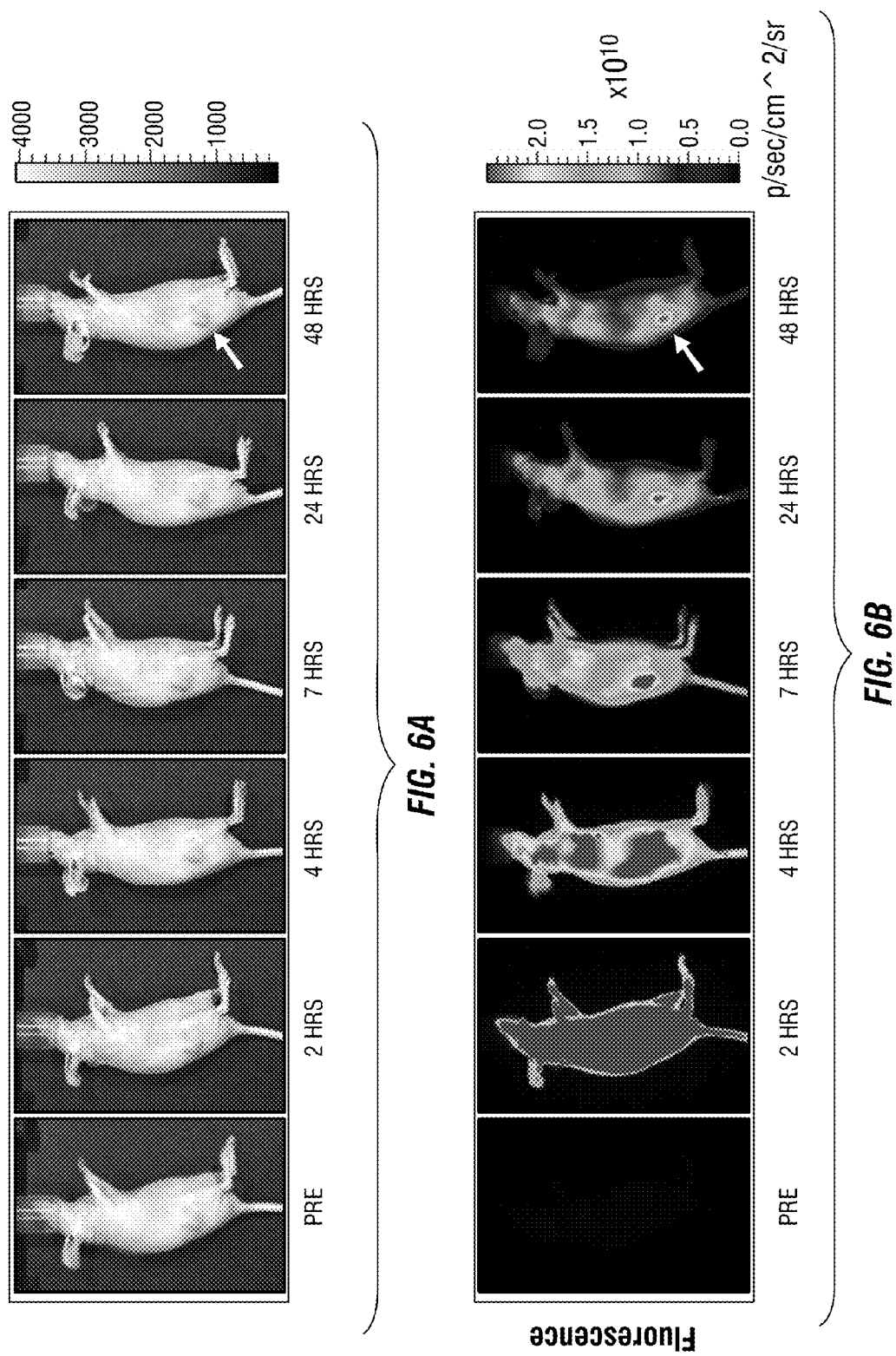

Free Cy5.5

Bivalent-IA-Cy5.5

Free Cy5.5

Bivalent-IA-Cy5.5

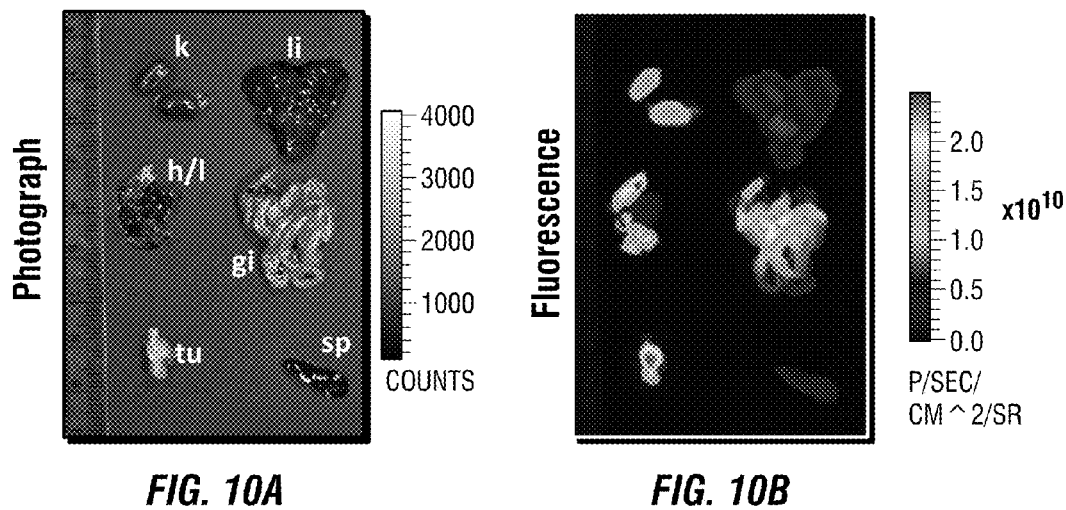
FIG. 10A  FIG. 10B
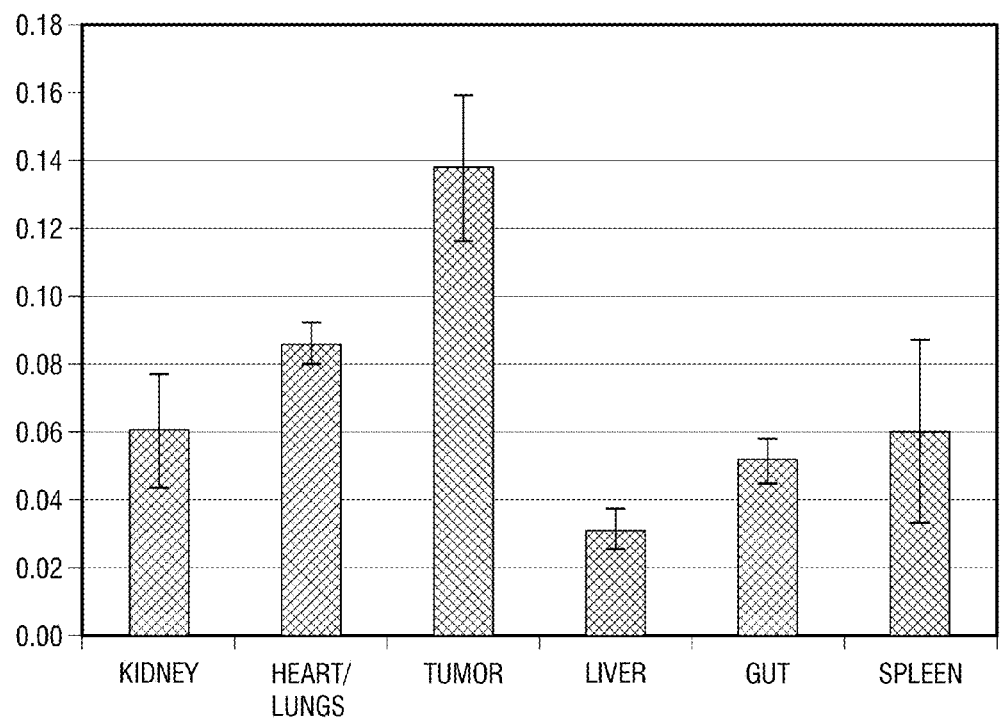
FIG. 10C

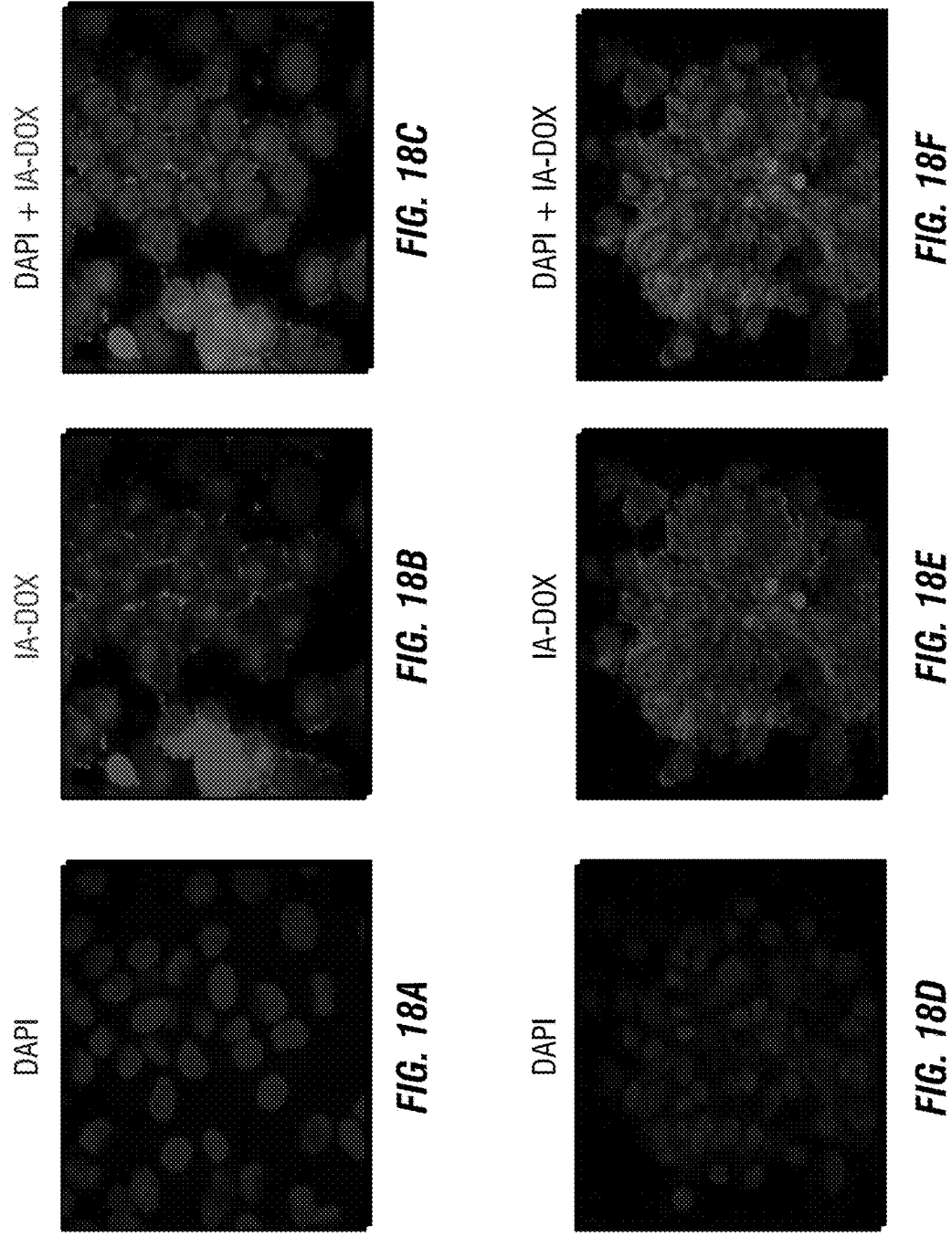

IA TRIMER understand # LABELED, NON-PEPTIDIC, MULTIVALENT INTEGRIN ANTAGONIST COMPOUNDS; METHODS FOR SYNTHESIS AND USES THEREOF

CROSS-REFERENCE TO RELATED APPLICATIONS

The present application claims priority to PCT Intl. Pat. Appl. No. PCT/US2012/022712, filed Jan. 26, 2012, which claimed priority to U.S. Provisional Patent Application No. 61/436,527 filed Jan. 26, 2011; the contents of each of which is specifically incorporated herein in its entirety by express reference thereto.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

BACKGROUND OF THE INVENTION

Field of the Invention

The present invention relates generally to the fields of medicine and pharmaceuticals. In particular, multivalent integrin receptor antagonists are provided, including near-infrared (NIR), fluorescent, non-peptidic, integrin $\alpha_v\beta_3$ compounds (as well as formulations and compositions thereof) that are useful in a variety of prophylactic and/or therapeutic regimens, and one or more diagnostic imaging modalities, including, for example, in the detection of mammalian cancer cells in vivo, or in situ.

Description of Related Art

The integrins are a family of heterodimeric trans-membrane receptors each consisting of α and β subunits. To date, a total of 18 α and 8 β subunits have been discovered in mammalian cells, forming at least 24 different integrin receptors. Each integrin subunit includes a large extracellular, a single transmembrane and a short cytoplasmic domain. Based on the key roles they play in angiogenesis, leukocyte function and tumor development and their easy accessibility as cell surface receptors interacting with extracellular ligands, the integrin superfamily, integrin $\alpha_v\beta_3$ in particular, have been extensively investigated as imaging and chemotherapy targets (Chen, 2011).

Integrin $\alpha_v\beta_3$ is a receptor for extracellular proteins including vitronectin, fibronectin and fibrinogen that contain an arginine-glycine-aspartic acid (RGD) sequence (DeNardo et al., 2000; Janssen et al., 2004). RGD peptides specific binding to $\alpha_v\beta_3$ receptor have been labeled with various gamma and positron emitters for scintigraphic detection (Chen et al., 2004; Harris et al., 2003; Haubner et al., 2004; Haubner et al., 1999; van Hagen et al., 2000) and gamma and beta emitters for radiotherapy of tumors (Bernard et al., 2004; Capello et al., 2004; DeNardo et al., 2000; Janssen et al., 2004; Onthank et al., 2004). Steady progress has been reported in optimizing the labeling methodologies to increase tumor-to-nontumor tissue ratios, especially the tumor-to-liver and tumor-to-kidney ratios by increasing the hydrophilicity of the product via glycosylation and PEGylation of radiolabeled RGD peptides (Chen et al., 2004a; Chen et al., 2004b; Chen et al., 2004; Haubner et al., 2001).

Dimeric and tetrameric RDG peptides labeled with $^{18}F$ and $^{64}Cu$ were prepared for positron emission tomography (PET) imaging for cancer diagnosis (Chen et al., 2004b; Chen et al., 2005; Wu et al., 2005). It was reported that these oligomeric RDG peptides enhanced the receptor-binding affinity, thereby improving the tumor targeting and slowing the wash-out of radioactivity from tumor.

Receptors on the surfaces of mammalian cells participate in many biological cellular processes, including, for example, cell proliferation and invasion. One particular receptor that has implications for a wide variety of disease conditions is the vitronectin receptor αvβ3. A member of the integrin superfamily of receptors, αvβ3 is found in various cells including angiogenic endothelia and osteoclasts. Integrins have been implicated in a variety of disorders and diseases and disorders, including, cancer and inflammation, as well as autoimmune and genetic diseases and disorders. $\alpha_v\beta_3$ plays a critical in vivo role in endothelial cell survival during angiogenesis, and also potentiates the internalization of various cellular viruses including, rotavirus, adenovirus, and foot-and-mouth disease virus.

Development of antagonists of the integrin $\alpha_v\beta_3$ receptor have been described, and monovalent integrin $\alpha_v\beta_3$ receptor antagonists having a tetrahydropyridi-midinylaminoethyl-oxybenzoyl group conjugated to a sulfonylamino-β-alanine nucleus have been synthesized as noted in U.S. Pat. Appl. Publ. No. 2006/0030575 (specifically incorporated herein in its entirety by express reference thereto). The development of multivalent integrin $\alpha_v\beta_3$ antagonists, have not, however, been reported.

Thus, there is a need in the art to develop new, improved integrin antagonist compounds that (1) bind to $\alpha_v\beta_3$ integrin receptors with higher specificity and/or higher affinity than existing compounds; (2) bind to selected target cells (such as, for example, mammalian tumor cells) with high affinity, and with substantial specificity; and (3) are more resistant to cleavage and/or degradation from one or more endogenous or exogenous proteases (including, for example, those found in plasma, the gastrointestinal tract, tumor cells, and other mammalian tissues).

BRIEF SUMMARY OF THE INVENTION

The present invention provides new and useful compositions, as well as methods of employing them that may advantageously improve delivery of therapeutic, diagnostic and/or prophylactic agents to an animal in need thereof.

In an important embodiment, the invention provides a bifunctional compound that includes a first targeting moiety defined as a synthetic or semisynthetic, small-molecule, peptidomimetic, multivalent integrin αvβ3 antagonist moiety that is operably linked to at least one detectable moiety, at least one therapeutic agent, or any combination thereof.

In particular aspects, the multivalent integrin $\alpha_v\beta_3$ antagonist moiety is characterized as a bivalent, a trivalent, a tetravalent, a pentavalent, a hexavalent, or a heptavalent integrin $\alpha_v\beta_3$ antagonist moiety and in particular embodiments includes the formula of one or more of the following antagonist moieties:

IA 1
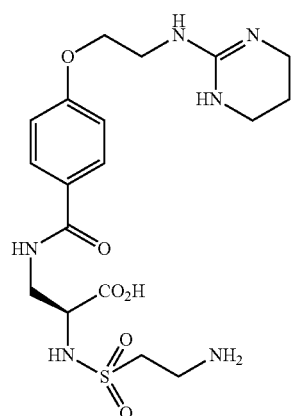
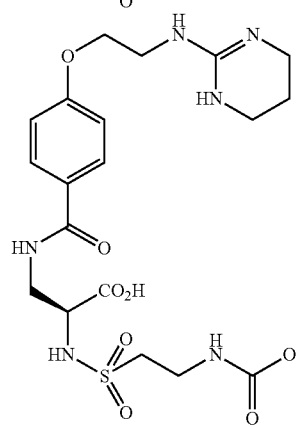 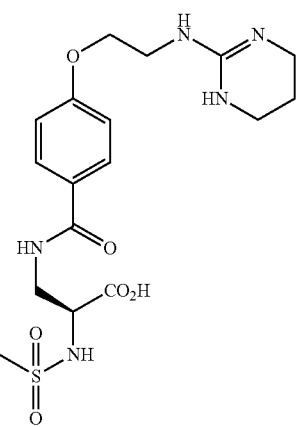
3: n = 1; 4: n = 2; 5: n = 6
IAC 2
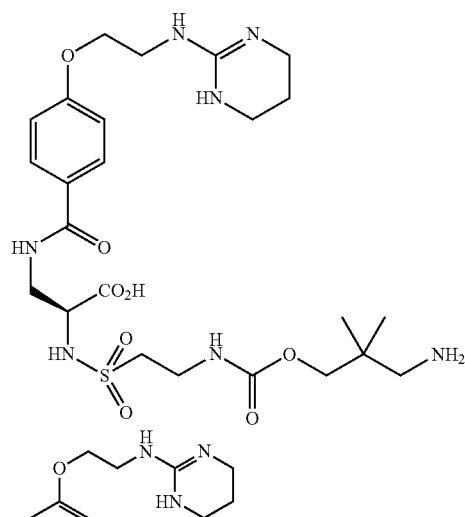
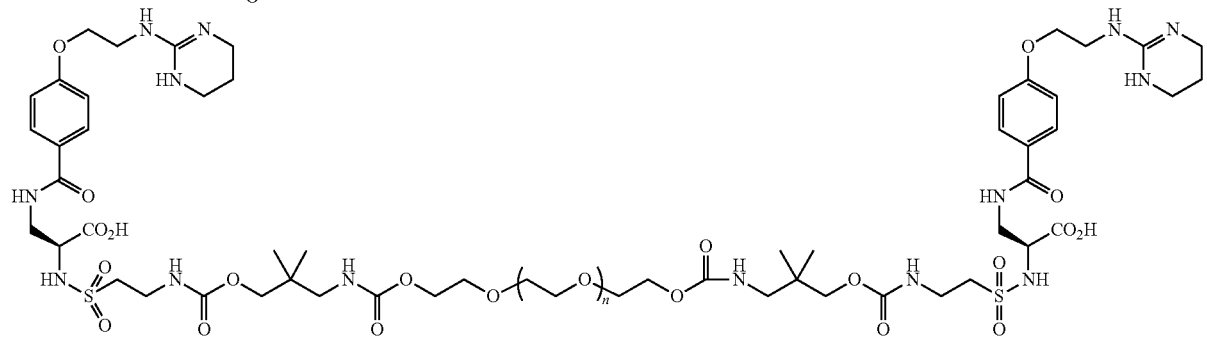
6: n = 1; 7: n = 2; 8: n = 6

In particular embodiments, the integrin $\alpha_v\beta_3$ antagonist moiety has the formula: 4-[2-(3,4,5,6-tetrahydropyrimidine-2-ylamino)ethyloxy]benzoyl-2-(S)-aminoethyl sulfonylamino-β-alanine.

In the practice of the invention, the detectable moiety includes one or more detectable labels such as a near-infrared label, a fluorescent label, a radiolabel, a magnetic spin resonance label, a chromophore, or any combination thereof. Exemplary labels include, without limitation, fluorescent labels such as fluorescein, rhodamine, Texas Red, a Cy2, moiety, a Cy3 moiety, a Cy5 moiety, a Cy 5.5 moiety, or a Cy 7 moiety, a cyanine dye, or a derivative or any combination thereof. In the case of radiolabel compounds, the molecule may include 18F, 64Cu, or a combination thereof.

The bifunctional compounds of the invention may be synthesized with one or more linker moieties, including without limitation, PEG, tri(ethylene glycol), tetra(ethylene glycol), n-(ethylene glycol), where n is from 3 to 12, 2-aminooctanedioic acid, triethanolamine, or any combination, analog, or derivative thereof.

The bifunctional compounds of the invention may be included within a nanoparticle, a microparticle, a nanocapsule, a microbubble, a microcapsule, a nanosphere, or a microsphere, or any combination thereof; or (b) further comprising a surfactant, a neutral lipid, a lipid complex formed from at least two distinct lipids, a liposome, a niosome, an ethosome, a transferosome, a phospholipid, a sphingosome, or any combination thereof, and in particular therapeutic and diagnostic modalities, may be preferably formulated within a nanoparticle delivery system, such as a polymerized, liposomal-based, nanoparticle delivery system.

Such formulations of the present invention may optionally include, one or more neutral lipids (including, without limitation, one or more of a cephalin, a ceramide, a cerebroside, a cholesterol, a diacylglycerol, a diacylphosphatidylcholine, a diacylphosphatidylethanolamine, a phosphatidylcholine, a phosphatidylethanolamine, a sphingolipid, a sphingomyelin, a tetraether lipid), as well as combinations and derivatives thereof.

In an exemplary illustrative embodiment, the bifunctional compound has the chemical formula:

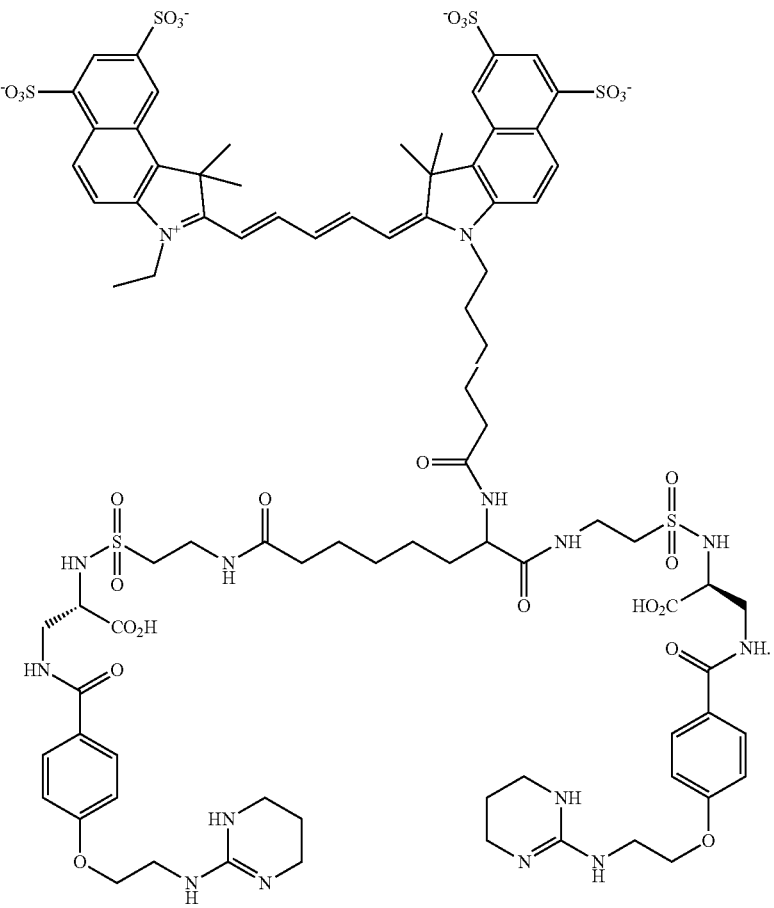

In the practice of the various diagnostic and therapeutic methods described herein, the bifunctional compounds of the invention are preferably formulated within a pharmaceutically-acceptable diluent, buffer, or vehicle, and particularly ones that are suitable for administering the bifunctional compounds to a mammal, such as a human patient in need thereof.

When used as a therapeutic delivery vehicle, the compounds of the invention will preferably include at least one therapeutic agent (including, without limitation, one or more of an antineoplastic agent, an immunomodulating agent, a neuroactive agent, an anti-inflammatory agent, an anti-lipidemic agent, a hormone, a hormone receptor, a receptor agonist, a receptor antagonist, an anti-infective agent, or a compound selected from a protein, a peptide, an antibody, an enzyme, an RNA, a DNA, an siRNA, an mRNA, an RNAi, a ribozyme, a cofactor, a steroid, an antisense oligonucleotide, a detection agent, an imaging agent, a contrast agent, a gas, a pharmaceutically-active molecule, a targeting moiety, a linker, and any combinations thereof).

In exemplary illustrative embodiments, the bifunctional compound includes the antineoplastic agent doxorubicin.

The invention also provides a method for treating or ameliorating at least one symptom of a disease, dysfunction, or abnormal condition in a mammal. The method, in an overall and general sense, includes at least the step of providing to the mammal one or more of the bifunctional therapeutic integrin-receptor antagonist compounds disclosed herein, in an amount, and for a time sufficient to treat or ameliorate the at least one symptom of the disease, dysfunction, or abnormal condition in the mammal.

The invention further provides a method of detecting or imaging of a population of integrin receptor-presenting cells within or about the body of an animal. In an overall and general sense, this method includes at least the step of providing or administering to one or more cells, tissues, or organs of the animal at least one of the bifunctional therapeutic compounds disclosed hererin, in an amount and for a time sufficient to detect or image at least a first portion of the population of integrin receptor-presenting cell in the mammal to which the detectable moiety is bound. In exemplary embodiments, the detectable moiety is identifiable by confocal microscopic imaging, CT imaging, PET imaging, MRI, or any combination thereof.

In another embodiment, the invention provides a method for imaging a first population of integrin $\alpha_v\beta_3$-expressing cells within or about the body of an animal. In an overall and general sense, the method includes administering to the animal an amount of one or more of the bifunctional compounds disclosed herein, for a time effective to image the first population of integrin $\alpha_v\beta_3$-expressing cells within or about the body of the animal. The integrin $\alpha_v\beta_3$-expressing cells may typically include one or more cancer cells, one or more tumor cells, one or more hyperproliferative cells, or any combination thereof. In particular embodiments, one or more of the population of targeted cells will express at least a first integrin $\alpha v\beta 3$ receptor on its cell surface, to which the bifunctional compound is localized by virtue of its integrin-targeting moiety.

In the practice of the method, the animal recipient may be a mammal, including a human, that is suspected of having, diagnosed with, or at risk for developing one or more cancers, tumors, or such like. In certain embodiment, the first population of integrin $\alpha v\beta 3$-expressing cells, or the first population of tumor cells is located within or about the body of a mammalian patient, and the method comprises systemically or directly administering an effective amount of one or more of the therapeutic bifunctional compounds disclosed herein to the mammalian patient for an period to treat, lessen, or ameliorate one or more symptoms of the disease.

In diagnostic modalities, the detectable moiety is preferably an imaging moiety that is useful in one or more diagnostic methodologies such as microscopic imaging, near-IR microscopic imaging, fluorescent microscopic imaging, confocal microscopic imaging, or any combination thereof.

In particular, a new class of integrin receptor antagonists has now been discovered that advantageously displays high binding affinity, specificity for integrin $\alpha v\beta 3$, and inherent stability. These ligands are particularly useful for imaging of tumor, organs, and/or tissues, as well as for treating or ameliorating one or more symptoms of cancer, inflammatory disease, autoimmune disease, and the like. Pharmaceutical formulations and kits containing these new compounds, suitable for imaging, diagnosis, prophylaxis, and/or therapy are also provided.

The present invention resides in these compounds themselves, and in pharmaceutical compositions containing one or more of the compounds together with a pharmaceutically acceptable carrier. The invention also encompasses the administration of such compound(s) or pharmaceutical compositions including the compounds to mammals afflicted with a condition that is mediated at least by a multivalent (i.e., polyvalent) integrin receptor, and most notably $\alpha_v\beta_3$, as treatment for the condition. Exemplary multivalent compounds include, but are not limited to, bivalent, trivalent, tetravalent, pentavalent, hexavalent, and heptavalent integrin receptor antagonists, and the like. In particularly exemplary embodiments described herein, bivalent integrin receptor antagonists were shown to be particularly useful in the practice of the methods described herein, although other polyvalent compounds are contemplated to be similarly useful, and in certain applications, may demonstrate superior results than those illustrated herein for the bivalent test compound described in the following illustrative examples.

The invention further encompasses the administration of the imaging agents that contain such compound(s) linked to a detectable moiety, or pharmaceutical compositions of such imaging agents, as part of the imaging of multivalent integrin receptor cells, again most notably $\alpha_v\beta_3$-bearing cells, in the mammal.

As will be noted from the description below, this invention further encompasses treatment and prevention of various disease conditions, symptoms thereof, or both, that are associated with the biological activity of one or more multivalent integrin receptors, most notably $\alpha_v\beta_3$, by either blocking (i.e., inhibiting, the receptor), or by modifying cells that bear one or more such receptors on or about their cell membranes or on at least a first portion of their cellular surface, such that delivery of one or more polynucleotides or polypeptides of interest may be delivered to the cells as a result of the binding of the disclosed delivery agents to such receptors, thereby permitting uptake or introduction of the target molecule to the selected cells of interest by employing one of the multivalent integrin antagonist delivery agents.

In an overall and general sense, the invention provides small-molecule compounds (and particularly non-peptidic, polyvalent/multivalent integrin antagonist compounds), as well as compositions and formulations comprising them, that are useful in a variety of medical imaging, diagnostic, prophylactic, and therapeutic regimens.

In a first embodiment, the invention provides non-peptidic (i.e., "small molecule") integrin antagonist compounds, and preferably one or more polyvalent compounds (e.g., one or more bivalent, trivalent, tetravalent, pentavalent, hexavalent, heptavalent, etc.) that specifically target, specifically bind to, and/or specifically uptaken by one or more particular mammalian cell surface receptors. In illustrative embodiments, these mammalian cell surface receptors include human receptors such as the integrin $\alpha_v\beta_3$ receptor.

In exemplary embodiments, the invention provides a bivalent, integrin $\alpha_v\beta_3$ antagonist-moiety-containing bifunctional compound, the targeting moiety having the structural formula of one or more of the following compounds:

IA 1
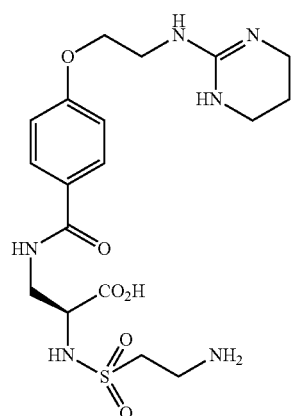
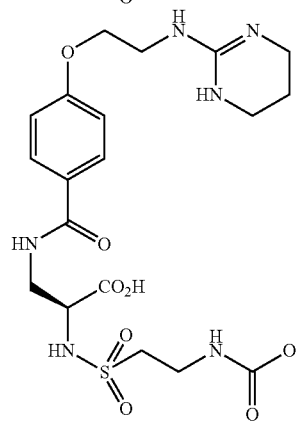 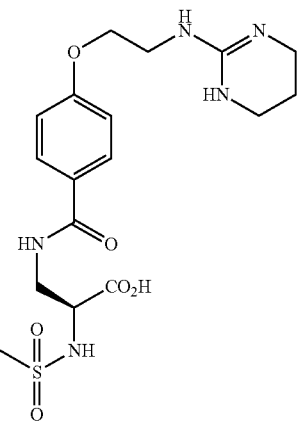
3: n = 1; 4: n = 2; 5: n = 6
IAC 2
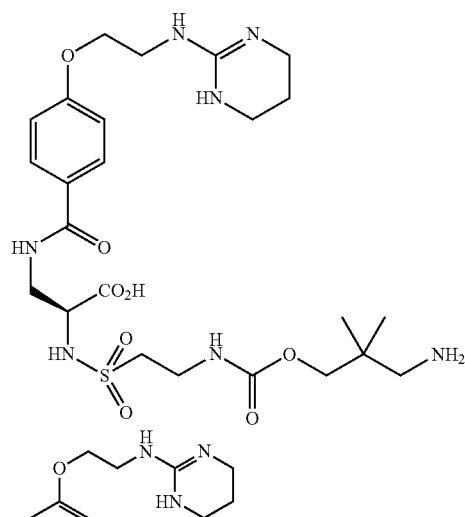
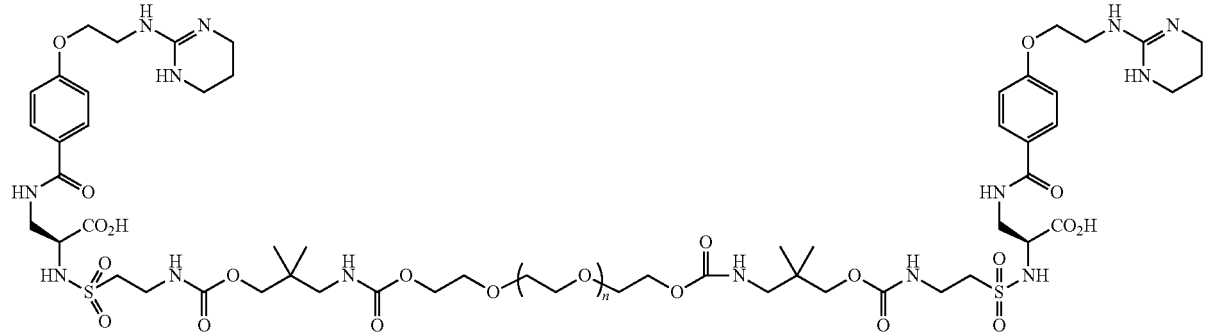
6: n = 1; 7: n = 2; 8: n = 6

In certain embodiments, a bifunctional integrin $\alpha_v\beta_3$ antagonist moiety-containing molecule preferably includes at least a first imaging moiety that includes at least a first detectable label, such as, without limitation, a fluorescent label such as the Cy5.5 moiety. In exemplary embodiments, the bifunctional molecules include a bivalent integrin $\alpha_v\beta_3$ antagonist compound operably linked to a first reporter molecule (such as a fluorescent moiety such as Cy5.5), wherein the labeled compound has the formula:

more nanoparticles, microparticles, nanocapsules, microcapsules, nanospheres, or microspheres, or any combination thereof.

Preferred pharmaceutical composition of the present invention also include those that further comprise one or more of an antineoplastic agent, an immunomodulating agent, a neuroactive agent, an antiinflammatory agent, an antilipidemic agent, a hormone, a receptor agonist or antagonist, or an antiinfective agent, or a compound selected from

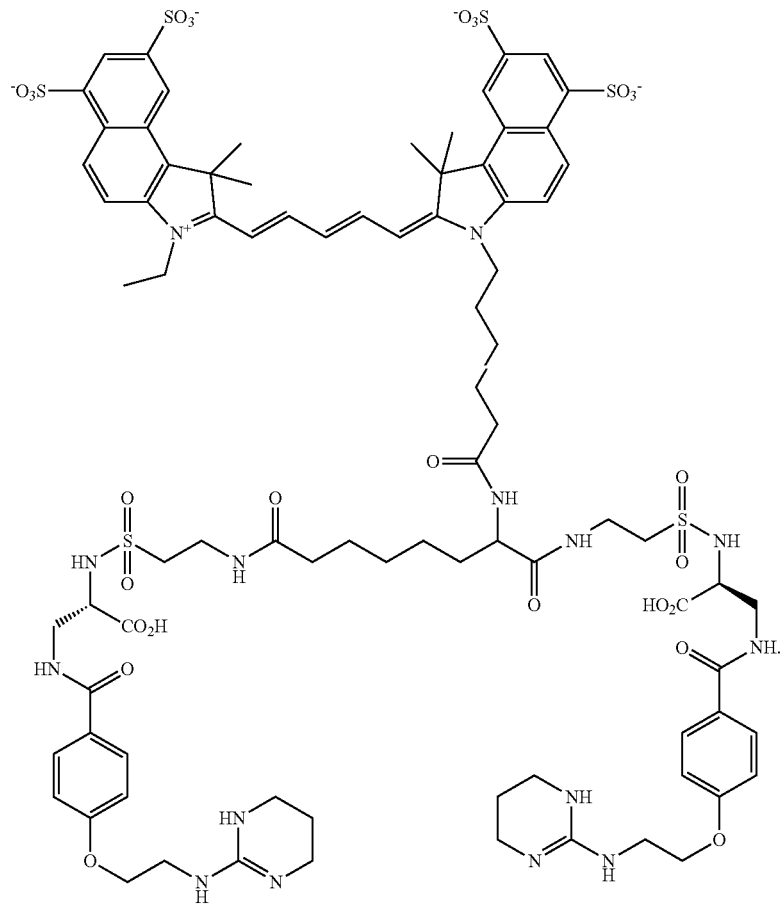

As noted herein, in certain embodiments, the disclosed integrin antagonist compounds of the invention are formulated as a pharmaceutical composition, that may include one or more pharmaceutically-acceptable buffers, diluents, vehicles, and the like. Likewise, in the practice of the invention, it may be desirable to formulate the integrin antagonist compounds of the invention by the addition of one or more surfactants, neutral lipids (including, without limitation, one or more cephalins, ceramides, cerebrosides, cholesterols, diacylglycerols, diacylphosphatidylcholines, diacylphosphatidylethanolamines, phosphatidylcholines, phosphatidylethanolamines, sphingolipids, sphingomyelins, tetraether lipids, or any combination thereof), lipid complexes (including, e.g., those formed from two or more distinct lipids), liposomes, niosomes, ethosomes, transferosomes, phospholipids, sphingosomes, or any combination thereof.

Optionally, the compounds of the invention may be formulated into compositions that are comprised within one or a protein, a peptide an antibody, an enzyme, an RNA, a DNA, an siRNA, an mRNA, a ribozyme, a hormone, a cofactor, a steroid, an antisense molecule, a detection agent, an imaging agent, a contrast agent, a gas, and a pharmaceutically-active molecule.

Preferably, the compounds, compositions, and pharmaceutical formulations of the present invention are formulated for administration to an animal host cell, and to mammalian host cells, such as human host cells, in particular.

The multivalent, integrin antagonist compounds of the present invention (as well as compositions and formulations comprising one or more of them) find particular utility in diagnosis (including, without limitation, in the diagnosis of a disease, disorder, dysfunction, abnormal condition, trauma, or one or more symptoms thereof), in medical imaging (including, without limitation, in one or more confocal microscopic imaging modalities), or in the prophylaxis or therapy of one or more diseases, dysfunctions, disorders, or abnormal conditions in an animal (including, without limitation, in a mammal such as a human).

The invention also provides use of one or more of the disclosed compounds in the manufacture of a medicament for the medical imaging, diagnosis, or treatment of one or more hyperproliferative disorders, including, without limitation, cancer and such like.

The invention further provides use of one or more of the disclosed compounds in the manufacture of a diagnostic imaging agent, and particularly NIR fluorescently labeled integrin antagonist compounds useful in confocal microscopy and other medical imaging modalities.

The invention also provides a method of treating a mammal that is afflicted with a condition that is mediated by an integrin receptor. In an overall and general sense, such a method generally involves administering to a mammal in need thereof, an amount of one or more of the disclosed integrin antagonist compounds, in an amount and for a time sufficient to treat or ameliorate one or more symptoms of such a condition.

A further aspect of the invention is a method of imaging cells, organs, and/or tissues about or within the body of an animal that express one or more integrin receptor-presenting cells. In an overall sense, the method typically involves providing to a mammalian patient in need thereof, a first detectably-labeled integrin antagonist compound in an amount and for a time sufficient to image such cells, organs, and/or tissues.

In related embodiments, the invention also provides a method of imaging one or more tumors, or pluralities of tumor cells, in a patient afflicted with, suspected of having, or diagnosed with, one or more hyperproliferative diseases (e.g., tumor growth). In an overall and general sense, such a method typically involves administering to, or providing a patient in need thereof, with an amount of one or more of the disclosed labeled integrin antagonist compounds and for a time effective to facilitate the imaging of one or more such tumors or integrin receptor presenting cells in the patient. In certain embodiments, the integrin antagonist compound is labeled with a detectable moiety, and preferably a near-infrared fluorescent moiety, such as a Cy5.5 label and the like, or a radiolabeled moiety, including, without limitation, an $^{18}F$ or a $^{64}Cu$ moiety. In exemplary embodiments, the tumor cells to be identified using the disclosed methods will preferably express one or more integrin $\alpha_v\beta_3$ receptors on or about the surface of at least a first population of tumor cells, such that the compounds of the invention may selectively "target" those tumor cells by virtue of the antagonist moiety binding to its corresponding surface-expressed receptor.

In another embodiment, the invention provides methods for imaging one or more populations of integrin $\alpha_v\beta_3$-expressing cells within or about the body of a mammalian patient, or for targeting to such cells, one or more therapeutic, diagnostic, or prophylactic reagents. In an overall sense, such methods generally involve providing to the patient at least a first labeled integrin antagonist composition as disclosed herein, in an amount and for a time sufficient to image the one or more populations of such integrin $\alpha_v\beta_3$-expressing cells within or about the body of the mammalian patient. Such a method preferably includes one or more optical imaging techniques such as near-infrared fluorescent confocal microscopy or such like.

In particular embodiments, the present invention provides for the use of one or more of the disclosed multivalent integrin antagonist compositions, and multivalent integrin $\alpha_v\beta_3$ antagonist compositions in particular, in the manufacture of a medicament for diagnosis, prophylaxis, therapy, or medical imaging, and particularly for use in the manufacture of a medicament for imaging, diagnosing, treating, and/or preventing one or more diseases, dysfunctions, or disorders in a mammal, or a symptom thereof, or a combination of the foregoing, and in a human in particular.

The present invention also provides for the use of one or more of the disclosed multivalent integrin antagonist compositions, and multivalent integrin $\alpha v\beta 3$ antagonist compositions in particular, in the manufacture of a medicament for the medical imaging, diagnosis, prophylaxis and/or therapy of one or more medical conditions, including, for example, cancer; diabetes; neurological disorders; cerebrovascular accidents; stroke, ischemia, infarction, aneurysm, musculoskeletal deficiencies; neuromuscular disorders; osteogenic diseases peptide, polypeptide, or enzyme deficiencies; hormone, cofactor, or trophic factor deficiencies; one or more cardiovascular and/or cardiocirculatory diseases, disorders, or dysfunctions; organ disease, dysfunction, or failure; genetic disorders; congenital abnormalities, defects, or malformations; trauma; and the like.

The present invention also provides for the use of one or more of the disclosed multivalent integrin antagonist compositions, and multivalent integrin $\alpha_v\beta_3$ antagonist compositions in particular, in the manufacture of a medicament for the prevention of disease, including, in the preparation of one or more vaccines suitable for prophylactic administration.

Those of ordinary skill in the art will appreciate from the present disclosure that the integrin antagonist compounds of the invention may also be co-administered with one or more additional prophylactic and/or therapeutic agents for the prevention, treatment, and/or amelioration of one or more symptoms of hyperproliferative, inflammatory, and/or autoimmune diseases, and the like. Suitable anti-inflammatory agents for combination therapy include, without limitation, corticosteroids, non-steroidal anti-inflammatory agents, antibodies such as infliximab, 5-aminosalicylates, antibiotics, pharmaceutically acceptable salts thereof; derivatives thereof, prodrugs thereof, and combinations thereof. Suitable immunosuppressive agents for combination therapy include, without limitation, azathioprine and metabolites thereof, anti-metabolites such as methotrexate, immunosuppressive antibodies, mizoribine monophosphate, cyclosporine, scoparone, rapamycin, glatiramer acetate, mycopehnolate, pharmaceutically acceptable salts thereof, derivatives thereof, prodrugs thereof, and combinations thereof.

The invention also provides methods for providing a therapeutic, prophylactic, or diagnostic compound to a first cell in a mammal, with the method generally including providing to a mammal in need thereof, an effective amount of a bifunctional multivalent integrin $\alpha_v\beta_3$ antagonist composition that is operably linked to at least one therapeutic, prophylactic, and/or diagnostic moiety, and for a time effective to provide the desired therapy, prophylaxis or diagnosis in one or more cells and/or tissues of the selected mammal receiving the compound(s).

In certain aspects of the invention, the invention provides integrin antagonist compositions (and multivalent integrin $\alpha_v\beta_3$ antagonist compositions in particular), for delivering one or more compounds to a host cell. In particular embodiments, the host cell is preferably a mammalian host cell, and one that expresses an integrin receptor, such as the integrin $\alpha_v\beta_3$ receptor. In certain preferred embodiments of the invention, the host cell is a human cell. In other preferred aspects, the host cell is included within the body of a human, or included within at least a first ex vivo tissue or plurality of cells that are compatible for implantation into the body of such a human as part of a typical ex vivo therapy protocol or such like.

In other aspects of the invention, integrin antagonist compositions, and integrin $\alpha_v\beta_3$ antagonist compositions in particular, are provided that may further optionally include one or more additional distinct components, including, without limitation, one or more therapeutics, one or more diagnostics, or one or more imaging compounds, or any combination thereof.

Similarly, the disclosed integrin antagonist compositions, and multivalent integrin $\alpha_v\beta_3$ antagonist compositions in particular, may also be formulated in association with one or more additional vehicles for delivering an agent to an animal, including, for example, fully-polymerized liposomes, partially-polymerized liposomes, cross-linked lipids, unpolymerized liposomes, niosomes, transferosomes, ethosomes, phospholipid complexes, lipid particles, lipid vesicles, nanoparticles, microparticles, nanocapsules, microcapsules, microspheres, nanospheres, sphingosomes, and such like.

In certain embodiments, the antagonist compositions of the present invention can be formulated with one or more surfactants, neutral lipids, lipid complexes, liposomes, niosomes, ethosomes, transferosomes, phospholipids, sphingosomes, or any combination thereof. Exemplary neutral lipids include, without limitation, a cephalin, a ceramide, a cerebroside, a cholesterol, a diacylglycerol, a diacylphosphatidylcholine, a diacylphosphatidylethanolamine, a phosphatidylcholine, a phosphatidylethanolamine, a sphingolipid, a sphingomyelin, a tetraether lipid, or any combination thereof. In certain embodiments, the integrin antagonist compositions of the present invention may be comprised within a liposome, a nanoparticle, a microparticle, a nanocapsule, a microcapsule, a nanosphere, or a microsphere, or any combination thereof. Methods for the preparation of liposomal formulations are known to those of ordinary skill in the molecular pharmaceutical arts. Liposomes, for example, may be formed by any conventional technique, including without limitation, by extrusion, sonication, or mechanical shearing, or a combination thereof. Entrapment of the antagonist compositions (optionally together with one or more additional active ingredient [s]) into suitable lipid vesicles may also be accomplished by any conventional technique, including, without limitation, exposure of the lipid vesicles to UV light in the presence of the active ingredient(s).

The compositions of the present invention may also be delivered to cells in association with one or more conventional pharmaceutical compounds or compositions, which preferably may provide diagnosis, prophylaxis, and/or treatment of the same (or different) type as provided by the multivalent integrin antagonist composition itself.

Therapeutic, Prophylactic and Diagnostic Methods

Another important aspect of the present invention concerns methods for using the disclosed multivalent integrin antagonist compositions, and multivalent integrin $\alpha_v\beta_3$ antagonist compositions in particular, to treat or ameliorate the symptoms of one or more diseases, dysfunctions, or deficiencies in an animal, and preferably in a mammal such as a human. Such methods generally involve administration to the animal in need thereof, one or more of the disclosed antagonist compounds or compositions, in an amount and for a time sufficient to treat or ameliorate the symptoms of such a deficiency in the affected animal. The methods may also encompass prophylactic treatment of animals suspected of having such conditions, or administration of such compositions to those animals at risk for developing such conditions either following diagnosis, or prior to the onset of symptoms.

As such, preferred animals for administration of the pharmaceutical compositions disclosed herein include mammals, and particularly humans. Other preferred animals include non-human primates, bovines, ovines, caprines, lupines, equines, porcines, canines, and felines, as well as animals under the care of a veterinary practitioner.

Pharmaceutical Formulations

In certain embodiments, the present invention concerns formulation of one or more therapeutic or diagnostic agents in a pharmaceutically acceptable composition for administration to a cell or an animal, either alone, or in combination with one or more other modalities of diagnosis, prophylaxis, and/or therapy. The formulation of pharmaceutically-acceptable excipients and carrier solutions is well known to those of ordinary skill in the art, as is the development of suitable dosing and treatment regimens for using the particular compositions described herein in a variety of diagnostic and therapeutic regimens.

In certain circumstances it will be desirable to deliver the compositions of the present invention in suitably-formulated pharmaceutical vehicles by one or more standard delivery techniques or routes of administration, including, for example, subcutaneously, intraocularly, intravitreally, parenterally, intravenously, intracerebroventricularly, intramuscularly, intrathecally, orally, intraperitoneally, transdermally, topically, by oral or nasal inhalation, or by direct injection to one or more cells, tissues, or organs. The methods of administration may also include those modalities as described in U.S. Pat. Nos. 5,543,158; 5,641,515, and 5,399,363, each of which is specifically incorporated herein in its entirety by express reference thereto. Solutions of the active compounds as freebase or pharmacologically acceptable salts may be prepared in sterile water, and may be suitably mixed with one or more surfactants, such as hydroxypropylcellulose. Dispersions may also be prepared in glycerol, liquid polyethylene glycols, oils, or mixtures thereof. Under ordinary conditions of storage and use, these preparations contain a preservative to prevent the growth of microorganisms.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous, and intraperitoneal administration. For such preparations, any available sterile aqueous medium can be employed as will be known to those of ordinary skill in the art in light of the present disclosure. For example, one dosage may be dissolved in 1 mL of isotonic NaCl solution, and either added to 1000 mL of hypodermoclysis fluid or injected at the proposed site of infusion (see, for example, "Remington's Pharmaceutical Sciences" 15th Edition, pages 1035-1038 and 1570-1580). Some variation in dosage will necessarily occur depending on the condition of the subject being treated and other known dosing factors. The person responsible for administration will determine, in any event, the appropriate dose for the individual subject. Moreover, for human administration, preparations should meet sterility, pyrogenicity, and the general safety and purity standards as required by FDA Office of Biologics standards.

Sterile injectable compositions may be prepared by incorporating the disclosed integrin antagonist compounds in the required amount in the appropriate solvent with several of the other ingredients enumerated above, as required, followed by filtered sterilization. Generally, dispersions can be prepared by incorporating the selected sterilized active ingredient(s) into a sterile vehicle including the basic dispersion medium and other ingredients as needed from those discussed herein. The integrin antagonist compositions, and in particular, the multivalent integrin $\alpha_v\beta_3$ antagonist compositions disclosed herein, may also be optionally formulated in one or more neutral or salt form(s). Pharmaceutically-acceptable salts include the acid addition salts (formed with the free amino groups of the protein), and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like. Upon formulation, solutions will be administered in a manner compatible with the dosage formulation, and in such amount as is effective for the intended application. The formulations are readily administered in a variety of dosage forms such as injectable solutions, topical preparations, oral formulations, including sustain-release capsules, hydrogels, colloids, viscous gels, transdermal reagents, intranasal and inhalation formulations, and the like.

The amount of integrin antagonist compositions, and multivalent integrin $\alpha_v\beta_3$ antagonist compositions in particular, as well as the time or duration needed for the administration of such composition(s), will be within the purview of the ordinary-skilled artisan particularly given the benefit of the present teachings. It is likely, however, that the administration of a therapeutically-effective, pharmaceutically-effective, prophylactically-effective, and/or diagnostically-effective amount of the disclosed multivalent integrin antagonist compositions may be achieved by a single administration, such as for example, a single injection of a sufficient quantity of the delivered agent to provide the desired benefit to the patient undergoing such a procedure. Alternatively, in some circumstances, it may be desirable to provide multiple, or successive, administrations of the multivalent integrin antagonist compositions, either over a relatively short, or even a relatively prolonged period of time, as may be determined by the medical practitioner overseeing the administration of such compositions to the selected individual.

Typically, formulations of one or more active ingredients in the pharmaceutical formulations disclosed herein will contain an effective amount of the integrin antagonist compound for the selected therapy, prophylaxis, diagnosis, and/or imaging (e.g., a prophylactically-, therapeutically-, diagnostically-, or imaging-effective amount). Preferably, the formulation may contain at least about 0.1% of each active ingredient, although the percentage of the active ingredient(s) may, of course, be varied, and may conveniently be present in amounts from about 0.5 to about 80 weight % or volume %, or from about 1 to about 70 weight % or volume %, or more preferably, from about 2 to about 50 weight % or volume %, based upon the total formulation. Naturally, the amount of active compound(s) in each composition may be prepared in such a way that a suitable dosage will be obtained in any given unit dose of the compound. Factors such as solubility, bioavailability, biological $t_{1/2}$, route of administration, product shelf life, as well as other pharmacological considerations will be contemplated by one of ordinary skill in the art of preparing such pharmaceutical formulations, and as such, a variety of dosages and treatment regimens may be desirable.

In one embodiment, administration may be parenterally, intravenously, intramuscularly, or even intraperitoneally. The pharmaceutical forms adapted for injectable administration include sterile aqueous solutions or dispersions, and sterile powders for the extemporaneous preparation of sterile injectable solutions or dispersions including without limitation those described in U.S. Pat. No. 5,466,468, which is specifically incorporated herein in its entirety by express reference thereto). In all cases, the form must be sterile and must be fluid to facilitate syringability. Such a dosage form must be at least sufficiently stable under the conditions of manufacture and storage, and must be preserved against the contaminating action of microorganisms, such as viruses, bacteria, fungi, and such like. The carrier can be a solvent or dispersion medium containing, for example, water, ethanol, polyol (e.g., glycerol, propylene glycol, and liquid polyethylene glycol, and the like, or a combination thereof), one or more vegetable oils, or any combination thereof, although additional pharmaceutically-acceptable components may be included.

It is contemplated that formulations of the disclosed multivalent integrin antagonist compositions may be suitable for direct injection into one or more organs, tissues, or cell types in the body. Such injection sites include, but are not limited to, the circulatory system, the spinal cord, the lymphatic system, a joint or joint capsule, a synovium or subsynovium tissue, tendons, ligaments, cartilages, bone, periarticular muscle or an articular space of a mammalian joint, as well as direct administration to an organ or tissue site such as the heart, liver, lung, pancreas, intestine, brain, bladder, kidney, or other site within the patient's body, including, for example, introduction of the delivered therapeutic or diagnostic agent(s) via intra-abdominal, intrathoracic, intravascular, or intracerebroventricular delivery of a suitable formulation. Administration of the disclosed compositions need not be restricted to one or more of these delivery routes, but instead may be conducted using suitable techniques, including those known to the one of ordinary skill in the relevant medical arts. In certain embodiments the active ingredients of the invention may be formulated for delivery by needle, catheter, and related techniques, or alternatively, may be included within a medical device, including, for example, drug-eluting implants, stents, catheters, and such like. The formulations may also be prepared for injection by an implanted drug-delivery pump or similar mechanism.

The administration of the disclosed pharmaceutical compositions by intranasal sprays, inhalation, and/or other aerosol delivery vehicles is also contemplated. Methods for delivering peptide and non-peptidic compositions directly to the lungs via nasal aerosol sprays have been described e.g., in U.S. Pat. Nos. 5,756,353 and 5,804,212, each of which is specifically incorporated herein in its entirety by express reference thereto. Delivery of drugs using intranasal microparticle resins (see e.g., Takenaga et al., 1998) and lysophosphatidyl-glycerol compounds (U.S. Pat. No. 5,725,871, specifically incorporated herein in its entirety by express reference thereto) are also well-known in the pharmaceutical arts. Likewise, transmucosal drug delivery in the form of a polytetrafluoroethylene support matrix is suitable in the practice of the invention, and is described in U.S. Pat. No. 5,780,045 (specifically incorporated herein in its entirety by express reference thereto).

The disclosed multivalent integrin antagonist compositions may also be administered through transdermal or other topical administration routes. Exemplary methods for the use of disclosed formulations in topical therapy are found, for example, in U.S. Pat. Nos. 5,540,936, and 6,133,451, each of which is specifically incorporated herein in its entirety by express reference thereto.

In particular embodiments, the disclosed multivalent integrin antagonist compositions can be formulated using one or more pharmaceutical buffers, vehicles, or diluents, and intended for administration to a mammal through suitable techniques, such as, by intramuscular, intravenous, subcutaneous, intrathecal, intra-abdominal, intravascular, intra-articular, or alternatively, by direct injection to one or more cells, tissues, or organs of such a mammal.

The multivalent integrin antagonist formulations disclosed herein are useful in any animal, and are not in any way limited to use only in humans, or even to primates, or mammals. In preferred embodiments, however, the compositions of the present invention may be formulated for administration to a mammal, including humans, for a variety of diagnostic, therapeutic, and/or prophylactic regimens. Such compositions may also be provided in excipient formulations that are acceptable for veterinary administration, including, for example, to selected livestock, exotic or domesticated animals, companion animals (including pets and such like), non-human primates, as well as zoological or otherwise captive specimens, and such like. Such methods may also encompass prophylactic treatment of one or more animals suspected of having, or at risk for developing one or more such conditions either following diagnosis, or prior to the onset of symptoms. To that end, in certain embodiments the multivalent integrin antagonist compositions disclosed and/or described herein may also find utility in the area of vaccine development, antigen administration, vaccination, and such like.

Kits

Kits including one or more of the disclosed multivalent integrin antagonist compositions or pharmaceutical formulations including such; and instructions for using the kit in a therapeutic, prophylactic, diagnostic, and/or other clinical embodiment also represent preferred aspects of the present disclosure. Such kits may further include one or more of the disclosed multivalent integrin antagonist compositions, either alone, or in combination with one or more additional prophylactic, therapeutic or diagnostic compounds, or one or more pharmaceuticals, and such like. The kits of the invention may be packaged for commercial distribution. They may also further optionally include one or more devices for delivering the multivalent integrin antagonist compositions to an animal (e.g., syringes, injectables, and the like). Such kits may be therapeutic kits for treating, preventing, or ameliorating the symptoms of a disease, deficiency, dysfunction, and/or injury, and may include one or more of the multivalent integrin antagonist compositions, and instructions for using the kit in a therapeutic, prophylactic, diagnostic, and/or medical imaging regimen.

The container for such kits may typically include at least one vial, test tube, flask, bottle, syringe or other container, into which the composition(s) may be placed, and preferably suitably aliquotted. Where a second composition is also provided, the kit may also contain a second distinct container into which this second composition may be placed. Alternatively, the plurality of compositions may be prepared and packaged in a single container, such as a vial, flask, syringe, catheter, cannula, bottle, or other suitable single container or delivery device.

The kits of the present invention may also typically include a retention mechanism adapted to contain or retain the vial(s) or other container(s) in close confinement for commercial sale, such as, e.g., injection or blow-molded plastic containers into which the desired vial(s) or other container(s) may be retained to minimize or prevent breakage, exposure to sunlight, or other undesirable factors, or to permit or facilitate ready use of the composition(s) included within the kit.

Alternatively, such kits may be prepared that include at least one pharmaceutical formulation as disclosed herein and instructions for using the composition in diagnosis and/or for one or more medical imaging modalities. The container for such kits may typically include at least one vial, test tube, microcentrifuge tube, or other container, into which the multivalent integrin composition(s) may be placed and suitably aliquotted. Where a radiolabel or fluorigenic label, or other such detecting component, is included within the kit, the labeling agent may be provided either in the same container as the multivalent integrin antagonist composition, or may alternatively be placed in a second distinct container into which this second composition may be placed and suitably aliquotted. Alternatively, the multivalent integrin antagonist compositions may be prepared in combination with one or more additional reagents in a single container, and in most cases, the kit will also typically include a retention mechanism adapted to retain or contain the vial(s) or other container(s) in close confinement for commercial sale and/or convenient packaging and delivery to minimize or avoid any undesirable environmental factors.

Compositions for the Preparation of Medicaments

Another important aspect of the present invention concerns methods for using the disclosed compositions (as well as formulations including them) in the preparation of medicaments for preventing, treating or ameliorating the symptoms of various diseases, dysfunctions, or deficiencies in an animal, such as a vertebrate mammal. Use of the disclosed compositions is also contemplated in therapy and/or prophylaxis of one or more diseases, disorders, dysfunctions, conditions, disabilities, deformities, or deficiencies, or any symptom thereof, particularly when the multivalent integrin antagonist composition is formulated to include one or more therapeutic (or prophylactic) agents known to one of ordinary skill in the medical arts.

Such use generally involves administration to an animal in need thereof one or more of the disclosed compositions that include at least a first therapeutic or prophylactic agent, in an effective amount and for a time sufficient to prevent, treat, lessen, or ameliorate one or more symptoms of such a disease, disorder, dysfunction, condition, disability, deformity, or deficiency in the affected animal.

Compositions including one or more of the disclosed formulations also form part of the present invention, and particularly compositions that further include at least a first pharmaceutically-acceptable excipient for use in the therapy, prophylaxis, or diagnosis of one or more diseases, dysfunctions, disorders, or such like.

Use of the disclosed multivalent integrin antagonist compositions is also contemplated, particularly in the manufacture of one or more medicaments and methods involving one or more therapeutic (including chemotherapy, phototherapy, laser therapy, etc.), prophylactic (including e.g., vaccines), or diagnostic regimens (including, e.g., in diagnostic imaging such as radiology, scintigraphy, microscopy (including, without limitation, confocal laser-scanning microscopy), ultrasound, PET, CT, MRI, and the like).

Such multivalent integrin antagonist formulations may optionally further include one or more additional distinct reagents, such as a diagnostic reagent, a lipid, lipid complex, phospholipid, a liposomal delivery formulation, or any other such vehicle(s), additive(s) and/or adjuvant(s) as may be suitable for administration of the multivalent integrin antagonist composition to an animal in need thereof. Such routes of administration are known to and may be selected by those of ordinary skill in the art, and include, for example, but are not limited to, delivery routes including intramuscular, intravenous, intra-arterial, intrathecal, intracavitary, intraventricular, subcutaneous, or direct injection into an organ, tissue site, or population of cells in the recipient animal, or other routes noted herein.

BRIEF DESCRIPTION OF THE DRAWINGS

For promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The invention may be better understood by reference to the following description taken in conjunction with the accompanying drawings, in which like reference numerals identify like elements, and in which:

FIG. 5A and FIG. 5D are fluorescence images, FIG. 5B and FIG. 5E are bright-field images, and FIG. 5C and FIG. 5F are fusion images, each taken from the same field-of-view. Confocal laser-scanning microscopy images of U-87 glioblastoma incubated with bivalent-IA-Cy5.5 demonstrated endocytosis of the imaging probes (FIG. 5A through FIG. 5C). A U-87 cell-blocking study using non-fluorescent bivalent IA demonstrated a complete blockage of endocytosis of the imaging probes (see FIG. 5D, FIG. 5E, and FIG. 5F);

FIG. 6A and FIG. 6B show photographic, and corresponding near-infrared images, respectively, of a time-course series of a live U-87 xenograft tumor-bearing mouse, recorded at selected time points. The photon scale is shown on the right in series FIG. 6A, while the corresponding radiance scale is shown on the right for the series in FIG. 6B (p/sec/cm2/sr). The murine subject in this illustrative study was anesthetized with 1.5-2.0% isoflurane through a nosecone. The arrow in the 48-hr time-point indicates the location of the tumor within the body of the mouse;

FIG. 9A and FIG. 9B are photographic images of live U-87 xenograft tumor-bearing mice at 24 hours post-intravenously-administered un-conjugated Cy5.5 (FIG. 9A) vs. bivalent IA-Cy5.5 (FIG. 9B), respectively (the photon scale is shown at right). The lower panel (FIG. 9C, and FIG. 9D) show the corresponding near-infrared fluorescent imaging of the same animals, with the radiance scale shown as a color bar to the right (in units of p/sec/cm2/sr). The two mice in this representative study were anesthetized with 1.5-2.0% isoflurane through a nosecone. Black paper was used to cover the injection sites in the lateral tail veins and the location of the tumors are indicated by arrows;

FIG. 10A, FIG. 10B, and FIG. 10C show representative ex vivo NIR imaging of major internal organs harvested from a xenograft tumor-bearing mice at 24 hours post i.v. injection of bivalent IA-Cy5.5. FIG. 10A (top panel) is a photographic image (photon scale shown to the right), while FIG. 10B (bottom panel) is a fluorescence image (in units of p/sec/cm2/sr) of the same organs. Harvested organs were: kidneys (k); liver (li); heart and lungs (h/l); small and large intestines (gi); spleen (sp), and the U-87 tumor (tu); FIG. 10C shows the biodistribution of bivalent IA-Cy5.5 at 24 hrs' post-injection averaged from two subjects, with the Y-axis presented in units of total photon flux per gram of tissue;

FIG. 13A: IA monomer compound (1); FIG. 13B: IA dimer compound (4) (n=2); FIG. 13C: IA dimer compound (5) (n=6); FIG. 13D: IAC monomer compound (2); FIG. 13E: IAC dimer compound (7) (n=2); and FIG. 13F: IAC dimer compound (8) (n=6);

FIG. 18A, FIG. 18B, FIG. 18C, FIG. 18D, FIG. 18E, and FIG. 18F show the results of an exemplary fluorescent imaging assay of M21 cells (FIG. 18A-FIG. 18C) and U87 cells (FIG. 18D-FIG. 18F) incubated with IA-doxorubicin shown in (FIG. 18A and FIG. 18D) DAPI stain, (FIG. 18B and FIG. 18E) IA-doxorubicin; FIG. 18C is the overlay of FIG. 18A and FIG. 18B, while FIG. 18F is the overlay of FIG. 18D and FIG. 18E;

FIG. 26A (same as FIG. 2B) is a zoomed top view of cRGD-binding integrin $\alpha v\beta 3$; (FIG. 26B, FIG. 26C, and FIG. 26D show surface models of binding poses of IA monomer, dimer and trimer of the last frame of 3-ns MD trajectories. The $\alpha v$ and $\beta 3$ subunits are in light blue and tan (same in h-j), respectively, while IA ligands are in space-filling model;

FIG. 27A shows H-bond networks in the binding of cRGD to integrin $\alpha v\beta 3$ in X-ray crystal. The protein and ligand are shown in ribbon and stick models, respectively, while H-bonds are shown in dashed green lines; FIG. 27B, FIG. 27C, and FIG. 27D: H-bond networks in the binding of IA ligands to integrin $\alpha v\beta 3$ in MD simulations;

FIG. 31D shows representative tumor growth at endpoint. All tissue collected after sacrifice at 14 days. The impact of multivalency is clearly seen in the reduction in size going from monomer to dimer to trimer;

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Integrins

The integrins are a family of heterodimeric trans-membrane receptors each consisting of an $\alpha$ and a $\beta$ subunit. To date, 18 $\alpha$ and 8 $\beta$ subunits have been described in mammalian cells, forming at least 24 different integrin receptors. Each integrin subunit contains a large extracellular domain, a single transmembrane domain and a short cytoplasmic domain. The composition and morphology of integrin-dependent adhesions vary with the cell type, matrix and integrin, contributing to cell advancement, tissue remodeling and repair. Based on the key roles they play in angiogenesis, leukocyte function and tumor development and easy accessibility as cell surface receptors interacting with extracellular ligands, the integrin superfamily, integrin $\alpha_v\beta_3$ in particular, have been extensively investigated as imaging and chemotherapy targets.

Integrins are involved in a variety of cell signaling pathways by mediating cell adhesion, migration and proliferation through explicit non-covalent interactions with endogenous extra cellular matrix (ECM) proteins. One of the most important members of the integrin family is the integrin αvβ3, which is a heterodimeric transmembrane receptor protein that has been proven to be involved in the formation of angiogenesis, a phenomenon that occurs in major diseases such as cancer, osteoporosis, rheumatoid arthritis and macular degeneration. The distinct biological role of $\alpha_v\beta_3$ makes it an attractive target for the development of therapies for a variety of diseases. To date, six integrin inhibitors are being evaluated in clinical trials as anti-angiogenic agents for tumor imaging and therapy, which demonstrate remarkable affinity and selectivity to $\alpha_v\beta_3$.

Figure 11:
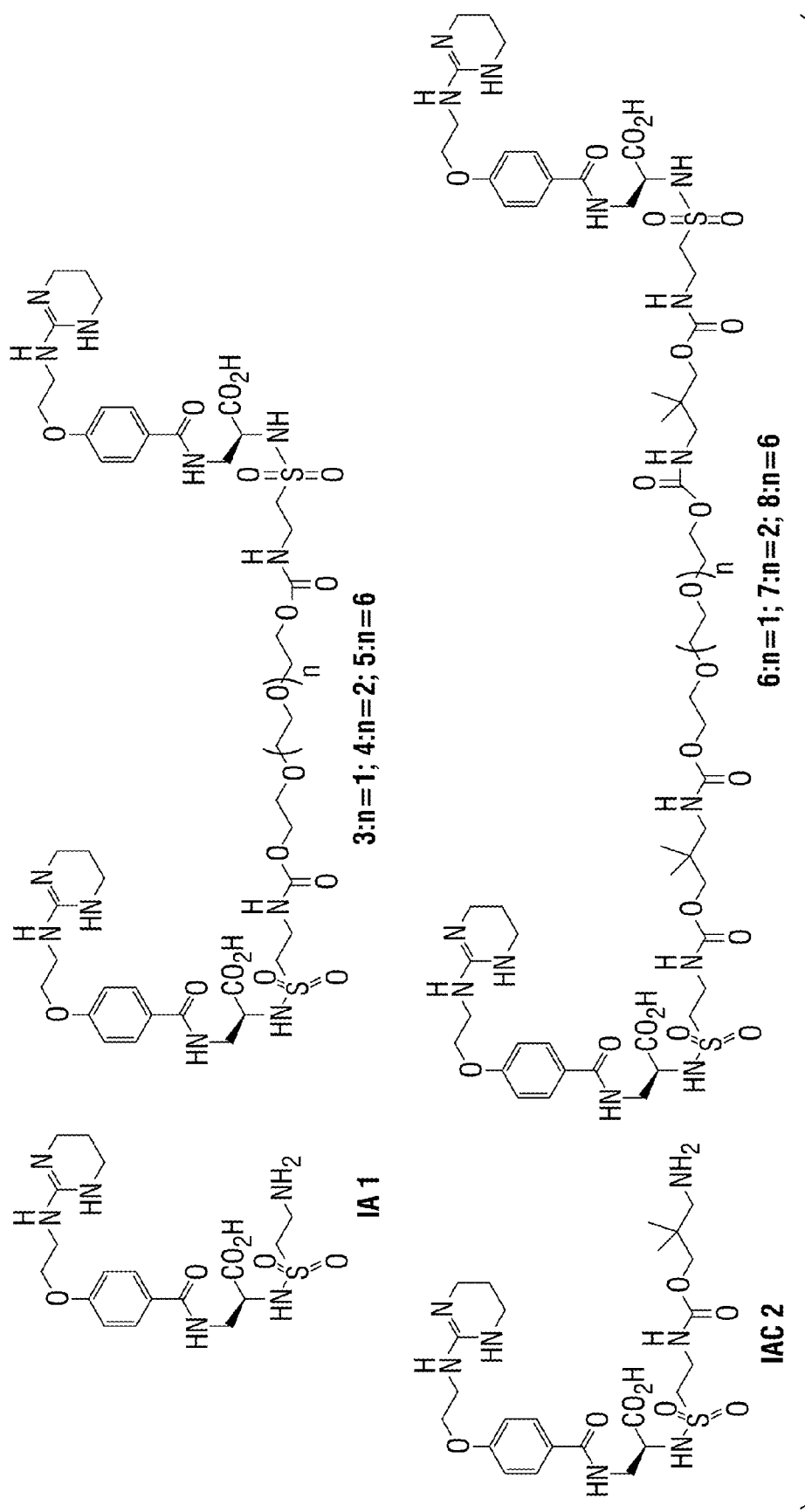
FIG. 11 shows the chemical structures of exemplary compounds in accordance with one aspect of the present invention. Shown are the compounds IA (1), IAC (2) and bivalent ligands (3), (4), (5), (6), (7), and (8)

Design of new multivalent therapeutic and imaging agents has received a lot of attention because of their potential for increased binding affinity to biological receptors. Bivalency, the most basic form of multivalency has already been adopted as a strategy in pharmaceutical research to improve interactions of designed ligands with natural receptors. A small molecule peptidomimetic integrin $\alpha_v\beta_3$ antagonist IA1 has been successfully exploited as the targeting agent for gene delivery to angiogenic blood vessels (FIG. 11). IAC 2, an IA carbamate derivative, has also been identified which enhanced $\alpha_v\beta_3$ binding affinity about 10-fold in comparison to native IA.

Chemotherapy has been the main approach for the systemic treatment of advanced or metastatic cancers for more than a half-century. During the cell division process, chemotherapeutics are capable of killing proliferating cells. While highly efficient in preventing disease progression, however, chemotherapeutic agents are often limited by their lack of selectivity for aberrant cells. Their toxicity to normal cells and non-diseased tissues, especially to rapidly dividing cells such as blood, bone marrow and mucous membrane cells, cause serious side-effects that limit the dose and regimen of the chemotherapeutic agents. Because of the intrinsic or acquired resistance of the cancer cells, the benefits of the chemotherapeutic agents are also often limited. The efficiency of the treatment can be increased by escalating the dose, but only at considerable risk of systemic damage. Selective delivery of chemotherapeutic agents to the disease site represents a major goal for improving the current chemotherapy outcome. Targeted delivery of chemotherapeutics is an emerging therapy strategy that should result in increased local efficacy while limiting peripheral toxicity. Clearly, the success of this approach is heavily reliant on the rational selection of appropriate biological targets.

Besides providing a surface receptor for targeted chemotherapeutics, the $\alpha_v\beta_3$ integrin receptor has also been shown to mediate the internalization of rotavirus and adenovirus. Integrin $\alpha_v\beta_3$ binds to the natural ligands vitronectin, fibrinogen, osteopontin, and bone sialoprotein by recognizing the amino acid sequence, Arg-Gly-Asp (RGD). Several research groups have synthesized peptide and peptidomimetic antagonists based on this motif that demonstrate remarkable affinity and selectivity to $\alpha_v\beta_3$. Recently, RGD peptides and peptidomimetic antagonists specific for $\alpha_v\beta_3$ receptor have been labeled with various gamma and positron emitters for scintigraphic detection and gamma and beta emitters for radiotherapy of tumors. Several reports have been focused on optimizing the labeling methodologies to increase tumor-to-non-tumor tissue ratios, particularly in the case of tumor-to-liver and tumor-to-kidney ratios by increasing the hydrophilicity of the product via glycosylation and/or PEGylation of radiolabeled RGD peptides. Recently, dimeric and tetrameric RGD peptides labeled with $^{18}F$ and $^{64}Cu$ were synthesized. It was reported that these oligomeric RGD peptides enhanced the receptor-binding affinity, thereby improving the tumor targeting and slowing the wash-out of radioactivity from tumor. The present invention exploits a peptidomimetic integrin $\alpha_v\beta_3$ antagonist, 4-[2-(3,4,5,6-tetrahydropyrimidine-2-ylamino) ethyloxy]benzoyl-2-(S)-aminoethylsulfonyl-amino-β-alanine (IA), as an integrin receptor-mediated tumor targeting agent. This agent, and related compounds described herein have been developed for tumor targeting, and in an illustrative aspect, delivered using a polymerized liposome-based, vascular-targeted, nanoparticle delivery system carrying a payload for simultaneous imaging and tumor therapy.

Valency

The valency of a microscopic entity is the number of separate connections of the same kind with another microscopic entity through host-guest interactions. Multivalency describes the binding of one or more entities that involves the simultaneous interaction between multiple, complementary functionalities on these entities. A multivalent entity is one that is able to connect to another entity through multiple separate attachments. There are many ways in which multivalent entities can interact with each other. Binding can occur in a multivalent fashion either intra-molecularly or inter-molecularly. Multivalency combines many advantageous features of self-assembly including reversibility, self-sorting, self-correction and the possibility of achieving thermodynamic and/or kinetic assembly stability at nano- or even picomolar concentrations. In biologic systems examples of multivalency are ubiquitous and they occur between many different types of molecules including protein to small molecule interactions (e.g., influenza viral attachment to cells via trimeric hemagglutinin A to sialic acid), oligosaccharide to protein interactions (neutrophil extravasation), protein-peptide interactions (e.g., *E. coli* infection of the renal system) and protein-sugar interactions (e.g., macrophage binding to pathogens). Because multivalent interactions afford unique properties as compared to monovalent interactions, significant research in the design of new therapeutic and imaging agents.

To optimally design multivalent ligands the most important aspects that need to be considered are the architecture of the multivalent entities and the thermodynamics of the interactions. In the present invention, a series of multivalent ligands for the integrin $\alpha_v\beta_3$ have been developed using a rational approach of developing multivalent ligands for protein targets employing computer modeling, followed by in vitro validation and in vivo testing.

Computer Modeling of Bivalent IA

The feasibility of the bivalent IA ligand development with computer modeling was tested, and several different dimers of IA with varying linker length and compositions were constructed. Molecular dynamics simulation of the solvated IA dimers was performed with CHARMM 35 force field.

The inclusion of ligand flexibility is crucial for large ligands having many rotatable bonds. For highly flexible ligands, low-energy conformations were generated through a simulated annealing (SA) search. This was performed using an MD trajectory at 1000° K followed by energy minimization, under the conditions R-die and GB/SA. A set of 10-20 lowest energy conformers, clustered according to coordinate RMS deviations, were docked to integrin using AutoDock 3.0 rigid-body docking method. Changes between the favored conformations in the free and bound state of the ligand provide important details about the internal strain generated by binding. Trivalent and tetravalent IAs have also been constructed, and they were analyzed using the same protocol.

IA dimer with (CCO)n linker (n=4→8) exhibited no substantial changes in the molecules conformation energy. IA trimer with (CCO)n, (n=4→8) showed a lowering in the conformational energy. With (CCC)n, (n=4→8) an increase in the conformational energy was observed. In case of IA tetramer with (CCO)n, (n=4→8) there was a small decrease in the conformational energy. The most significant finding is that there was a substantial decrease in the IA conformational energy when going from the mono-di-→tri-→tetrametric forms of IA.

As noted in the Examples that follow, to explore the nature of ligand-receptor interactions docking simulations were performed of the IA ligands to the integrin αvβ3 with AutoDock 3.05 (Scripps Research Institute, La Jolla, Calif., USA). While the protein was rigid, fixed at its crystal structure (1jv2), effects of ligand flexibility were included by sampling several IA conformations from the lowest energy clusters determined as described above. AutoDock simulations enabled the prediction of preferred protein-ligand binding modes, interaction strengths, and binding specificity from calculations of binding energies and ligand spatial distributions. For each protein-ligand pair, 10 LGA (Lamarckian genetic algorithm) docking runs were performed, with each run producing one possible binding mode or solution. The 10 solutions were first clustered in terms of the binding mode, i.e., the position and orientation of the ligand relative to the protein target. The total number of generated low-energy clusters measures the specificity of binding. A small number of clusters indicate that the ligand has only a few possible binding modes and interacts with a specific site (sites) on the target protein. On the other hand, a large number of clusters imply existence of a wide range of binding modes and lack of specific ligand-target interactions. The second step in sorting solutions involves identification of the solution of lowest binging energy within each cluster and ranking the different clusters according to this energy value. The solution with the lowest energy in the top-ranked (i.e., lowest-energy) cluster and all solutions with energies higher by up to 5.0 kcal/mol were considered as possible binding modes for ligand and target. Conformational energies of the structures appear below in Table 1, while interaction energies from AutoDock studies appear in Table 2.

TABLE 1

CONFORMATIONAL ENERGY OF INTEGRIN ANTAGONISTS (IA)

| Form of IA | Linker composition | Linker Length | Conformational Energy (kcal/mol) |
|---|---|---|---|
| Monomer | N/A | N/A | −17.0 ± 2 |
| Dimer (IA-IA) | (C—C—C)$_n$ | n = 3 | −97.0 ± 2.2 |
|  | (C—C—O)$_n$ | n = 3 | −96.0 ± 2.2 |
|  |  | n = 4 | −102.0 ± 2.2 |
|  |  | n = 8 | −102.0 ± 2.2 |
| Trimer (IA-IA-IA) | (C—C—O)$_n$ | n = 4 | −163.0 ± 2.0 |
|  |  | n = 8 | −185.0 ± 2.0 |
|  | (C—C—C)$_n$ | n = 4 | −174.0 ± 2.0 |
|  |  | n = 8 | −167.0 ± 2.0 |

TABLE 1-continued

CONFORMATIONAL ENERGY OF INTEGRIN ANTAGONISTS (IA)

| Form of IA | Linker composition | Linker Length | Conformational Energy (kcal/mol) |
|---|---|---|---|
| Tetramer (IA-IA-IA-IA) | (C—C—O)$_n$ | n = 4 | −227.0 ± 2.0 |
|  |  | n = 8 | −236.0 ± 2.0 |

TABLE 2

FREE ENERGY OF INTERACTION OF IAS FROM AUTODOCK

| IA Structure | Conformational Energy | Free Energy of Interaction |
|---|---|---|
| Monomer | −17.0 ± 2.0 | −1.04 ± 0.9 |
| Dimer (CCO)$_n$, n = 3 | −97.0 ± 2.2 | −2.0 ± 1.5 |
| Dimer (CCO)$_n$, n = 4 | −102.0 ± 2.2 | −2.1 ± 1.1 |
| Dimer (CCO)$_n$, n = 8 | −104.0 ± 2.2 | −4.02 ± 1.1 |

EXEMPLARY DEFINITIONS

In accordance with the present invention, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

The term "integrin," as used herein, refers to any of the many cell surface receptor proteins, also known as adhesion protein receptors, which bind extracellular matrix ligand or other cell adhesion protein ligands and thereby mediate cell-cell and cell-matrix adhesion processes. Integrins constitute a superfamily of membrane receptors that are encoded by genes belonging to a gene superfamily and are typically composed of heterodynamic transmembrane glycoproteins containing an α- and a β-subunit.

As used herein, an "integrin binding moiety," means an integrin-inhibiting moiety that specifically acts by binding to an integrin, thereby precluding, reversing, inhibiting or otherwise interfering with the binding of an integrin to its native ligand(s). When an integrin binding moiety is part of a molecule, it confers its property to the molecule, and the molecule becomes "targeted" to integrins, i.e., the molecule specifically and efficiently binds to an integrin. The binding between an integrin and an integrin binding moiety may be covalent or non-covalent, including, in this last case, hydrophobic interactions, electrostatic interactions, Van der Waals interactions, hydrogen bonding, etc.

The terms "integrin antagonist" and "integrin inhibitor" are used interchangeably herein, and mean molecules, agents, or compounds that inhibit or reduce the biological activity of integrin.

As used herein, the terms "imaging detectable moiety" and "imaging moiety" are interchangeable, and mean any moiety detectable by one or more imaging procedures, such that the moiety is able to provide, to improve or, in any way, to advantageously modify the signal detected by such an imaging diagnostic technique (including, for example, confocal near-infrared microscopy, magnetic resonance imaging, radioimaging (e.g., x-ray imaging), light (i.e., optical) imaging, etc. thus enabling the registration of diagnostically useful, preferably contrasted, images when used in association with the particular imaging techniques.

As described in U.S. Pat. Appl. Publ. No. 20060019900, and used herein, the term "cancer" refers to "any of various malignant neoplasms characterized by the proliferation of anaplastic cells that tend to invade surrounding tissue and metastasize to new body sites. Examples of different types of cancer suitable for treatment using the present invention include, but are not limited to, ovarian cancer, breast cancer, lung cancer, bladder cancer, thyroid cancer, liver cancer, pleural cancer, pancreatic cancer, cervical cancer, testicular cancer, colon cancer, anal cancer, bile duct cancer, gastrointestinal carcinoid tumors, esophageal cancer, gall bladder cancer, rectal cancer, appendix cancer, small intestine cancer, stomach (gastric) cancer, renal cancer, cancer of the central nervous system, skin cancer, choriocarcinomas; head and neck cancers, osteogenic sarcomas, fibrosarcoma, neuroblastoma, glioma, melanoma, leukemia, and lymphoma."

As used herein, the term "leukemia" refers to "a malignant disease, i.e., cancer, of the bone marrow and blood characterized by the uncontrolled accumulation of blood cells. Leukemia is divided into myelogenous or lymphocytic leukemia, each of which can be acute or chronic. The terms myelogenous or lymphocytic denote the cell type involved. Examples of the types of leukemia suitable for treatment using the present invention include, but are not limited to, acute lymphocytic leukemia, chronic lymphocytic leukemia, acute myelogenous leukemia, chronic myelogenous leukemia, and hairy cell leukemia."

The term "lymphoma," as used herein refers to "a group of cancers that originates in the lymphatic system. Lymphoma occurs when a lymphocyte (i.e., a type of white blood cell) undergoes a malignant change and begins to multiply, eventually crowding out healthy cells and creating tumors that enlarge the lymph nodes or other sites in the body. Examples of the types of lymphoma that may be particular responsive to treatment using one or more of the compositions of the present invention include, but are not limited to, non-Hodgkin's lymphoma, Hodgkin's lymphoma, B-cell lymphoma, acute lymphocytic leukemia, chronic lymphocytic leukemia, T-cell lymphoma, multiple myeloma, hairy cell leukemia, Burkitt's lymphoma, and the like.

The term "inflammatory disease" as used herein refers to "a disease or disorder characterized or caused by inflammation." 'Inflammation' refers to a local response to cellular injury that is marked by capillary dilatation, leukocytic infiltration, redness, heat, and pain that serves as a mechanism initiating the elimination of noxious agents and of damaged tissue. The site of inflammation includes the lungs, the pleura, a tendon, a lymph node or gland, the uvula, the vagina, the brain, the spinal cord, nasal and pharyngeal mucous membranes, a muscle, the skin, bone or bony tissue, a joint, the urinary bladder, the retina, the cervix of the uterus, the canthus, the intestinal tract, the vertebrae, the rectum, the anus, a bursa, a follicle, and the like. Such inflammatory diseases include, but are not limited to, inflammatory bowel disease (IBD), rheumatoid diseases such as rheumatoid arthritis, fibrositis, pelvic inflammatory disease, acne, psoriasis, actinomycosis, dysentery, biliary cirrhosis, asthma, Lyme disease, heat rash, Stevens-Johnson syndrome, mumps, pemphigus vulgaris, and blastomycosis.

As used herein, the term "autoimmune disease" refers to "a disease or disorder resulting from an immune response against a self tissue or tissue component and includes a self antibody response or cell-mediated response." The term autoimmune disease, as used herein, encompasses organ-specific autoimmune diseases, in which an autoimmune response is directed against a single tissue, such as Type I diabetes mellitus, myasthenia gravis, vitiligo, Graves' disease, Hashimoto's disease, Addison's disease, autoimmune gastritis, and autoimmune hepatitis. The term autoimmune disease also encompasses non-organ specific autoimmune diseases, in which an autoimmune response is directed against a component present in several or many organs throughout the body. Such autoimmune diseases include, for example, systemic lupus erythematosus, progressive systemic sclerosis and variants, polymyositis, and dermatomyositis. Additional autoimmune diseases include, but are not limited to, pernicious anemia, primary biliary cirrhosis, autoimmune thrombocytopenia, Sjogren's syndrome, and multiple sclerosis.

The term "detectable moiety" or "imaging moiety" refers to a label that is attached to the compounds of the present invention for imaging a tumor, organ, or tissue in a subject. The imaging moiety can be covalently (or alternatively, non-covalently) attached to the compound. Examples of imaging moieties suitable for use in the present invention include, without limitation, radionuclides (e.g., $^{64}$Cu, $^{18}$F, etc.), biotin, fluorophores such as fluorescein, rhodamine, Texas Red, Cy2, Cy3, Cy5, or Cy5.5, Cy7, and their derivatives, antibodies, horseradish peroxidase, alkaline phosphatase, as well as derivatives and/or mixtures thereof.

As used herein, the term "linker" refers to "a moiety that possesses one or more different reactive functional groups that allows for covalent attachment of moieties such as a peptide to a chelating agent." Preferably, the linking moiety possesses two different reactive functional groups, i.e., a heterobifunctional linker. Suitable linkers include, without limitation, polymeric linkers, such as PEG, peptide linkers, carbon chain linkers, as well as those available from Pierce Biotechnology, Inc. (Rockford, Ill., USA.).

As used herein, "carrier" includes any solvents, dispersion medium, vehicle, coating, diluent, buffer, antibacterial and antifungal agent, isotonic and absorption delaying agent, carrier solution, suspension, colloids, or such like. The use of such delivery media for pharmaceutically active substances is well known in the art. Except insofar as any conventional media or agent is incompatible with the active ingredient, its use in the therapeutic compositions is contemplated. Supplementary active ingredients can also be incorporated into one or more of the disclosed liposome compositions.

The term "subject," as used herein, describes an organism, including mammals such as primates, to which treatment with the compositions according to the present invention can be provided. Mammalian species that can benefit from the disclosed methods of treatment include, but are not limited to, apes; chimpanzees; orangutans; humans; monkeys; domesticated animals such as dogs and cats; livestock such as horses, cattle, pigs, sheep, goats, and chickens; and other animals such as mice, rats, guinea pigs, and hamsters.

The term "treatment" or any grammatical variation thereof (e.g., treat, treating, and treatment etc.), as used herein, includes but is not limited to, alleviating a symptom of a disease or condition; and/or reducing, suppressing, inhibiting, lessening, ameliorating or affecting the progression, severity, and/or scope of a disease or condition.

The term "effective amount," as used herein, refers to an amount that is capable of treating or ameliorating a disease or condition or otherwise capable of producing an intended therapeutic effect.

In accordance with long standing patent law convention, the words "a" and "an" when used in this application, including the claims, denotes "one or more".

The terms "treatment," "treating," "treat" and the like are used herein to generally mean obtaining a desired pharmacologic and/or physiologic effect. The effect may be prophylactic in terms of completely, or partially, inhibiting or preventing a disease or symptom thereof and/or may be therapeutic in terms of a partial or complete stabilization or cure for a disease and/or adverse effect attributable to the disease.

The phrase "pharmaceutically-acceptable" refers to molecular entities and compositions that do not produce an allergic or similar untoward reaction when administered to a human, and in particular, when administered to the human eye. The preparation of an aqueous composition that contains a protein as an active ingredient is well understood in the art. Typically, such compositions are prepared as injectables, either as liquid solutions or as suspensions. Alternatively, they may be prepared in solid form suitable for solution in, or suspension in, liquid prior to injection. The liposome preparations may also be emulsified if needed.

As used herein, "pharmaceutically acceptable salt" refers to a salt that retains the desired biological activity of the parent compound and does not impart any undesired toxicological effects. Examples of such salts include, but are not limited to, acid addition salts formed with inorganic acids, for example, hydrochloric acid, hydrobromic acid, sulfuric acid, phosphoric acid, nitric acid, and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic (embonic) acid, alginic acid, naphthoic acid, polyglutamic acid, naphthalenesulfonic acids, naphthalenedisulfonic acids, polygalacturonic acid; salts with polyvalent metal cations such as zinc, calcium, bismuth, barium, magnesium, aluminum, copper, cobalt, nickel, cadmium, and the like; salts formed with an organic cation formed from N,N'-dibenzylethylenediamine or ethylenediamine; and combinations thereof.

The term "promoter," as used herein refers to a region or regions of a nucleic acid sequence that regulates transcription.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The term "vector," as used herein, refers to a nucleic acid molecule (typically comprised of DNA) capable of replication in a host cell and/or to which another nucleic acid segment can be operatively linked so as to bring about replication of the attached segment. A plasmid, cosmid, or a virus is an exemplary vector.

The term "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (1988).

The term "operably linked," as used herein, refers to that the nucleic acid sequences being linked are typically contiguous, or substantially contiguous, and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

EXAMPLES

The following example is included to demonstrate illustrative embodiments of the invention. It should be appreciated by those of skill in the art that the techniques disclosed in the example that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1 describes the use of IA as the parent compound to develop a bivalent near-infrared fluorescent imaging probe with carbon chain linker that selectively targeted integrin $\alpha_v\beta_3$. In vitro and in vivo results presented therein demonstrate illustrative uses of these probes for the detection of tumors.

In Example 2, IA 1 and IAC 2 were chosen as parent compounds for the bivalent ligand construction employing rational structure design using computer simulation. Since polyethylene glycol (PEG) has low toxicity and immunogenicity, and has good solubility in both aqueous and organic solvents, it has been used as a carrier for various drugs. These favorable physicochemical properties also make PEG a good linker material for constructing multivalent ligands. Example 2 describes the synthesis of bivalent ligand compounds (3) through (8) using PEG linkers of differing lengths to demonstrate the structure-function relationships via in vitro assays.

In Example 2, the synthesis and evaluation of a bivalent, non-peptide, small molecule integrin $\alpha_v\beta_3$ antagonist based on an in silico rational design approach is described. In particular aspects of the invention, near-infrared (NIR) fluorescent imaging probes have been developed for a variety of clinical uses, including, for example, the imaging of tumor angiogenesis. Improved receptor-binding affinity, improved receptor binding specificity of bivalent IA, and promising tumor accumulation of these NIR bivalent IA imaging probes have been demonstrated in exemplary murine tumor xenograft models.

Figures 1A, 1B:
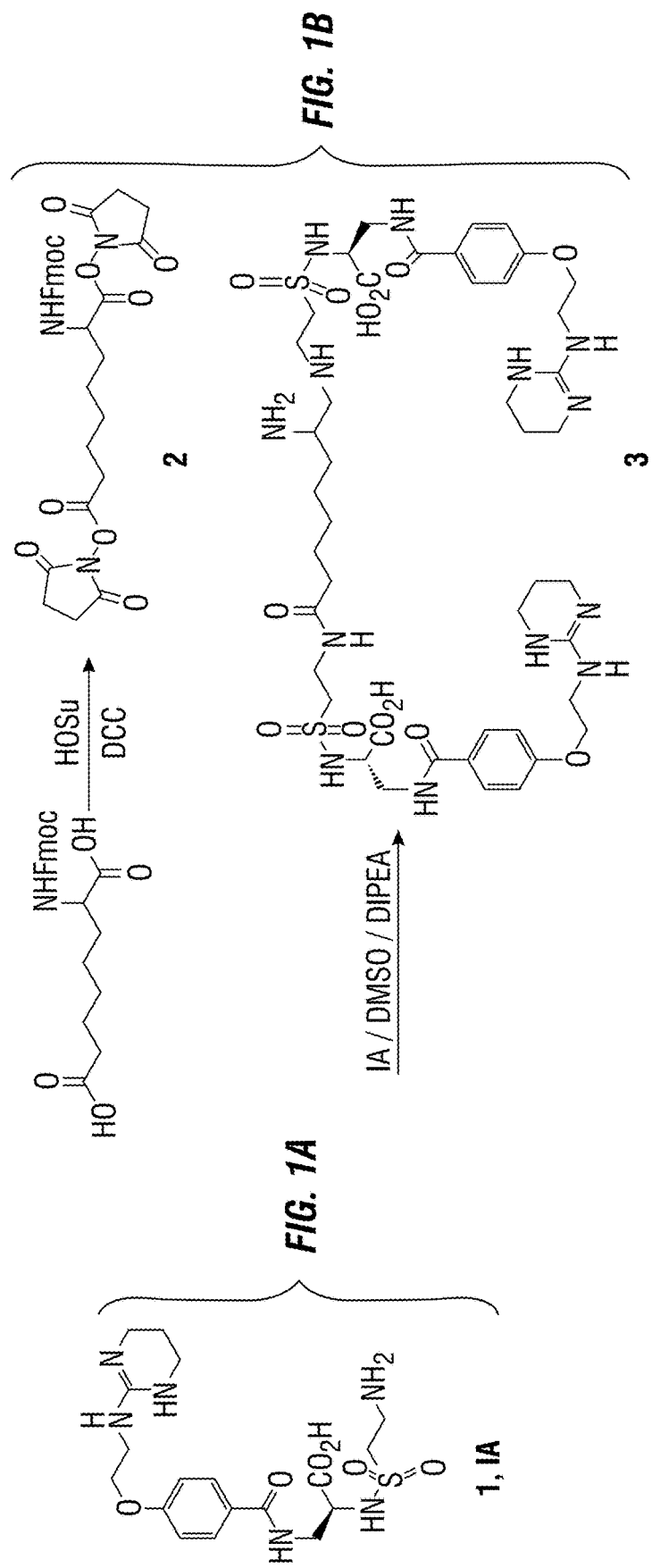
FIG. 1A illustrates the chemical structure of compound (1) IA in accordance with one aspect of the present invention.
FIG. 1B shows an illustrative synthetic reaction scheme of bivalent compound (3) IA in accordance with one aspect of the present invention.

Previously, the inventors developed an integrin $\alpha_v\beta_3$-targeting small molecular fluorescent probe derived from a small molecule $\alpha_v\beta_3$ antagonist, 4-[2-(3,4,5,6-tetrahydropyrimidine-2-lamino)ethyloxy]benzoyl-2-(S)-aminoethylsulfonyl-amino-h-alanine (FIG. 1, Compound IA). A polymerized liposome-based vascular targeted nanoparticle delivery system has also been developed using IA as tumor targeting ligand while carrying a payload for simultaneously imaging and therapy. In these studies, IA was used as a parent compound, and a bivalent ligand was constructed with a computer modeling-designed linker to enable multivalent ligands to mimic, compete with, or inhibit, natural Integrin interaction(s). The material used to link the parent ligands is an important design criterion, which would have a strong impact on the avidity and specificity of the ligands. Linker length and rigidities can affect the multivalent ligand-receptor interaction. In addition, the linkers used should have good physicochemical properties such as high stability and low toxicity. Hence, a carbon chain was chosen as the backbone of linkers and studied linkers with different lengths by computer simulation to predict the optimal structure for bivalent ligands followed by chemical synthesis and in vitro and in vivo validation (FIG. 1).

Considering binding that is more avid could improve the tumor targeting properties, NIR optical imaging probes have been developed based on the bivalent IA for tumor $\alpha_v\beta_3$ integrin imaging. The utilization of NIR probes in cancer imaging strategies has attracted wide attention because light scattering in tissue decreases with the reciprocal of the fourth power of wavelength and hemoglobin have minimal absorbance and autofluorescence in the NIR window. NIR imaging technology is relatively inexpensive and absent of the biological effects of radioactive probes. This invention describes the development of multivalent antagonists, including fluorescently-labeled (cyanine dye, Cy5.5) and radiolabeled, $\alpha_v\beta_3$ bivalent imaging probes (including, for example, bivalent and multivalent-IAs, such as IA-Cy5.5, and bivalent-IA-64Cu) that demonstrated strong and specific binding. In exemplary embodiments, the resulting bivalent-IA-Cy5.5 imaging probe has demonstrated significant potential for the early detection of tumors and micrometastatic lesions.

Example 1—Synthesis and Evaluation of a Near-Infrared Fluorescent Non-Peptidic Bivalent Integrin $\alpha_v\beta_3$ Antagonist for Cancer Imaging In this example, multivalency in IA was shown to improve its therapeutic value beyond the simple addition of the extra binding sites. Linking the therapeutic molecules together resulted in a synergistic increase in efficacy that was greater than what would be achieved by the increase in the pharmacological dose alone. These comparisons were based on equivalent pharmacological doses, which were defined as the total number of pharmacophore, that is, 1 per molecule for the monomer, 2 per molecule for the dimer and 3 per molecule for the trimer. Docking and molecular dynamics were employed to explore the binding modes of IA monomer, dimer and trimer and the therapeutic efficacy of constructed multivalent IA was evaluated using B16F10 tumor bearing mice. This is the first report on integrin αvβ3 multivalent ligands that demonstrated significant and unambiguous enhanced therapeutic efficacy as compared to the parent monovalent compounds.

Computer modeling approaches to identify new inhibitors are essentially a very sophisticated and efficient way to design drugs. In this study, a bivalent non-peptide intergrin $\alpha_v\beta_3$ antagonist (bivalent IA) has been synthesized based on the in silico rational design approach. A NIR fluorescent imaging probe has been developed from this bivalent compound. In vitro binding assays have shown that the bivalent IA ($IC_{50}$=0.40±0.11 nM) exhibited improved integrin αvβ3 affinity when compared to the monovalent IA ($IC_{50}$=22.33±4.51 nM), resulting in an over 50 fold improvement in receptor affinity. NIR imaging probe, bivalent-IA-Cy5.5 conjugate also demonstrated significantly increased binding affinity ($IC_{50}$=0.13±0.02 nM). Fluorescence microscopy studies showed integrin-mediated endocytosis of bivalent-IA-Cy5.5 in U87 cells, which was effectively blocked by non-fluorescent bivalent IA. Tumor accumulation of this NIR imaging probe was also demonstrated in U87 mouse xenografts.

Experimental Procedures

General, All solvents and reagents were purchased from commercial sources and used without further purification. $^1$H NMR and $^{13}$C NMR were obtained on a Bruker BioSpin Corp. Ultrashield™ at 300 and 75 MHz, respectively. Chemical shifts were reported in ppm (δ) downfield of tetramethylsilane and coupling constants were given in Hertz. The purification of the crude product was carried out on a semipreparative reversed-phase high performance liquid chromatography (HPLC) system equipped with a diode array UV-Vis absorbance detector (Agilent 1200 HPLC system, Santa Clara, Calif., USA). Mass spectral data were recorded on a ThermoFinnigan LCQ™ Fleet (San Jose, Calif., USA) using electrospray as the ionization method. U-87 glioblastoma cells were obtained from American Type Culture Collection (Manassas, Va., USA) and were grown in Dulbecco's Modification of Eagle's Medium (DMEM) supplement with 10% fetal bovine serum (FBS) at 37° C. in a humidified atmosphere.

Docking

The docking experiment was performed using Glide in Maestro (Schrödinger, MA). The center of grid-enclosing box is defined by the geometrical center of cyclic RGD ligand (cRGD) in crystal 1L5G. The scaling factor was set to 0.8 for the receptor atoms, with partial atomic charge of 0.25 as the maximum, to keep the protein relatively flexible and the standard precision (SP) parameter set was applied in all the docking experiments. The binding poses were selected by the ranking of scoring only when two criteria—the carboxylate group in the ligands forms coordination bonds (mimicked by electrostatic interactions in docking) with Mn2+ ions in the binding site; and the 2-amine-tetrahydropyrimidine group forms hydrogen bonds with Asp-218 as the guanidine side chain of arginine does in the native ligand are satisfied.

Molecular Dynamics (MD) Simulation

To better understand the interactions between the ligands (IA monomer, dimer and trimer) and the receptor (integrin α$_v$β$_3$), the top-ranking poses from the docking were further simulated and the molecular dynamics were performed using Amber 11 (Case et al., 2010). In the simulation, the protein is truncated to keep only the domains near the active site, by removing residues 441-956 in αv subunit and residues 55-108 and 354-690 in β$_3$ subunit, to balance the computational cost and precision. The charge at the atoms of all ligands was computed at the level of B3LYP/cc-pVTZ// HF/6-31G* with Gaussian 09 structure calculation software (Dupradeau et al., 2010) (Gaussian, Wallingford, Conn., USA) and assigned using RED (RESP ESP charge Derive) (Cieplak et al., 1995). TLEaP in Amber 11 suite was used to solvate the systems in a truncated-octahedral box of TIP3P water molecules (Jorgensen et al., 1983) with the minimum distance of 10 Å from the solutes to the box faces while Na+ ions were added to neutralize these systems. Amber ff03 force field (Duan et al., 2003) and General Amber force field (GAFF) (Wang et al., 2004) were used for protein and ligands, respectively. The Mn2+ ions near the active site were also included, with a full +2 charge assigned and a non-bonded approach employed, in which the coordinating acidic amino acid were deprotonated. The Bradbrooks's non-bond parameters for Mn2+ were applied with a Lennard-Jones potential of ∈=−0.014 kcal/mol and r0=1.69 Å (Bradbrook et al., 1998). The SHAKE algorithm was used to constrain all bonds involving hydrogen (Ryckaert et al., 1977). These models were further extended using the periodic boundary condition. A 10.0-Å cutoff was applied for nonbonding interactions. The Particle Mesh Ewald method was employed to treat the long-range electrostatic interactions (Darden et al., 1993). The binding free energies of IA ligands to integrin αvβ3 were estimated using Generalized Born/Surface Area (GB/SA) and Poisson Boltzmann/Surface Area (PB/SA) models (Honig and Nicholls, 1995; Kollman et al., 2000).

Computer Modeling. The AutoDock program (version 3.0.5) was used for docking calculations. (Morris et al., 1998). The graphical program SYBYL (version 16.91, Tripos, Inc. (St. Louis, Mo., USA) was used for model building of the ligand structures, to generate missing hydrogen atoms and assign partial charges for protein targets used in AutoDock runs, and for energy minimization of initial ligand structures. Structural figures were generated using WebLab Pro (Madison, Wis., USA).

Protein Coordinates. The structure of extracellular segment of integrin □v□3 (PDB entry 1jv2) was used for the docking simulations of integrin □v□3. The extracellular segment of the human integrin structure contains two subunits alpha (957 residues) and beta (692 residues). When complexed with Arg-Gly-Asp (RGD), the □v□3 revealed that the pentagonal peptide inserted into a crevice between the propeller and □A domains on the integrin head (Debaldo et al., 2008). This RGD sequence makes the primary contact area with the integrin, and each residue participates extensively in the interaction, which are completely buried in the protein interior. For the simulations, subunit □□ was selected, and Glu220, Asn215, Asp217, Pro219 were used as the target coordinates for binding as they are in close contact with RGD. No water molecules were included. SYBYL was used to add essential hydrogens, and to assign partial charges from the Kollman united-atom force field to the target protein.

Ligand Coordinates. The structures of bivalent-IA-Cy5.5 were built in SYBYL Biopolymer software package and energy minimized with MMFF94 force-field by 100 steps. The orientation of each ligand was overlaid onto the integrin □v□3 in the crystal structure to allow similar starting coordinates to be identified. Prior to docking runs, all ligand structures were translated arbitrarily 30 Å from the surface of the □v□3. Because these ligands were highly flexible with multiple rotatable dihedrals present (even in the monovalent system), a two-stage strategy for protein:ligand complex structure modeling was adopted, which involved simulated annealing (SA) and rigid docking, that partially takes into account ligand flexibility. In the SA step, a 1-ns MD trajectory was generated for each ligand at a temperature of 1500° K. Structures saved every 1 ps underwent energy minimization and the optimized structures were sorted by energy. At this stage, the conformational analysis was approximate, as a crude solvation model was employed, with interactions with solvent described by introducing a distance-dependent dielectric constant.

Simulation of Substrate Binding Using AutoDock. The auxiliary program AutoGrid (Scripps Research Institute, La Jolla, Calif., USA) was used for generation of affinity grid fields. The program assigned the center of the grids automatically. The dimensions of the grid were 60.0 Å×60.0 Å×60.0 Å with grid points separated by 0.375 Å. The ligands were then docked using the Lamarckian Genetic Algorithm (LGA). The parameters for the LGA configurational search were identical for all docking jobs. Ligand flexibility was taken into account by including rotations around bivalent-IA-Cy5.5 single bonds in the conformational search. The maximum translation step was kept constant at 0.2 Å for every cycle, but the maximum quaternion rotation step and dihedral rotation step had a reduction factor of 0.99 per cycle starting from a maximum rotation of 5.0°. For the search to be extensive, the program uses a multiple starting approach in combination with a time dependent random number generator. The number of runs was set as 10.

For each run, a population of 50 individuals was used, with at most 250,000 function evaluations used and run for at most 27,000 generations. The first top individual was preserved each generation. The mutation rate was 0.02 and the crossover rate 0.80. The GA's selection window was 10 generations; the alpha parameter was set to 0. After docking simulations had been carried out, the 10 solutions produced were grouped into clusters such that the ligand tins deviations within each cluster were below 0.5 Å. The clusters were also ranked by the value of the lowest energy solution within each cluster. The lowest energy solution and the solutions with energies within 5 kcal/mol of this value were considered as possible binding models.

Bivalent Ligands Synthesis. Bivalent ligand 3 was synthesized in three-steps (FIG. 1): To a solution of the 2-(((9H-fluoren-9-yl)methoxy)carbonylamino)octanedioic acid (100 mg, 0.24 mmol) in EtOAc (20 mL), Dicyclohexylcarbodiimide (110 mg, 0.53 mmol) and N-hydroxysuccinimide (60 mg, 0.52 mmol) were added at 0° C. The mixture was stirred at 0° C. for 8 hr (detected by TLC). Solvent was evaporated under reduced pressure to get the crude intermediate compound (2). Compound (2) was dissolved in DMSO (9 mL) for next step reaction without further purification. To this DMSO solution, IA (250 mg, 0.50 mmol) and diisopropylethylamine (0.2 mL, 1 mmol) were added and the mixture was stirred at ambient temperature for 24 hr. After removing solvent at reduced pressure, 10 mL of water was added and the white solid was removed by filtration. The aq. solution was lyophilized and the residue was re-crystallized in methanol and acetone (1:3) to give pure bivalent IA 3 with 50% yield as white solid. 1H NMR (300 MHz, D2O): 7.65 (m, 4H), 6.93 (m, 4H), 4.16 (m, 7H), 3.84 (m, 4H), 3.30 (m, 10H), 3.21 (m, 10H), 2.047 (t, 2H, J=7), 1.80 (m, 6H), 1.43

(m, 2H), 1.18 (m, 4H). MS (electrospray): m/z 1066.3 (100, [M+1]+, calculated: 1065.4.); 533.8 ([M+2H]2+, calculated: 533.7.).

Figure 2:
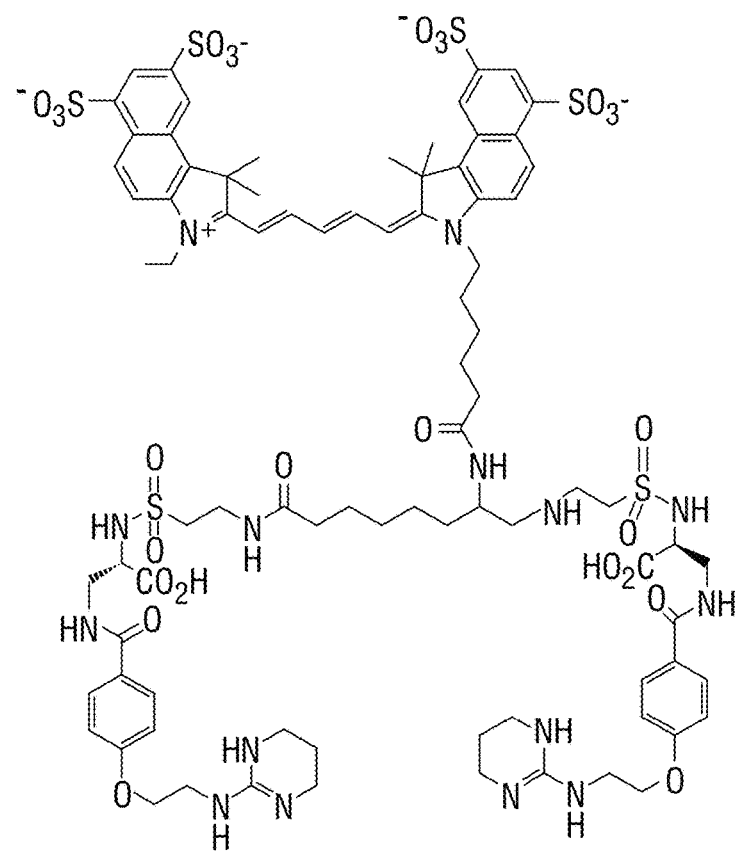
FIG. 2 illustrates the chemical structure of bivalent-IA-Cy5.5 conjugate in accordance with one aspect of the present invention.

Bivalent-IA-Cy5.5 Conjugate Synthesis. Bivalent IA 3 (1.5 mg, 1.4 µmol) and 1.2 equiv of Cy5.5-NHS (2.0 mg, 1.7 µmol) was dissolved in 1 mL DMSO, then 0.1 mL triethylamine was added (FIG. 2). The reaction mixture was stirred in the dark at ambient temperature overnight and then quenched by adding 200 µL of 5% acetic acid (HOAc). The crude product was purified by a semipreparative reversed-phase HPLC employing a Phenomenex Luna™ (Torrance, Calif., USA) C18 column (250 mm×10 mm) with the mobile phase starting from 95% solvent A (0.05% ammonia acetate in water) and 5% solvent B (acetonitrile) to 40% solvent A and 60% solvent B at 30 min and the flow rate was 4 mL/min. Fractions containing bivalent-IA-Cy5.5 conjugates were collected, lyophilized, re-dissolved in saline at a concentration of 1 mg/mL, and stored in the dark at −20° C. until use. The analytical HPLC method was performed with the same gradient system, but with a Phenomenex C18 column (250 mm×4.6 mm), and flow rate of 1 mL/min. The purity of Cy5.5-labeled bivalent IA was over 98% from analytical HPLC analysis. The yield of bivalent-IA-Cy5.5 conjugate was over 70%. The purified bivalent-IA-Cy5.5 conjugate was characterized by mass spectroscopy (MS). MS (electrospray): m/z 1965.7 ([M+H]+, calculated: 1965.2.); 983.1 (100, [M+2H]2+, calculated: 983.6.). The absorption and fluorescence emission characteristics of bivalent IA-Cy5.5 conjugates were identical to those of free Cy5.5, as apparent from the spectrums measured in H2O.

U-87 MG Xenograft Model, Animal procedures were performed according to approved protocols. Female athymic nude mice (nu/nu), obtained from Charles River Laboratories, Inc. (Cambridge, Mass., USA) at 4-6 weeks of age, were injected subcutaneously in the right rear thigh with 1×10^7 U-87 MG cells suspended in 100 µL of phosphate-buffered saline (PBS). The cancer cells were harvested from sub-confluent cultures with 0.25% trypsin. Trypsinization was stopped with DMEM containing 10% FBS, after which the cells were washed once in serum-free medium and resuspended in PBS. Trypan blue exclusion was performed to ensure >90% cell viability. The tumor bearing mice were subjected to in vivo imaging studies when the tumors reached 0.4-0.6 cm in diameter.

In vitro Binding Assay. To determine the receptor-binding ability, the bivalent ligands were tested for their ability to competitively inhibit the attachment of the natural ligand vitronectin to purified human αvβ3 by Enzyme-Linked Immunosorbent Assay (ELISA). Purified integrin αvβ3 protein (Chemicon International, Temecula, Calif., USA) was applied to 96-well polystyrene microtiter plates at 0.1 µg/well. After overnight incubation at 4° C., the plates were washed, and then blocked with milk solution (KPL, Inc. Gaithersburg, Md., USA) at room temperature for 2 hr. The blocking buffer was removed, and the plates were inoculated in quadruplicate with bivalent IAs with a typical starting concentration of 125 nM. Serial dilutions were prepared in the 96-well plates using multichannel pipettes. Biotinylated vitronectin solution (0.1 µg/well) was added to each well as a standard competitor. The plates were incubated at room temperature for 3 h, washed, and the bound vitronectin was detected using NeutrAvidin-HRP conjugate at 0.01 µg/well (Pierce, Rockford, Ill., USA) and LumiGlo® chemiluminescent substrate system (KPL, Inc.). The luminescence was read using a FLUOstar™ OPTIMA Microplate Reader (Durham, N.C., USA). The concentration of inhibitor producing 50% inhibition (IC50) of vitronectin binding to αvβ3 was calculated based on a curve fitting model using Kaleida-Graph 3.5 (Synergy Software, Reading, Pa., USA). c-[RGDfV] (Peptides International, Inc., Louisville, Ky., USA) was also tested using the same method as described above.

Fluorescence Microscopy Studies. To demonstrate that the bivalent-IA-Cy5.5 imaging probe could act as a specific ligand for αvβ3 integrin receptor in living cells, and to demonstrate the binding and sub-cellular localization of the bivalent probe, U-87 MG (ATCC HTB-14), a human glioblastoma cell line known to over-express integrin αvβ3, was used in a probe binding assay (Debaldo et al., 2008). For fluorescence microscopy studies, 1×10^4 U-87 cells were cultured on 35 mm MatTek glass bottom culture dishes. After 24 hr, cells were washed with PBS and then incubated with bivalent-IA-Cy5.5 (200 nM) at 37° C. for 45 min. Integrin specificity of the probe binding was verified by incubating U-87 cells with and without a blocking dose of the non-fluorescent bivalent IA (20 µmol/L). After the incubation period, the cells were washed three times with ice-cold PBS. The fluorescence signal of the cells was recorded using FluoView® 1000 Laser Scanning Confocal Microscope (Olympus, Center Valley, Pa., USA) under a 40× oil-immersion objective, with laser excitation at 675 nm (Cy5.5). A differential interference contrast image was also recorded so that the origin of fluorescent signals could be confirmed.

In vivo Fluorescence Imaging of Tumors. ∼3×10^6 U-87 cells were implanted bilaterally in the posterior flanks of immunocompromised (nu/nu) mice and grown to ∼4 to 6 mm in diameter. Imaging was carried out in groups of five mice. After palpable masses were detected, animals were manually restrained and imaging probes were intravenously administered (lateral tail vein) using a 30-Ga needle via aseptic technique. Free Cy5.5 was prepared by dissolving the same Cy5.5NHS ester used for labeling the bivalent IA (GE Healthcare, Piscatway, N.J., USA) in phosphate buffered saline (PBS), pH 7.4 overnight at 4° C. Stock concentration of free Cy5.5 was measured optically using the molar extinction coefficient of 250000M-1 cm-1 using a UV-visible spectrophotometer at the maximum absorbance wavelength (675 nm) as recommended by the manufacturer. The bivalent-IA-Cy5.5 was weighed and confirmed by spectrophotometric measurement. Appropriate dilutions of each probe were made in PBS, pH 7.4, and each was filter sterilized (0.2-µm) immediately prior to use. All animals weighed between 18 and 20 g, and each received 10 nmol of imaging probe (in a total volume of 100 µL). Fluorescence imaging was performed with a small animal-dedicated optical imaging system (Xenogen/Caliper IVIS-200, Mountain View, Calif., USA) under continuous 1.5-2.0% isoflurane delivered through the integrated anesthesia nosecone system. At 2-, 4-, 7-, 24-, and 48-hrs' post-injection, images were acquired with the surface of the tissue of interest (tumor) approximating a perpendicular viewing angle relative to the camera line of sight; this viewing angle was also used for normal tissue selection.

For determining tumor contrast, mean fluorescence intensities of the tumor area (T) defined as radiance (photons/sec/cm2/sr) at the right rear leg of the animal and of the area (N) at the right flank (normal tissue) were calculated by region-of-interest (ROI) analysis using the corresponding photograph of each image acquisition dataset to identify the tumor region. Pre-injection imaging was also performed to determine baseline autofluorescence. For competitive inhibition studies, mice (n=3) were co-injected with 500 nmol bivalent IA and 10 nmol of imaging probe (bivalent-IA- Cy5.5) following the same procedure described above. Free Cy5.5 studies were performed in the same manner following the intravenous injection of 10 nmol. For ex vivo biodistribution imaging, two tumor-bearing mice were imaged 24 hrs post injection of bivalent-IA-Cy5.5 and thereafter euthanized per IACUC protocol (CO2 and cervical dislocation). Tumor and major internal organs (heart, lung, liver, spleen, gastrointestinal tract, and kidneys) were harvested, weighed, and imaged against a black paper background. All image acquisition parameters were as follows: epi-illumination; Cy5.5 Em/Ex; Bin: (HR)4, FOV: 12.9; f2; 0.2 sec.

Data Processing and Statistics. All data are given as means±SD of n independent measurements. Statistical significance was assigned for P values<the boundaries of tumors. Quantitative data was acquired with the software provided from the instrument's manufacturer (Living Image Statistics Software package (v3.1) R Development Core Team, R: A language and environment for statistical computing. R Foundation for Statistical Computing, Vienna, Austria. ISBN 3-900051-07-0).

Chemical Methods—Synthesis of IA Dimer

To a solution of the 2-((($^9$Hfluoren-9-yl)methoxy)carbonylamino)octanedioic acid (100 mg, 0.24 mmol) in EtOAc (20 mL), dicyclohexylcarbodiimide (110 mg, 0.53 mmol), and N-hydroxysuccinimide (60 mg, 0.52 mmol) were added at 0° C. The mixture was stirred at 0° C. for 8 hr (detected by TLC). Solvent was evaporated under reduced pressure to get the crude intermediate. The intermediate was dissolved in DMSO (9 mL) for next step reaction without further purification. To this DMSO solution, IA (250 mg, 0.50 mmol) and diisopropylethylamine (0.2 mL, 1 mmol) were added and the mixture was stirred at ambient temperature for 24 hr. After removing solvent at reduced pressure, 10 mL of water was added, and the white solid was removed by filtration. The aq. solution was lyophilized, and the residue was recrystallized in methanol and acetone (1:3) to give pure bivalent IA 3 with 50% yield as white solid. $^1$H NMR (300 MHz, D2O): 7.65 (m, 4H), 6.93 (m, 4H), 4.16 (m, 7H), 3.84 (m, 4H), 3.30 (m, 10H), 3.21 (m, 10H), 2.05 (t, 2H, J) 7.0 Hz), 1.80 (m, 6H), 1.43 (m, 2H), 1.18 (m, 4H). MS (electrospray): m/z 1066.3 (100, [M+H]$^+$, calculated 1065.4.).

Synthesis of IA Timer

Triethylamine (4.0 mL, 28 mmol) was added to a stirred solution of triethanol amine (0.45 g, 3 mmol) in anhydrous CH$_2$Cl$_2$ (50 mL). 1,1'-carbonyldiimidazole (CDI, 4.06 g, 24 mmol) was added and the mixture was stirred at room temperature for 12 hr and the reaction was quenched by adding 50 mL water. The organic phase was separated and dried over MgSO$_4$. Solvent was evaporated under reduced pressure to get the crude intermediate 2,2',2"-nitrilotris (ethane-2,1-diyl)tris($^1$H-imidazole-1-carboxylate) (1.16 g, 2.69 mmol, 90%) as a colorless oil. IA (100 mg, 020 mmol) was added to a solution of 2,2',2"-nitrilotris(ethane-2,1-diyl) tris(1H-imidazole-1-carboxylate) (30 µL, 0.03 mmol) in DMSO (2 mL). Triethylamine (0.1 mL, 0.70 mmol) was added and the mixture was stirred overnight in the ambient temperature, the reaction was quenched by adding 200 µL of trifluoroacetic acid (TFA). The purification of the crude product was carried out on a HPLC. The peak containing the IA trimer was collected, lyophilized and stored in the dark at −20° C. until use. 1H NMR (500 MHz, D$_2$O): 7.55 (d, 6H, J=8.4), 6.81 (d, 6H, J=8.4), 4.20 (m, 8H), 3.99 (m, 6H), 3.70 (m, 3H), 3.37 (m, 22H), 3.16 (t, 6H, J=6), 3.13 (m, 12H), 1.70 (m, 6H). The ms spectrum of IA trimer: m/z 1596.4 ([M+H]$^+$, calcd 1595.6).

Computational Methods—Protein Preparation

Figure 3A:
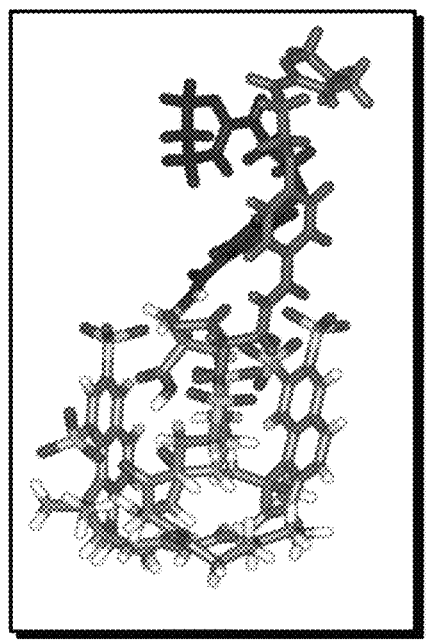
FIG. 3A and FIG. 3B schematically illustrate the lowest-energy conformation of bivalent-IA-Cy5.5 conjugate (FIG. 3A) and interaction of bivalent-IA-Cy5.5 with integrin (FIG. 3B). The lowest-energy conformation was obtained from the analysis of molecular dynamics trajectories. The integrin structure was obtained from the open form of the integrin crystal structure (1JV2)

The crystal structure (PDB ID: 1L5G) of integrin $\alpha_v\beta_3$ (*Homo sapiens*) in complex with cyclic ARG-GLY-ASP peptide (cRGD) was retrieved from the Protein Data Bank (www.pdb.org) (Xiong et al., 2002) as the initial geometry in protein preparation. The "Protein Preparation Wizard" workflow in Maestro (version 9.2) was employed to simulate and add missing residues, assign atom types, saturate heavy atoms with hydrogens, and rationalize the hydrogen positions by potential energy minimization with the convergence of 0.3 Å. The Mn$^{2+}$ ions and glycosylation modifications were kept during the receptor model building for docking of IA ligands. As shown in FIG. 2, FIG. 3A and FIG. 4A, cRGD is well buried into a pocket across the interface between $\alpha_v$ and $\beta_3$ subunits. The guanidinium of the arginine terminal forms a strong salt bridge, containing multiple H-bonds, with the carboxylate of Asp-218 in the $\alpha_v$ subunit while the carboxylate of the aspartate terminal coordinates to Mn$^{2+}$ and H-bonds to the backbone amide of Asn-215 in $\beta_3$ subunit. Besides, the backbone amide of the terminal aspartate forms an H-bond with the backbone carbonyl of Arg-216 in $\beta_3$ subunit. These strong interacts enhances the binding of cRGD to integrin $\alpha_v\beta_3$ and increases the rigidity in the ligation, and certainly determines the binding pose of cRGD on this protein.

Ligand Preparation

IA monomer, dimer and trimer were built by the "Sketch molecule" module in Maestro (version 9.2). Then the structures were submitted to LigPrep to minimize potential energy and generate the stereoisomers, tautomers, ring conformations, and protonation states that correspond to pH ranging from 5.0 to 9.0. The chirality of IA unit was retained during the conformation generation. OPLS_2005 force field was assigned to all atoms in the IA molecules, and Epik 2.2 module was used as the predictor for pK$_a$ in the ligand preparation.

Molecular Dynamics (MD) Simulation

For each system, energy minimization was executed by the steepest descent method for the first 2000 steps and followed by the conjugated gradient method for another 2000 steps with a 2 kcal/mol Å$^2$ restraint on all atoms of the protein and ligand. The temperature was increased from 0 to 300 K in 20 ps with a 2 kcal/mol Å$^2$ restraint on the solutes and then the force constant was changed to 1 kcal/mol Å$^2$ for the following 30 ps using the isothermal-isobaric (NPT; 1 atm and 300° K) ensemble to relax the water molecules and ions. The temperature of the systems was controlled by Langevin thermostat (Izaguirre et al., 2001). The ligand was restrained with the force constant of 1 kcal/mol Å$^2$ for 200 ps in the simulation for the dimer and trimer-binding systems. Then equilibrating calculation was executed at 1 atm and 300° K using the NTP ensemble to obtain a 3-ns trajectory. The analysis of potential energy and protein backbone RMSD indicate the stability of the three systems during the simulation. The potential energies of the systems remain constant after 1.5 ns while RMSDs increase to 1.5 Å in 500 ps and then oscillate between 1.5 to 1.8 Å. Finally, the last ns of the 3-ns productive trajectory was extracted for structural analysis and binding free energy calculation, including Generalized Born/Surface Area (GB/SA) and Poisson Boltzmann/Surface Area (PBSA). For the free energy calculation, snapshots were extracted from the 1-ns trajectory with time interval of 20 fs. In total, 50 frames were taken to compute binding free energy for each system.

In Vitro Binding Assay

To determine the receptor-binding ability, the multivalent ligands were tested for their ability to competitively inhibit the attachment of the natural ligand vitronectin to purified human $\alpha_v\beta_3$ by enzyme-linked immunosorbent assay (ELISA) described previously (Li et al., 2010). Briefly, purified integrin $\alpha_v\beta_3$ protein (Chemicon International, Temecula, Calif., USA) was applied to 96-well polystyrene microtiter plates for overnight incubation at 4° C. The plates were washed and then blocked with milk solution (KPL, Inc., Gaithersburg, Md., USA) and the plates were inoculated in quadruplicate with multivalent IAs at different concentrations. Biotinylated vitronectin solution was added to each well as a standard competitor. The plates were incubated at room temperature, washed, and the bound vitronectin detected using NeutrAvidin-HRP® conjugate (Pierce, Rockford, Ill., USA) and LumiGlo® chemiluminescent substrate system (KPL, Inc., Gaithersburg, Md., USA). The luminescence was read using a FLUOstar® OPTIMA Microplate Reader (Durham, N.C., USA). The concentration of inhibitor producing 50% inhibition ($IC_{50}$) of vitronectin binding to $\alpha_v\beta_3$ was calculated based on a curve-fitting model using KaleidaGraph® 3.5 (Synergy Software, Reading, Pa., USA).

In Vitro Cytotoxicity Assay

For cell cytotoxicity assay, the cells were then seeded into 96-well flat-bottomed tissue-culture plates at $1\times10^4$ cells/well and incubated for 24 hr in humidified atmosphere of 5% (vol./vol.) $CO_2$ at 37° C. in the presence of each compound. The multivalent compound (monomer, dimer, and trimer) sample solutions were diluted with culture medium (1% FBS added) to obtain concentrations in the range of 0.1-100 μg/mL for each compound. The cytotoxic effects of monomer, dimer and trimer compounds were evaluated by adding 100 μL of each sample in 100 μL culture medium to each well. After 24-hrs' incubation, cell viability was evaluated by mitochondrial conversion of 3-(4,5-dimethylthiazol-2-yl)-2,5-diphenyl tetrazolium bromide (MTT assay) (Allison et al., 1985).

Anti-Angiogenic In Vitro Assay

The impact of IA derivatives on capillary-like tube formation by HUVECs was investigated. In vitro endothelial tube formation was performed as described in the literature (Park et al., 2007). Growth factor reduced Matrigel® (100 μL, BD Bioscience, San Jose, Calif., USA) was added to each well of a 96-well plate and allowed to polymerize for 30 min at 37° C. HUVECs were suspended in medium at the density of $4\times10^5$ cells per milliliter, and 100 μL of the cell suspension was added to each Matrigel-coated well in the presence of IA monomer, dimer and trimer. Cells were incubated at 37° C. for 6 hr, and then photographed at 20× magnification using a Micromaster® phase contrast microscope (Fisher Scientific, Pittsburgh, Pa., USA). The branch points were counted and averaged.

In Vivo Antitumor Efficacy of Multivalent IAs

All animal procedures were approved by appropriate Animal Care and Use Committee. The therapeutic test for antitumor efficacy of IA multivalent compounds was evaluated using tumor-bearing mice, which were prepared by bilateral subcutaneous injection in the thighs of nu/nu female mice (6 weeks old; 20-25 g). The mouse melanoma cancer cell line B16F10 was obtained from Caliper and tested negative for rodent pathogens. The cells were maintained in vitro as described above. The mice were inoculated with suspensions of $1\times10^6$ B16F10 cells in 100 μL complete medium (10% FBS added). Three days after subcutaneous inoculation (the tumor diameter was approximately 3-5 mm, the tumor volume was approximately 50 to 100 $mm^3$), tumor-bearing mice (n=7 per group) were injected intraperitoneally (i.p.) with each IA compound (monomer, dimer, or trimer) in PBS or PBS alone for control group. All compounds were serially diluted with PBS, and were given 2 times per day (every 12 hr) at a dose of 100 μL of 7.5, 15, 30 mg/kg per injection for 14 days. This dosing regimen was chosen to be comparable to the clinical trial usage for RGD (Gilbert et al., 2011; Nabors et al., 2012), and was used for all three compounds, resulting in equivalent pharmacophore. This study design was deliberately chosen to highlight the effect of multivalency. The tumor size was calculated as $a\times b^2/2$, where 'a' is the largest and 'b' the smallest diameter. In addition, the weight of the mice and the tumors were recorded after harvesting.

Data Analysis and Statistics

A tumor growth model was used to isolate and interpret the effects of pharmacological dose (pharmacophore) and multivalency. This was done using the R software package 'geepack' (Højsgaard et al., 2006; Team et al., 2012). The tumor burden (sum of the volumes of left and right tumors) for each animal was first normalized by dividing by the starting volume on the first day of treatment, then taking the logarithm to linearize the data. The pharmacological dose was decoupled from the molecular valency, N, for this model by defining the pharmacophore or pharmacological dose (PD) as PD=N×MD, where MD is the molar dose. The pharmacological excess (compared to monomer) dose (ED) due to multivalency is then: ED=PD-MD=MD×(N−1). The data was fit to a linear model:

$$\ln\left(\frac{V}{V_0}\right) = A \times \text{day} + B \times PD \times \text{day} + C \times ED \times \text{day}$$

where 'day' is the day after starting treatment, PD is the pharmacological dose, and ED is the valency; V is the tumor burden on 'day' and $V_0$ is the initial tumor burden. The R function geeglm can then be used to evaluate the coefficients A, B, and C. The logic of this model is that if the effects of multivalency are related only to the raw increases in numbers of binding units, then C~0. If C>0, multivalency (ED>0) increases tumor growth; if C<0 it decreases tumor growth. If C~−B, the multimer has no therapeutic benefit beyond that of the monomer. In evaluating confidence intervals and statistical significance, repeated measures on the same animals over time is accounted for when using the geeglm.

Statistical analysis of all in vitro studies was performed using two-way ANOVA. Significance between groups was calculated using TukeyHSD with a confidence level of 095.

Results

Computer Modeling.

From calculations of binding energies and ligand spatial distributions, the prediction of favored protein-ligand binding modes, interaction strengths, and binding specificity can be obtained with AutoDock simulations. Ten (10) Lamarckian genetic algorithm (LGA) docking runs were performed for each protein-ligand pair, with each run producing one possible binding mode or solution. The solutions were first sorted in terms of the binding mode, i.e., the position and orientation of the ligand relative to the protein target. The solutions were clustered based on root mean square (rms) deviations in ligand atomic positions, with structures with rmsd of less than 0.5 Å grouped into a cluster. The total number of generated low-energy clusters measures the specificity of binding. A small number of clusters indicated that the ligand had only a few possible binding modes and interacted with a specific site (or sites) on the target protein. On the other hand, a large number of clusters implied existence of a wide range of binding modes and a lack of specific ligand-target interactions.

The second step in sorting solutions involves identification of the solution of lowest binding energy within each cluster and ranking the different clusters according to this energy value. The solution with the lowest energy in the top-ranked cluster and all solutions with energies higher by up to 5.0 kcal/mol were considered as possible binding modes for ligand to target.

Docking of Bivalent-IA-Cy5.5 to the Integrin $\alpha_v\beta_3$.

Figure 3B:
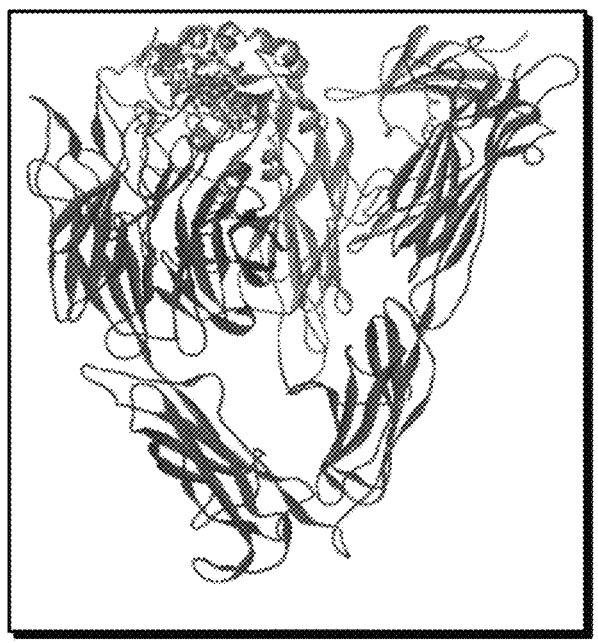

A summary of the AutoDock results is presented in Table 3; the docked structures of the first and second clusters are shown in FIG. 3. The docking of bivalent-IA-Cy5.5 to the Integrin $\alpha_v\beta_3$ produced 3 clusters out of 10 runs. There were 5 solutions in the first cluster with an average docking energy of −34.04 kcal/mol. The binding site defined by this cluster is in the cleft between the RGD binding domain in Integrin $\alpha_v\beta_3$. It was observed that bivalent-IA-Cy5.5 stays at that site in the presence of the whole protein. This cluster presents the best model for a possible bivalent-IA-Cy5.5 interaction to the Integrin $\alpha_v\beta_3$. A comparison of the AutoDock results suggest that this binding conformation corresponding to the linker length of the bivalent-IA-Cy5.5 is a better substrate of Integrin $\alpha_v\beta_3$. The binding of bivalent-IA-Cy5.5 to the protein is stronger (lower energy) and more specific (small number of clusters) compared to other conformations with different linker length. The microscopic reason for these effects appears to be a lack of fit between different Cy5.5 conformation and the inhibitor/substrate binding site. The docking results are approximate. The scoring is based on an empirical energy function, solvation effects treated with a highly simplified model, and only ligand flexibility taken into account, with the protein structure kept fixed. The calculated binding energy results are in qualitative agreement with the observed inhibitory effects. Additionally, the simulations suggest that bivalent-IA-Cy5.5 with this conformation has a higher specificity and better fit into the known active site than other conformations.

TABLE 3

CONFORMATIONAL ENERGY OF BIVALENT IA AND NIR IMAGING PROBE

| Form of IA | Linker composition | Linker Length | Conformational Energy (kcal/mol) |
|---|---|---|---|
| Monomer | N/A | N/A | −17.0 ± 2.0 |
| Dimer (IA-X-IA) | (—C—)$_n$ | n = 1 | −37.0 ± 2.0 |
| X = linkers | | n = 2 | −50.0 ± 2.0 |
| | | n = 3 | −53.0 ± 2.0 |
| | | n = 4 | −49.0 ± 2.0 |
| | | n = 5 | −60.0 ± 2.0 |
| Near Infrared (NIR) (IA-X-P-IA) | (—C—)$_n$ | n = 5 | −53.0 ± 2.0 |

X = linker;
P = probe molecule

In Vitro Binding Affinity.

Figure 4:
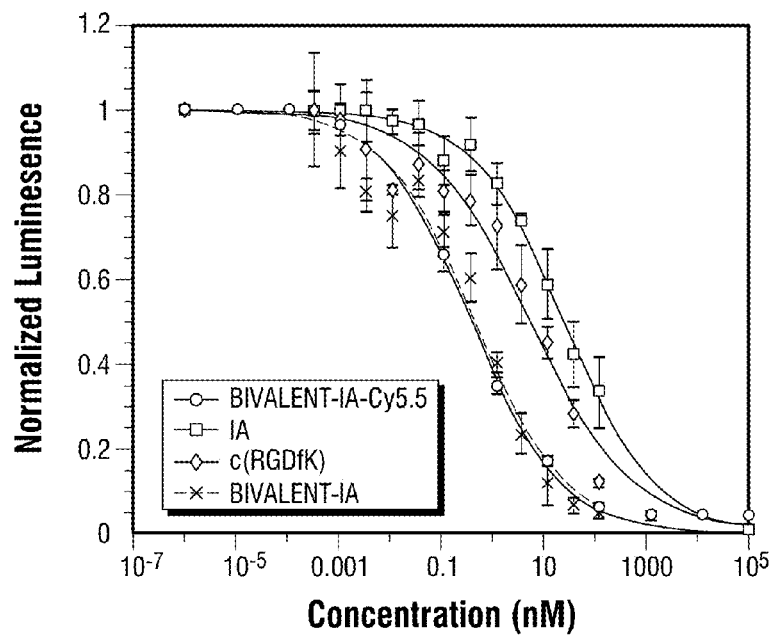
FIG. 4 shows results of an enzyme-linked immunosorbent assay (ELISA) of IA (IC50: 22.33±4.51 nM), bivalent IA (IC50: 0.40±0.11 nM), bivalent-IA-Cy5.5 conjugate (IC50: 0.13±0.02 nM), and c-[RGDfV] (IC50: 4.80±3.01 nM). In this representative study, all data points were obtained in triplicate.
Figure 5A:
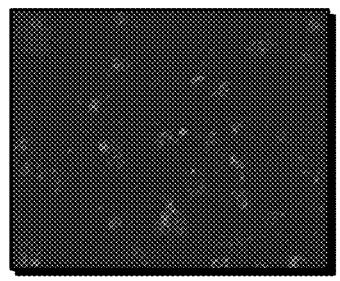
FIG. 5A, FIG. 5B, FIG. 5C, FIG. 5D, FIG. 5E, and FIG. 5F illustrate the specific binding of the bivalent-IA-Cy5.5 with U-87 cells.
Figure 5B:
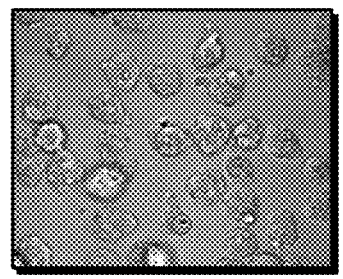
Figure 5C:
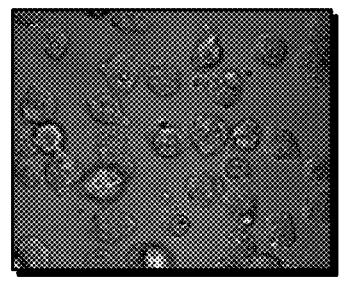
Figure 5D:
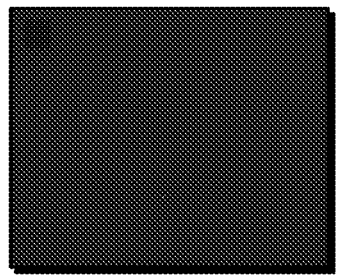
Figure 5E:
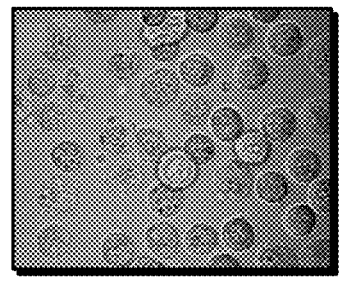
Figure 5F:
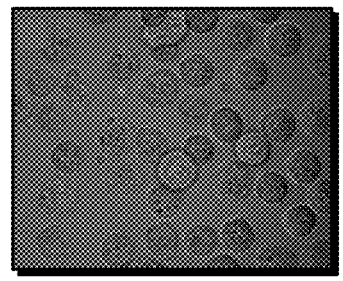

Enzyme-linked immunosorbent assay (ELISA) was used to measure the competitive binding of antagonists and biotinylated human vitronectin for the immobilized integrin $\alpha_v\beta_3$. The IC$_{50}$ values for parent compound IA, bivalent IA, bivalent-IA-Cy5.5 conjugate and c-[RGDfV] were 22.33±4.51, 0.40±0.11, 0.13±0.02 and 4.80±3.01 nM, respectively (FIG. 4). Cy5.5 conjugation did not decrease the receptor binding affinity of the resulting NIR fluorescent bivalent IA.

Fluorescence Microscopy.

Bivalent-IA-Cy5.5 conjugate was incubated with U87 cells known to overexpress integrin $\alpha v\beta 3$. Images were taken with a confocal fluorescent microscope. Receptor-mediated endocytosis was observed in the cells. The binding of bivalent-IA-Cy5.5 to U87 cells was effectively blocked by co-incubation with non-fluorescent bivalent IA (FIG. 5).

In Vivo Imaging of Integrin Overexpression in Xenograft U-87 Tumors.

Figure 7:
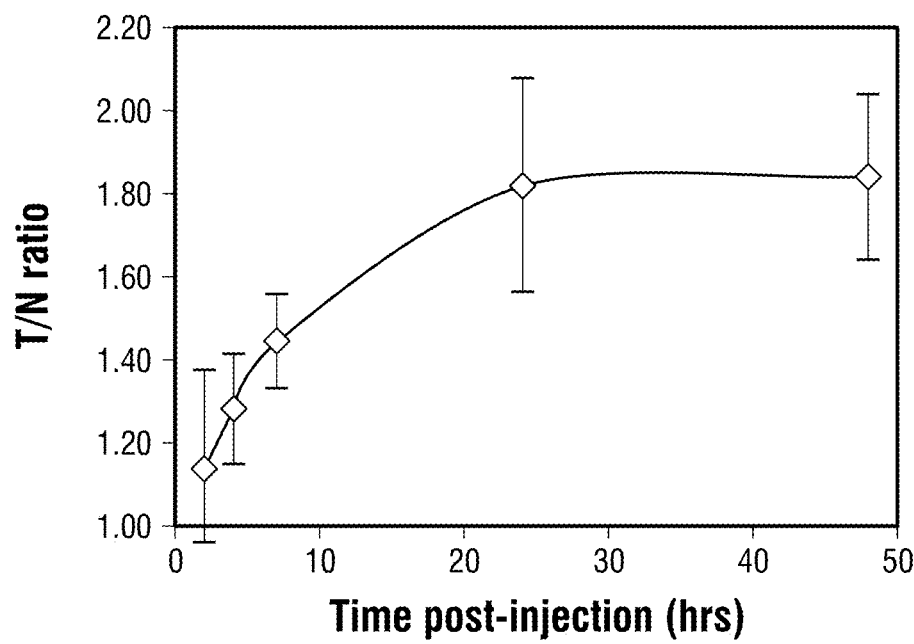
FIG. 7 shows a representative region of interest (ROI) analysis of fluorescence signal (radiance) from a tumor relative to that of normal tissue (T/N) over time (in hrs) following bivalent-IA-Cy5.5 administration. Error bars at each time point represents standard deviation from n=5 subjects.

Whole-animal fluorescence imaging of subcutaneously implanted U-87 xenograft tumors demonstrated increased signal in tumor sites at 7, 24, and 48 hrs post-contrast injection (FIG. 6). Imaging at earlier time points (2- and 4-hr) showed intense systemic fluorescence signal due to relatively slow clearance of the compound. However, at 7 hr, there was sufficiently high tumor-to-normal tissue (T/N) contrast to clearly discern the lesion; and by 24 and 48 hr, the most intense signal was evident at the tumor site. Region of interest (ROI) analysis was performed by determining the boundaries of superficial tumors based on photographic images; this region was then measured for fluorescence signal (radiance units, photons/sec/cm2/steradian). Normal tissue was selected by copying the ROI of each sample to a site in the anterior flank. As plotted in FIG. 7, T/N ratios reach a plateau at 24 hr with an average maximum of ~1.84. For the 7, 24, and 48 hr time points, the fluorescence signals of the tumor and normal tissues were statistically significantly different (two sample, one side t-test, p-value 0.006, 0.015, and 0.007, respectively, n=5).

Figure 8:
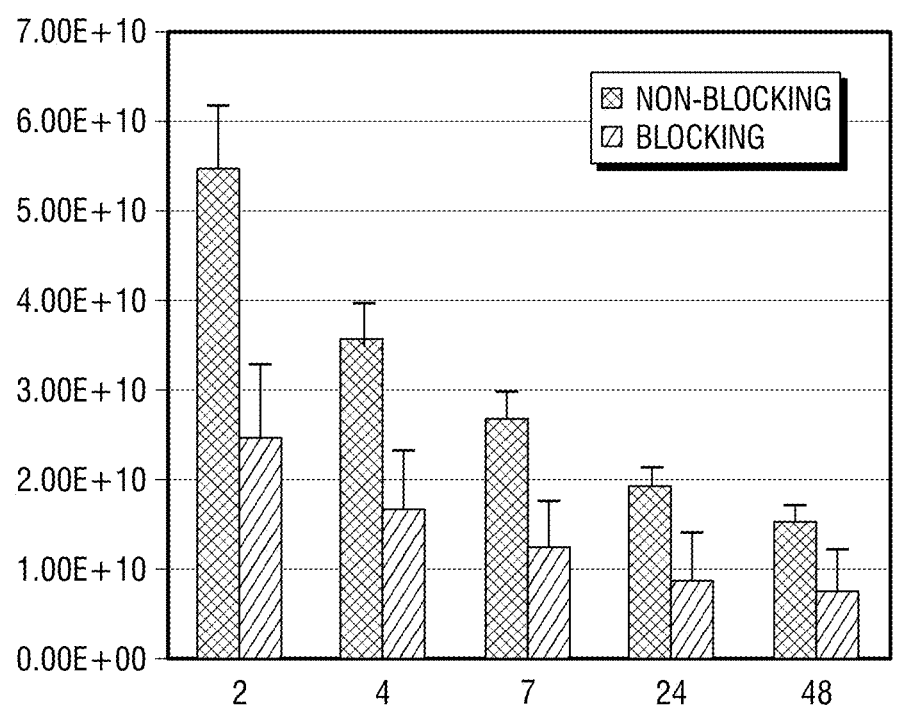
FIG. 8 shows the competitive inhibition of bivalent-IA-Cy5.5 conjugate with non-fluorescent bivalent IA. Significant blocking of tumor fluorescence signal (y-axis) was observed at all time points (x-axis). The units of radiance are in p/s/cm2/sr; error bars indicate the standard deviation from n=6 blocked, n=4 non-blocked.
Figure 9A:
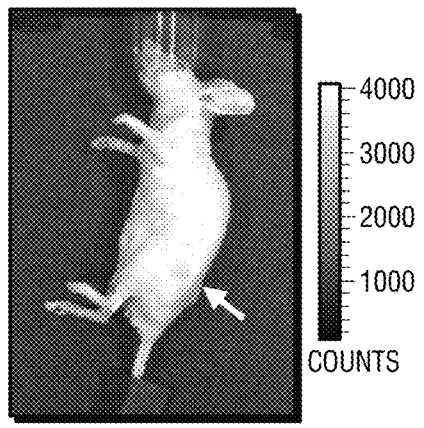
FIG. 9A, FIG. 9B, FIG. 9C, and FIG. 9D show an illustrative imaging study in accordance with one aspect of the present invention.
Figure 9B:
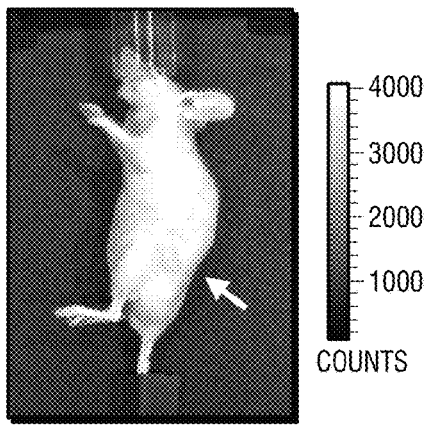
Figure 9C:
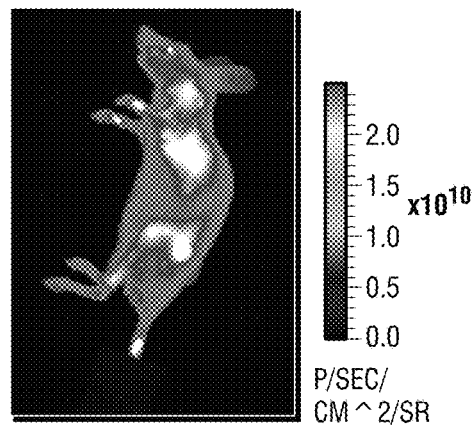
Figure 9D:
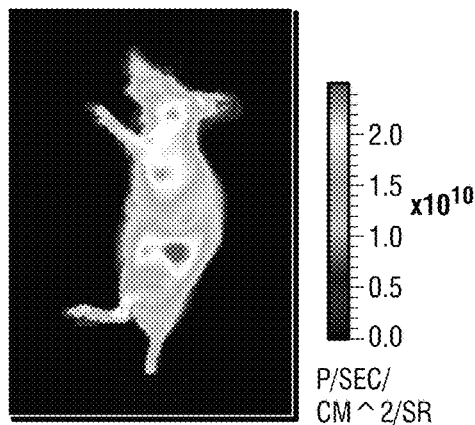

To ascertain the specificity of this tumor-tissue signal localization, competitive inhibition studies were performed using the non-fluorescent (without Cy5.5) bivalent IA. Using the same tumor model, a 10-fold excess of bivalent IA was co-administered with 10 nmol of bivalent-IA-Cy5.5 and were imaged at 2, 4, 7, 24, 48 hrs. ROI analysis was again performed as described above. When compared between blocking and non-blocking controls fluorescence signal within tumors were reduced at all timepoints measured, but was most pronounced in the earlier time points (2, 4, and 7 hrs), perhaps due to differing clearance rates of the two compounds (FIG. 8). Nonetheless, the observed blocking effect was significant at every time point (two sample, one side t-test, p=0.001 (2 hr); 0.002 (4 hr); 0.003 (7 hr); 0.012 (24 hr); and 0.019 (48 hr); n=6 (blocking); n=4 (non-blocking control).

As a negative control, two tumor-bearing animals were intravenously injected with 10 nmol of the free Cy5.5 and imaged at 24 hrs post injection. As shown in FIG. 9, there was an overall reduction in systemic fluorescence signal from the entire animal. The relative amount of fluorescence signal from the tumor appears to be slightly higher than the background but is lower than that achieved with the bivalent-IA-Cy5.5 (cf. FIG. 9 left vs. right panels). This result is best explained by a higher clearance rate of the free fluorophore and a certain degree of nonspecific binding to tumors as observed by other investigators (Cheng et al., 2006). Collectively, these data support the specificity of the bivalent-IA-Cy5.5 for integrin $\alpha_v\beta_3$ associated with U-87 tumors.

Given the intrinsic limitation in tissue penetration of excitation and emission photons from fluorophores, ex vivo imaging was performed to assess the fluorescence signal of the tumor relative to internal organs. Following the intravenous administration of the bivalent-IA-Cy5.5, two tumor-bearing animals were imaged as described above at 24 hrs' post-injection, and immediately thereafter euthanized for harvest of internal organs. Tumors and the major organs—heart/lung (en bloc), liver, spleen, gastrointestinal tract, and bilateral kidneys—were resected and placed on a black background and imaged under the same imaging acquisition protocol (FIG. 10A). Quantitative analysis was performed by measuring the total photon flux of each selected tissue and divided by the mass (FIG. 10B). The highest signal per mass of tissue was observed for the tumor, followed next by the heart and lung (en bloc), and kidneys. These data indicated that the bivalent-IA-Cy5.5 was specific for the tumor tissue, likely through binding to its cognate integrin receptor. Given the moderate level of fluorescence signal in the heart and lung, this compound is likely to have a relatively slow blood-pool clearance rate. Fluorescence signal from the kidneys suggested mainly renal clearance of the agent and minimal liver signal suggest low hepatic metabolism.

Figure 24:
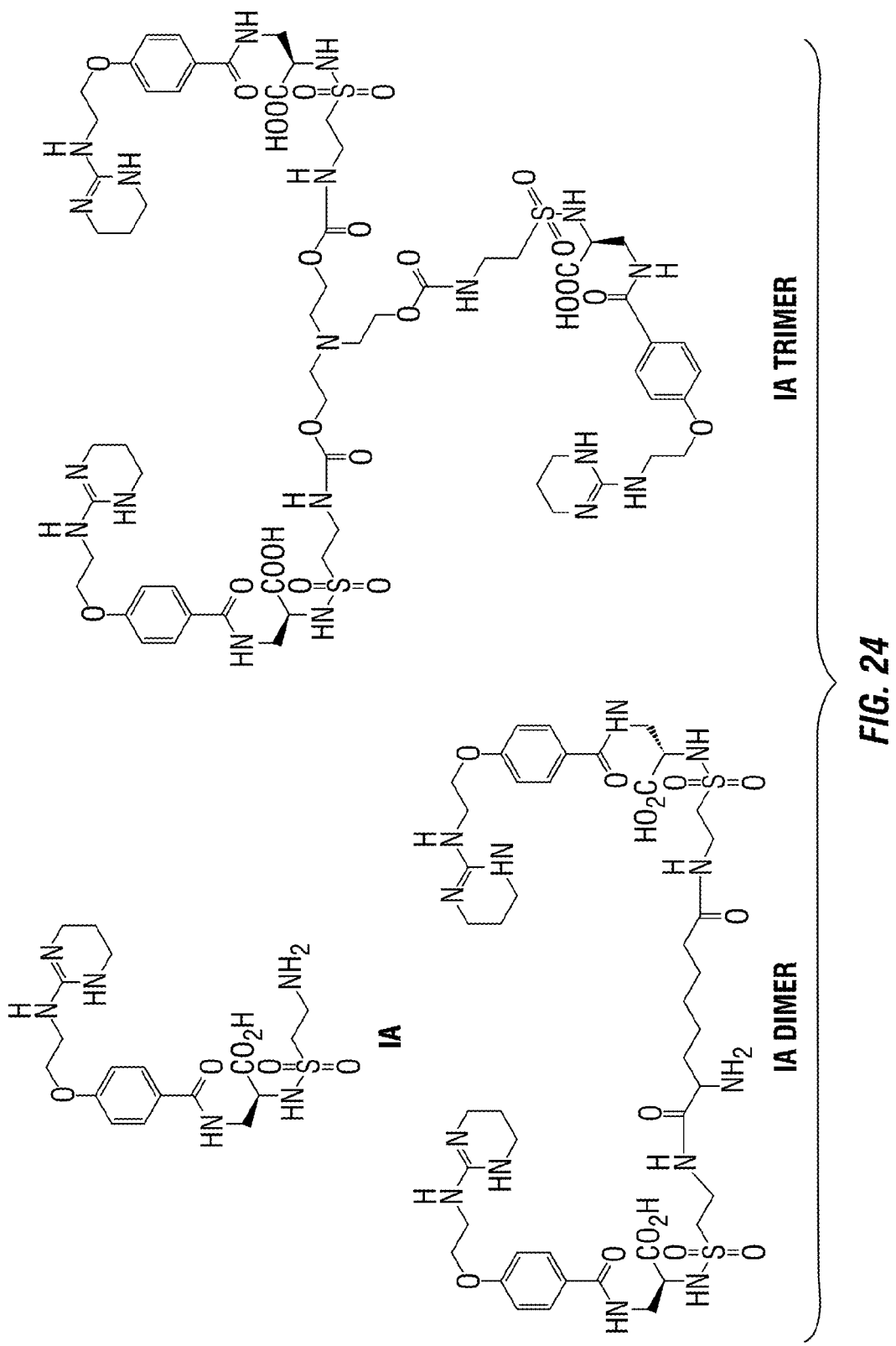
FIG. 24 shows the schematic structure of IA monomer, IA dimer and IA trimer.
Figure 25A:
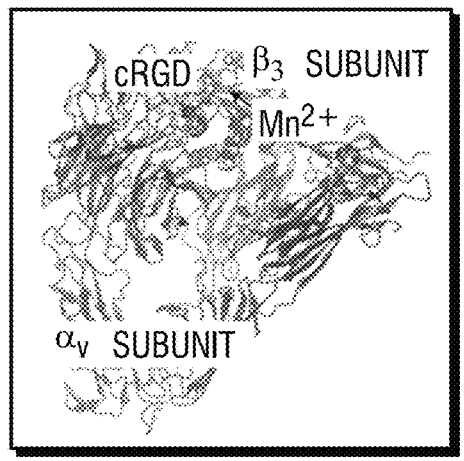
FIG. 25A and FIG. 25B show side and top views, respectively: Overall view of cRGD-binding integrin $\alpha_v\beta_3$ (PDB ID: 1L5G) shown in ribbon model and surface models, respectively. The $\alpha_v$ and $\beta_3$ subunits are in blue and red, respectively, while cRGD are in space-filling model.
Figure 25B:
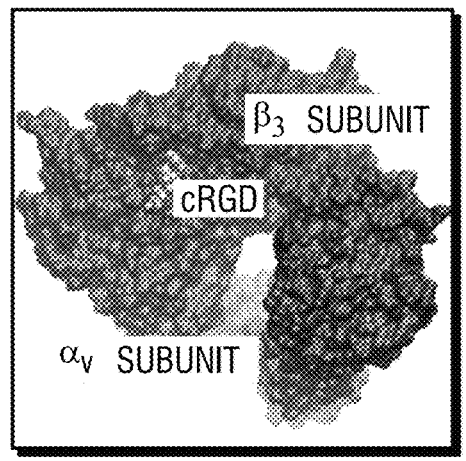
Figure 26A:
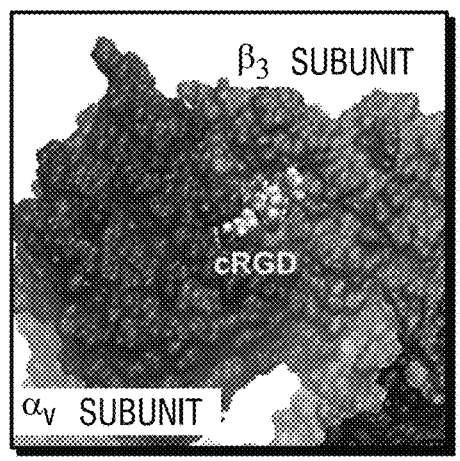
FIG. 26A, FIG. 26B, FIG. 26C, and FIG. 26D illustrate particular aspects of the present invention.
Figure 26B:
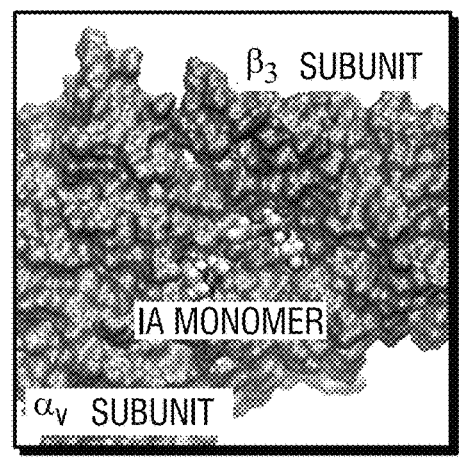
Figure 26C:
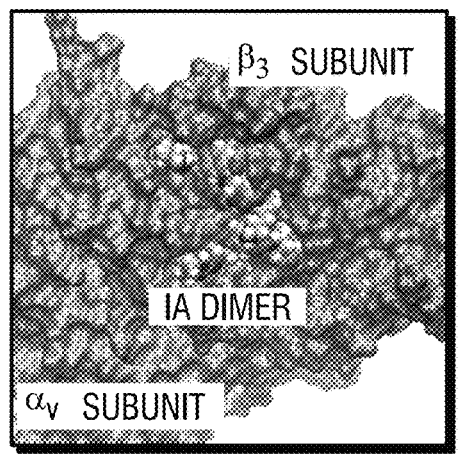
Figure 26D:
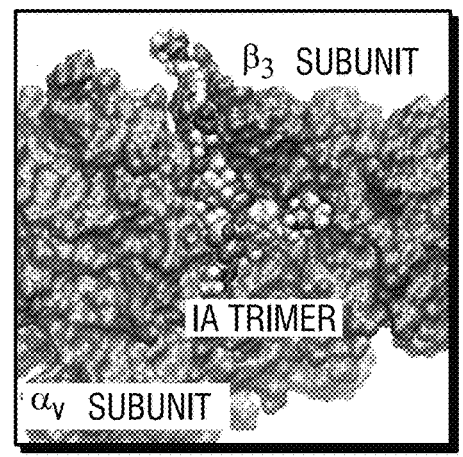
Figure 27A:
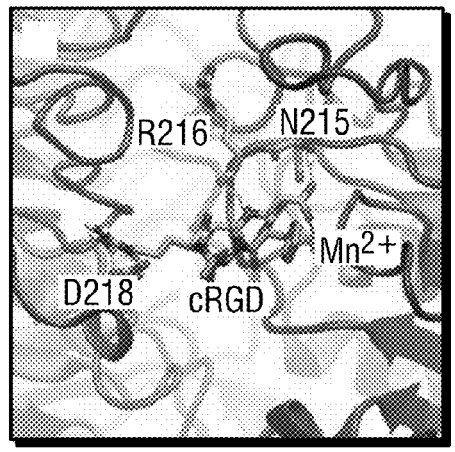
FIG. 27A, FIG. 27B, FIG. 27C, and FIG. 27D illustrate particular aspects of the present invention.

The chemical structures of the IA monomer, dimer and trimer are shown in FIG. 24. As shown in FIG. 25, FIG. 26A and FIG. 27A (crystal structures), the binding site crosses the interface of αv and β3 subunits. The receptor structure for docking is extracted from crystal 1L5G, the extracellular segment of integrin αvβ3 in complex with ligand cRGD. The protein is ligated by cRGD and the domain occupied by this cyclic peptide is treated as the binding site to dock the IA monomer, dimer and trimer. The top-scoring docking poses are taken as initial structures for the following 3-ns MD simulation. The last frames are extracted from these 3-ns trajectories and shown in FIG. 26B, FIG. 26C and FIG. 26D and FIG. 27B, FIG. 27C and FIG. 27D. In FIG. 26, the protein and ligands are shown in surface and space-filling models, respectively, while in FIG. 27 in ribbon and stick models, respectively. cRGD and the protein in FIG. 26A and FIG. 27A are rendered directly from crystal 1L5G. Simulation results showed all IA ligands were able to dock into the cRGD-binding pocket and MD simulations confirmed stability of the IA-binding and their similarity to cRGD.

As seen in FIG. 26B, FIG. 26C, and FIG. 26D, and FIG. 27B, FIG. 27C, and FIG. 27D, one IA unit in the IA monomer, dimer and trimer perfectly fit into the cRGD-binding site. The cyclic guanidinium head forms a salt bridge with the carboxylate side chain of the Asp-218 while the carboxylate in the same IA unit coordinates to Mn2+. These two sets of bonding between the IA ligands and integrin $α_vβ_3$ keep the binding conformation of the ligands rigid and suffice the hydrophobic interactions between the middle section of the IA unit and the non-polar amino acid residues contacting IA.

Figure 27B:
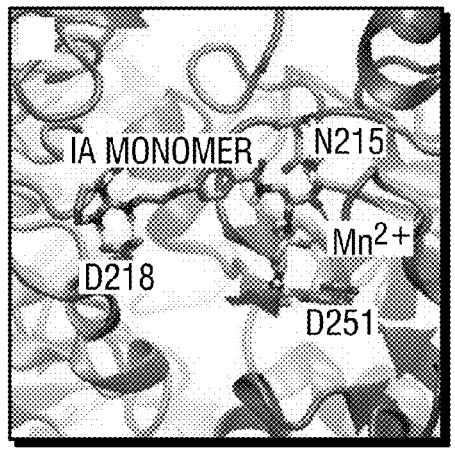
Figure 27C:
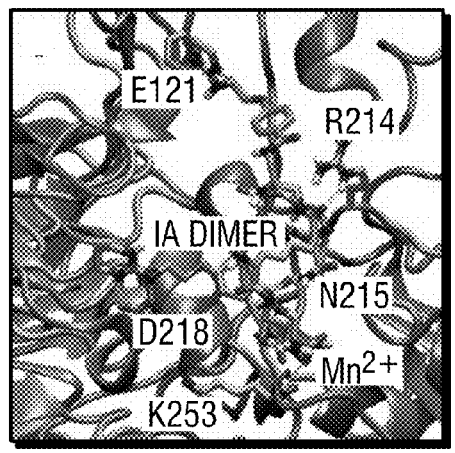

In the monomer-binding system, the sulfonamide linkage chelates to Mn2+ together with the IA carboxylate while the IA carboxylate further forms an H-bond with the amide side chain of Asn-215 (see FIG. 27B).

In the dimer-binding system, the binding of the first IA unit is largely the same as that in the monomer-binding system although the IA carboxylate and the IA amide H-bond to the backbone amide in Lys-253 and the amide sidechain in Asn-215, respectively. The second cyclic guanidinium head extends out and forms a salt bridge with Glu-121 in the αv subunit. One amide in the linker of IA dimer forms two H-bonds to Asp-215 backbone carbonyl and Arg-214 sidechain. Apparently, these two sets of H-bond networks allow the middle section of the second IA unit to effectively contact the non-polar $β_3$ subunit surface, formed by the benzoyl group in Tyr-166 (see FIG. 27C). Furthermore, an intramolecular H-bond formed by the first IA amide and sulfonamide further enhanced the rigidity of the IA-dimer when it binds. Based on the structural data from the MD trajectory, the in vitro measured 28-fold IC50 increase from IA-monomer to dimer is largely stemmed from the sufficient contact between the second IA unit in the dimer and the $β_3$ subunit surface, which is secured by the H-bonds formed between Arg-214 and Glu-121.

Figure 27D:
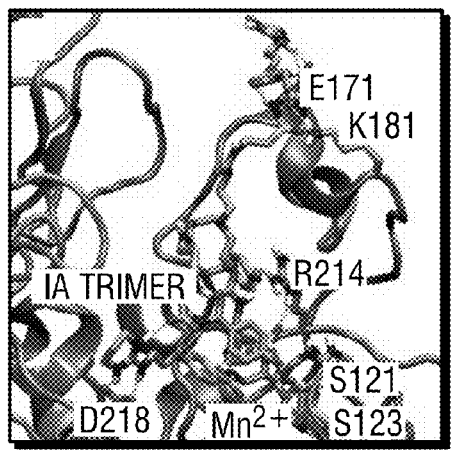

In the trimer-binding system, the binding of the first IA unit is not significantly different from that in the monomer- and dimer-binding systems although the first IA carboxylate not only coordinates to Mn2+ but also H-bonds to Ser-121 and Ser-123 (see FIG. 27D).

The second IA unit extends out to the edge of the interface between integrin αv and β3 subunits. The guanidinium head and carboxylate tail in this unit form H-bonds with Glu-171 and Lys-181, respectively while an intramolecular H-bond between the amide in this IA unit and the linker sulfonamide. These H-bonds keep this IA unit rigid in the binding conformation and allow the non-polar contact between the middle section of this unit and the non-polar surface formed by Pro-170, Ala-172 and Tyr-178. These hydrophobic interactions should be the major contribution to the 56-fold IC50 increase from IA-monomer to trimer. The third IA unit does not directly interact with the protein although it forms a few H-bonds with the first IA unit. The guanidinium head is well solvated in solvent and the phenyl in the middle stacks on the phenyl in the first IA unit. Apparently, this IA unit seems not to contribute significantly to the binding to protein and that is why there is only 2-fold increase in IC50 from the dimer to trimer.

The binding free energies of the IA ligands to integrin αvβ3 were approximated with GB/SA and PB/SA methods are listed in Table 5. The calculation indicate a trend that the monomer binds to integrin αvβ3 significantly weaker than the dimer and trimer while the trimer might bind slightly more strongly than the dimer does. Surprisingly, both GB/SA and PB/SA estimate the binding free energies of the monomer and dimer consistently and the differences between these two ligands are 22.4±6.1 and 28.7±8.2 kcal/mol, respectively. However, the differences between the dimer and trimer are 28.7±6.2 and −7.7±8.2 kcal/mol, respectively, by GB/SA and PB/SA. GB/SA predicts trimer is a stronger ligand binding to integrin $α_vβ_3$ comparing to dimer while PB/SA interprets these two IA ligands bind with similar binding affinity.

In Vitro Results

Figure 28:
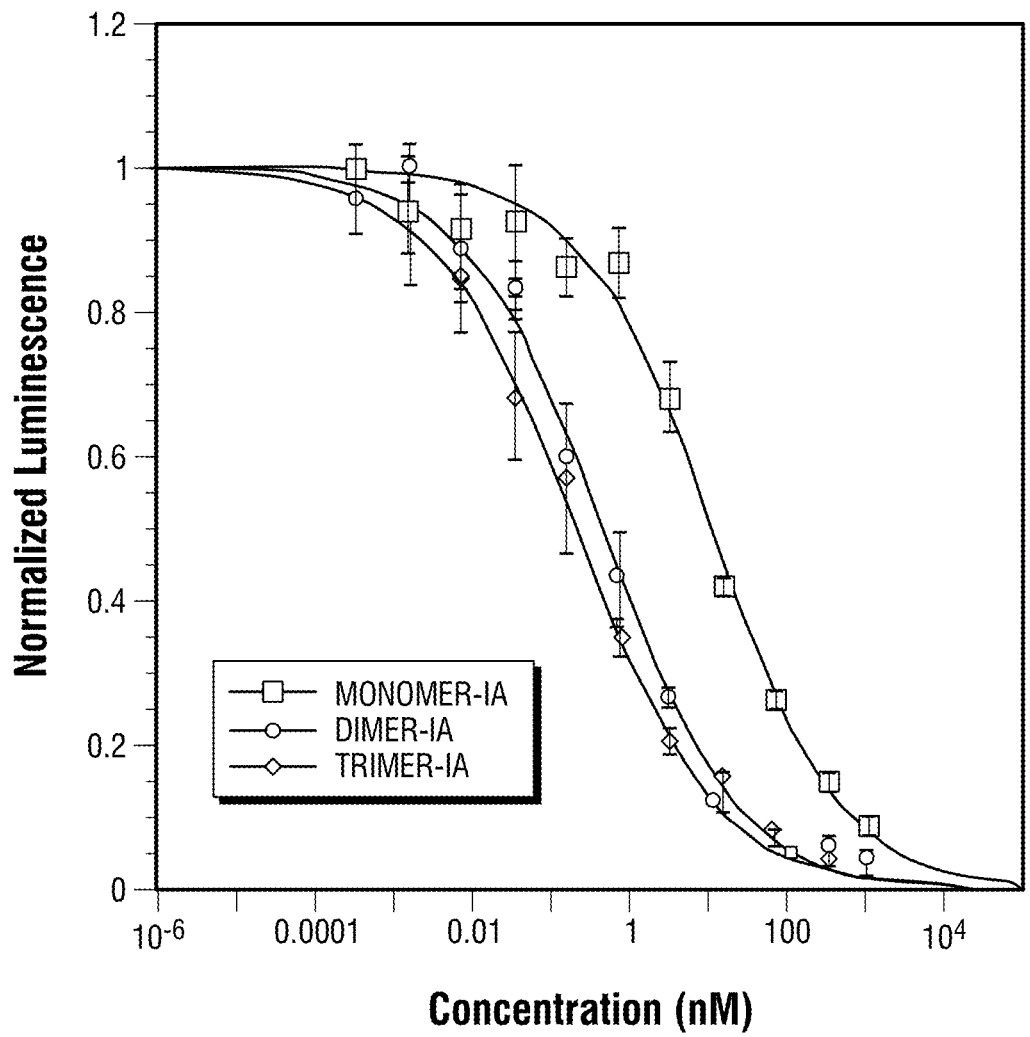
FIG. 28 shows an enzyme-linked immunosorbent assay (ELISA) of IA monomer (IC50: 11.00 ELISA) nM), dimer (IC50: 0.44 r (ICICnM), and trimer (IC50: 0.22 (ICmer nM). All of the points were performed in triplicate.

Enzyme-linked immunosorbent assay (ELISA) was used to measure the competitive binding of antagonists and biotinylated human vitronectin for the immobilized integrin $α_vβ_3$. The $IC_{50}$ value for monomer IA, dimer IA, and trimer IA were 11.00±2.49 nM, 0.44±0.13 nM, and 0.22±0.09 nM, respectively (FIG. 28).

Figure 29A:
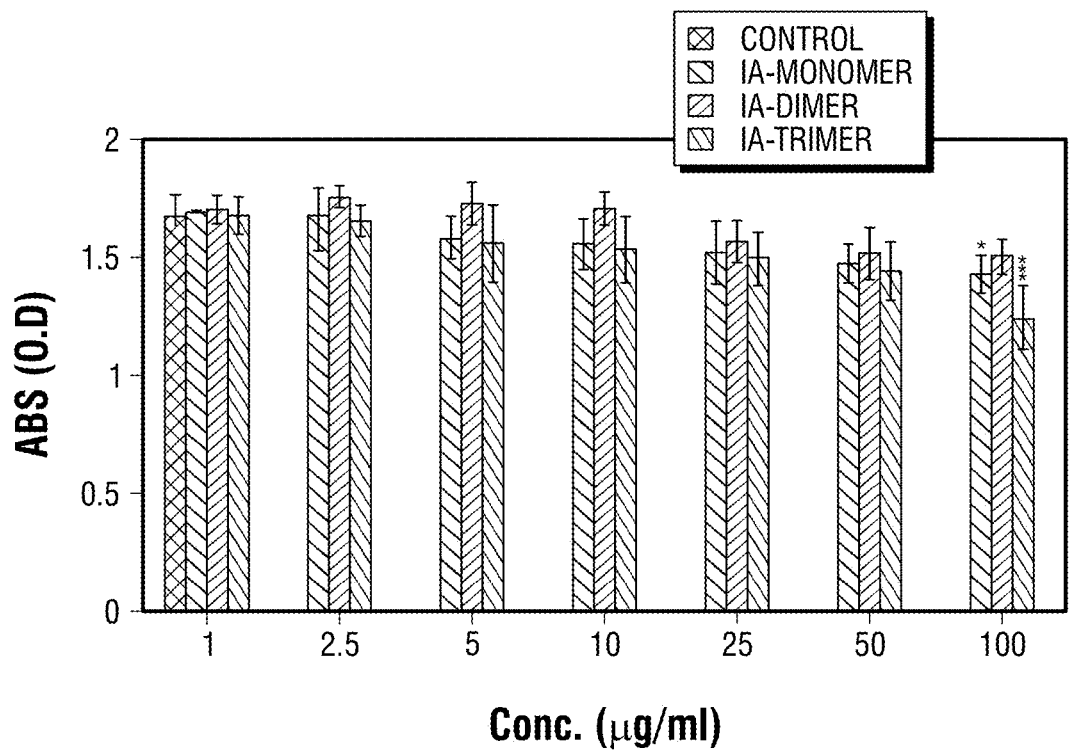
FIG. 29A and FIG. 29B show the in vitro cytotoxicity of IA-monomer, IA-dimer and IA-trimer against B16F10 cells (FIG. 29A) and HUVECs (FIG. 29B) after the incubation of 24 hr. The results represent the means±SD s (n=6). Significance indicators are relative to Control: * p<0.05,  p<0.01, * p<0.001.
Figure 29B:
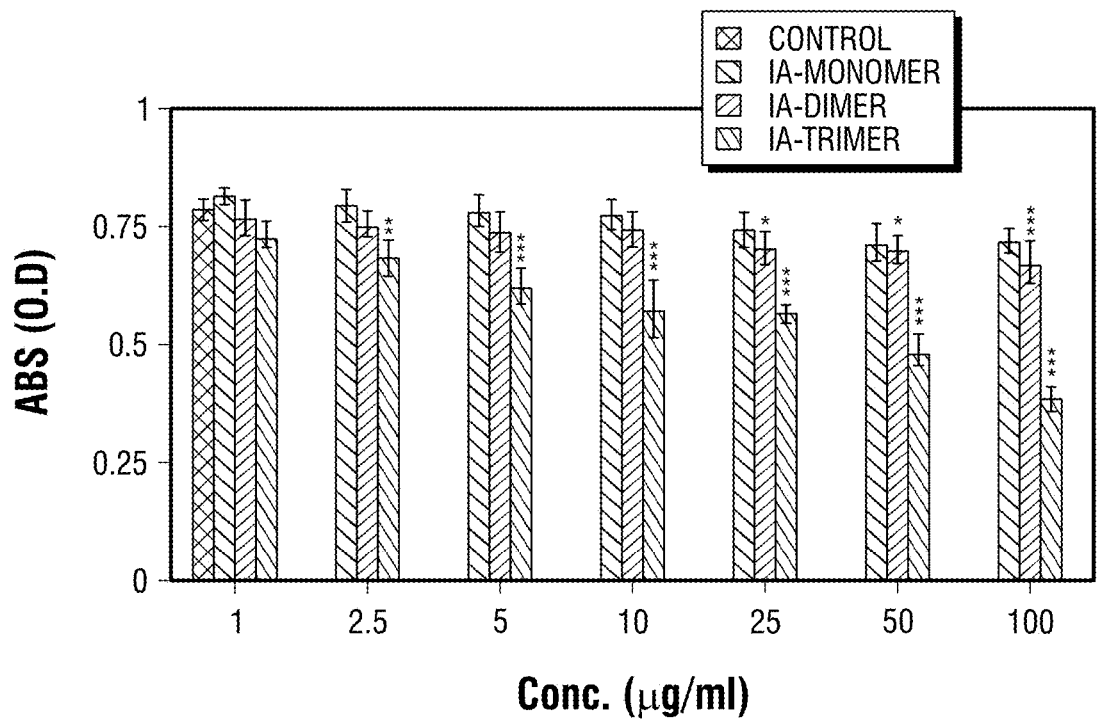
Figure 30A:
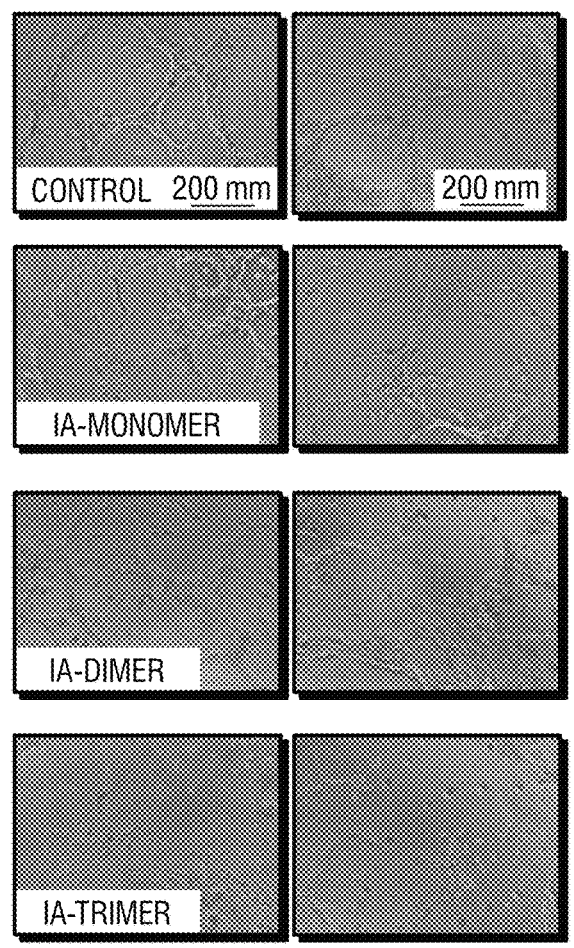
FIG. 30A and FIG. 30B show the reduction in tubular network formation in culture of HUVECs after treatment with IA-monomer, IA-dimer and IA-trimer at doses of 1 μg/mL (left) and 10 μg/mL (right) (FIG. 30A). Based on ANOVA and TukeyHSD (FIG. 30B), all treatment groups are significantly different from each other (p<0.05) except: Control to IA-Monomer 1 μg, IA-Monomer 1 μg to IA-Monomer 10 μg, and IA-Dimer 1 μg to IA Dimer 10 μg.
Figure 30B:
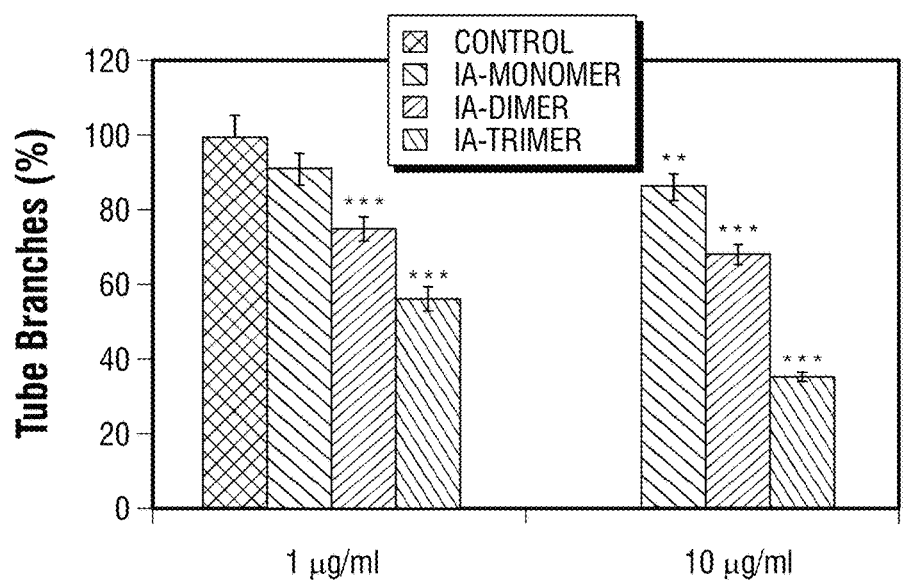

As shown in FIG. 29A, the 3 IA derivatives showed weak toxicity against B16F10 tumor cell line. IA-monomer and IA-dimer had less toxicity than the IA-trimer. About 90% of the cells were viable after a 1-day exposure to 10 μg/mL IA-trimer, whereas more than 99% of the cells remained viable when exposed to the same concentration of IA-monomer and IA-dimer. At the highest concentration, 100 μg/mL, cell viability was reduced to ~80% for the IA-trimer (p<10-5), while the changes of cell viability in the IA-monomer or IA-dimer groups were smaller and less significant. The same methods were used to study anti-proliferative effects on endothelial cells (HUVECs) with very different results. In FIG. 29B, the effects of the IA derivatives on HUVEC cells are shown to be significantly greater than the same dose on the B16F10. The IA-trimer shows increased cytotoxicity over the IA-monomer and dimer at doses from 1 μg/mL to 100 μg/mL. From this dose of IA-monomer and dimer, endothelial cells are slowly dying, suggesting that these compounds may have detrimental effect on the growth of blood vessels. The tubular network formation assay further demonstrated this effect. The formation of capillary-like tube structures by HUVECs in ECM is the pivotal step in angiogenesis, and is also involved in cell migration and invasion. HUVECs attached to reconstituted extracellular matrix (Matrigel) will normally form capillary-like tubular structures. It is considered that these processes in the extracellular matrix are representative of the later stages of angiogenesis during differentiation and that they are also involved in cell migration and invasion. Tube formation actively occurred in the control group. In FIG. 30A, at 6 hr, cell alignments and tubular structure formations were observed in HUVECs treated with IA derivatives and the inhibitory effects of IA-monomer, IA-dimer and IA-trimer were evident. In particular, IA-trimer exhibited the greatest inhibition against cell alignments and tubular structure formations. The number of tube branches was reduced from 100% in the control group to 86.6±3.4% in the IA-monomer group, 68.3±2.6% in the IA-dimer group, and 35.6±1.0% in the IA-trimer group (all at 10 µg/mL dose) (FIG. 30B). As the incubation period continued to 6 hr, HUVECs treated with IA derivatives gradually lost intercellular contact.

Therapeutic Results

Figure 31A:
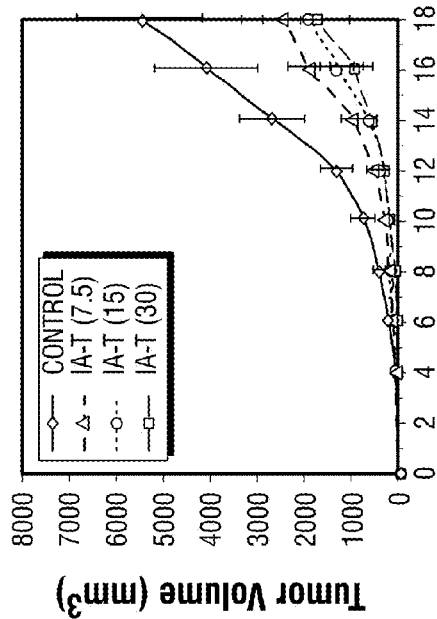
FIG. 31A, FIG. 31B, FIG. 31C, and FIG. 31D show in vivo anti-tumor activity of PBS, IA based IA-monomer, IA-dimer and IA-trimer (FIG. 31A, FIG. 31B, and FIG. 31C, respectively) after administration i.p. twice per day of similar pharmacological dose. The results show the means±SD (n=7).
Figure 31B:
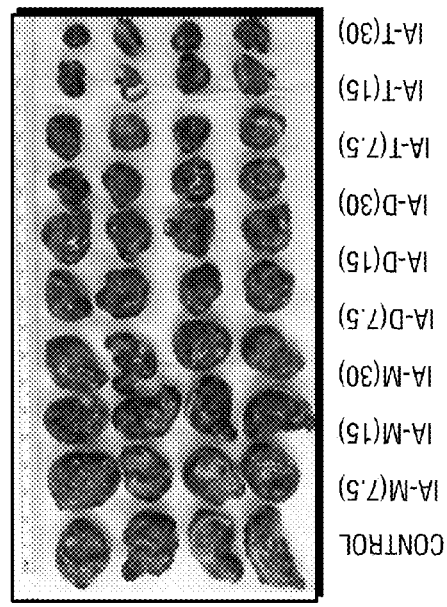
Figure 31C:
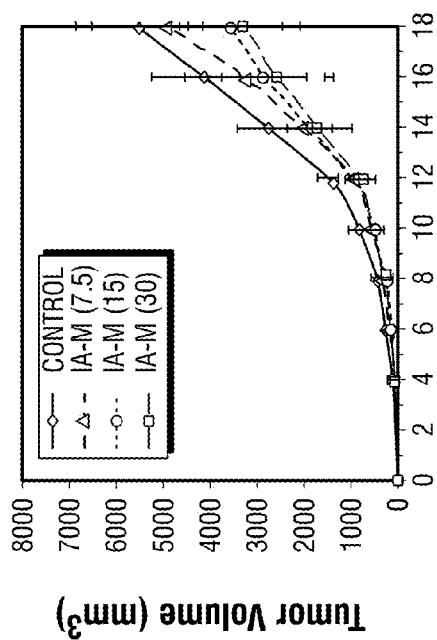
Figure 31D:
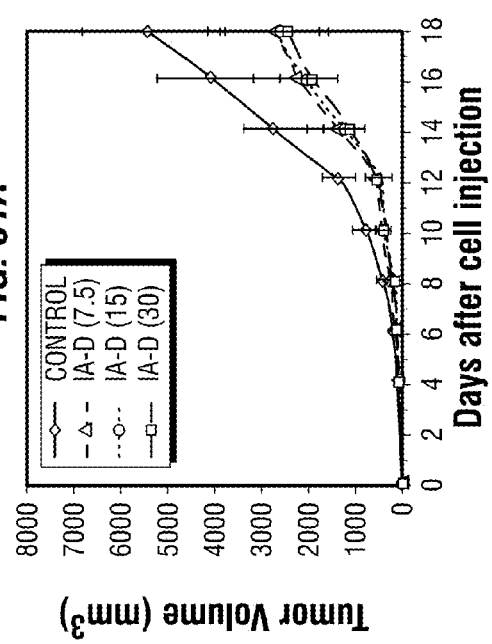
Figure 32A:
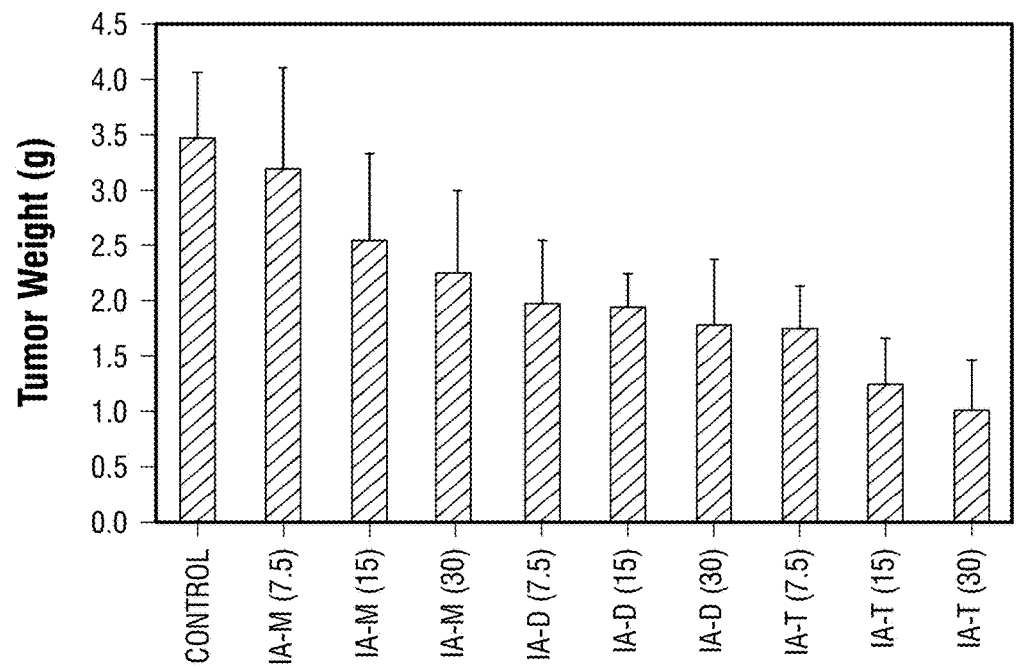
FIG. 32A and FIG. 32B show the tumor and body mass, respectively, of mice at the end of an exemplary study in accordance with one aspect of the present invention. Results represent means±SD (n=7)
Figure 32B:
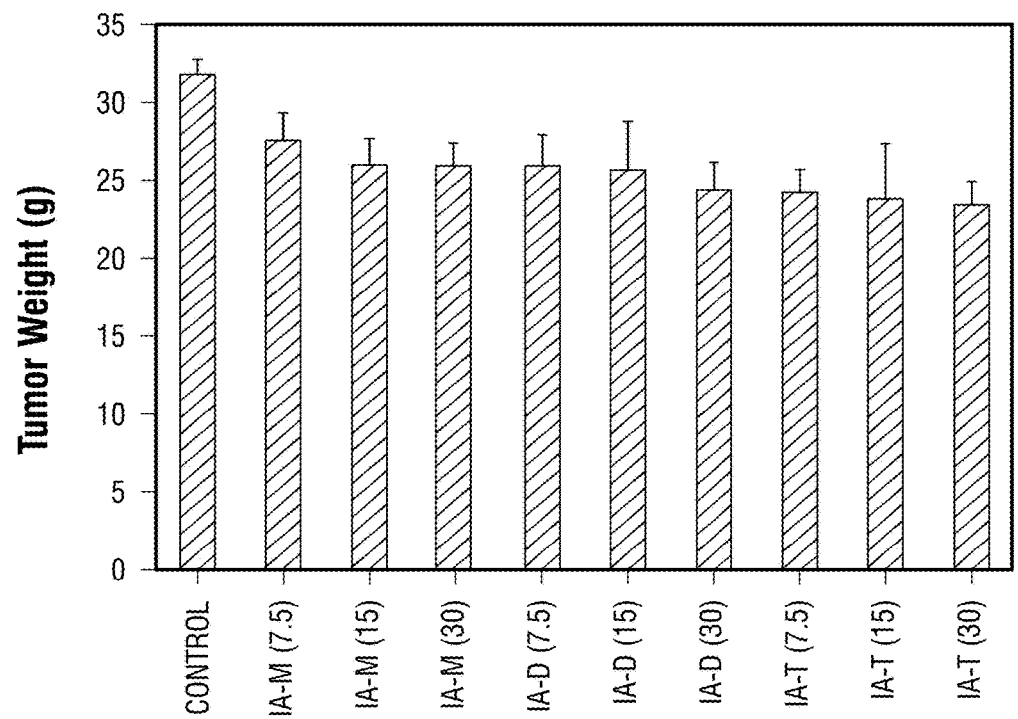
Figure 33A:
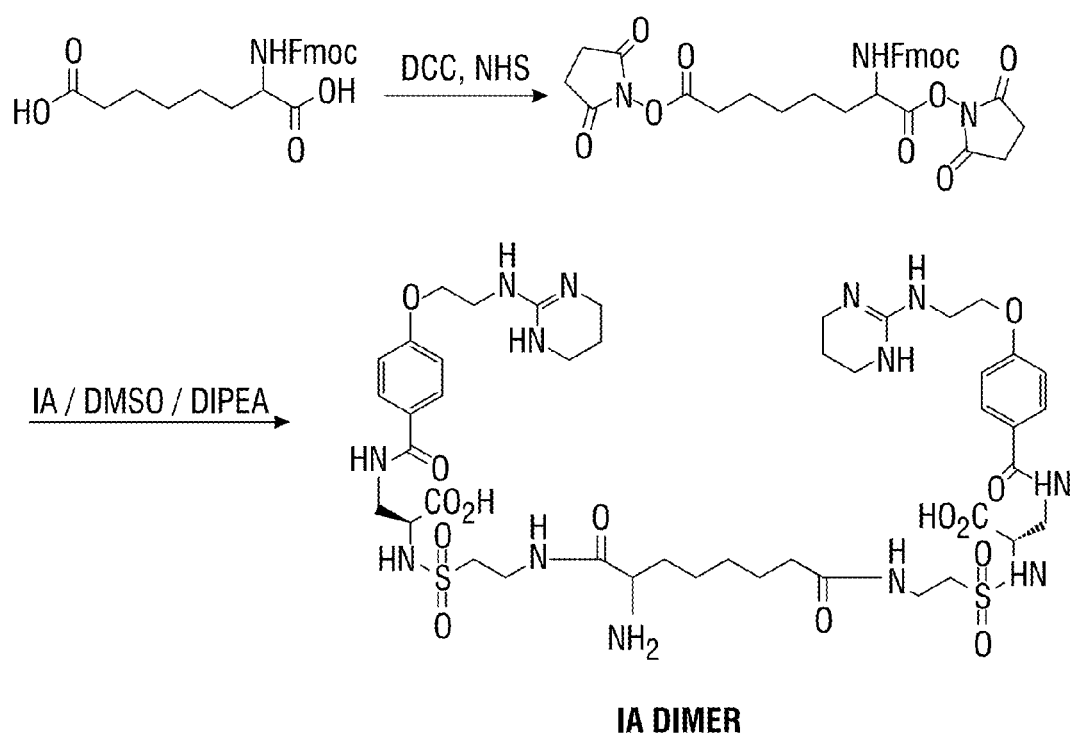
FIG. 33A and FIG. 33B show a synthetic scheme of IA dimer and IA trimer, respectively, in accordance with one aspect of the present invention.
Figure 33B:
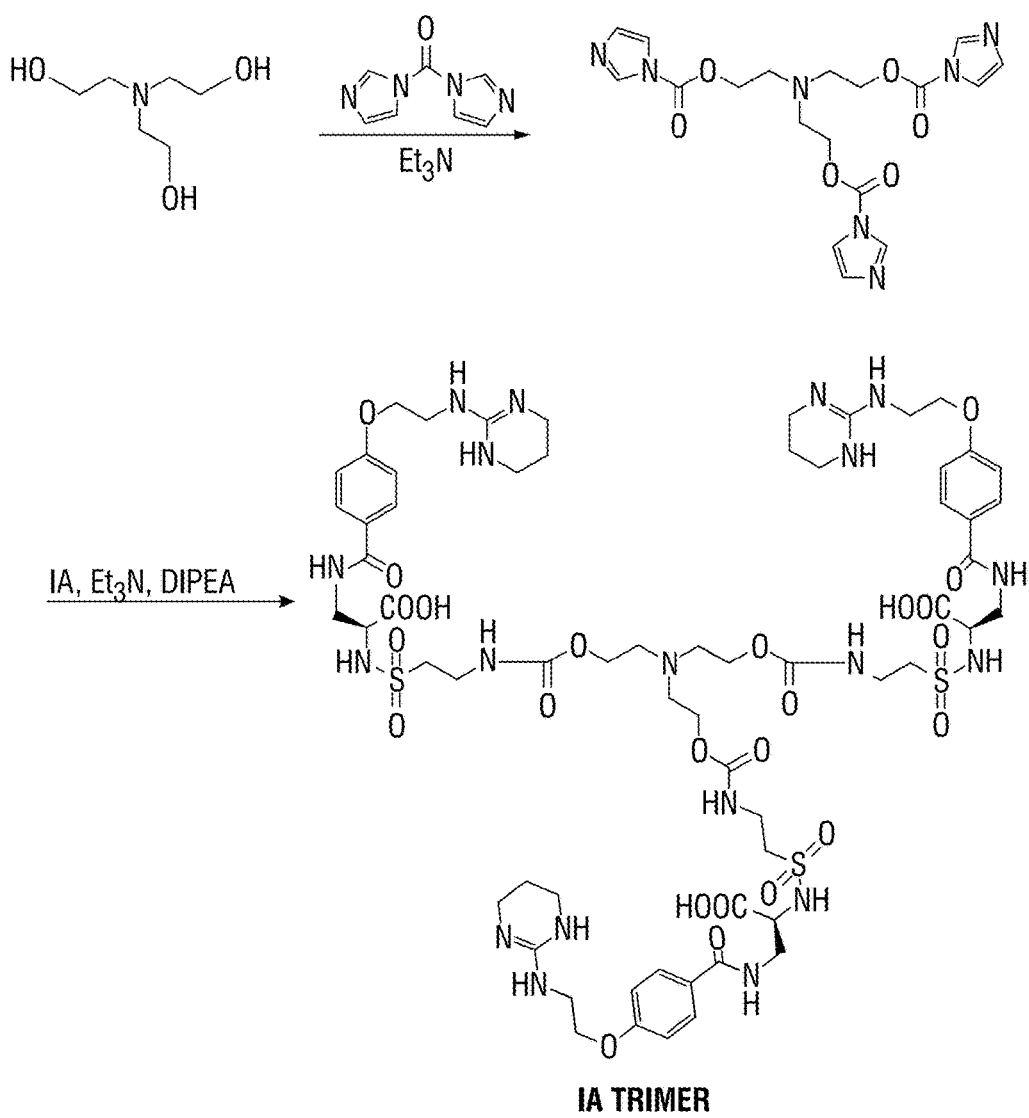

The in vivo antitumor efficacies of IA derivatives, IA-monomer and IA-dimer with IA-trimer were studied in B16F10 tumor-bearing mice. As shown in FIG. 31, groups receiving IA derivatives showed powerful tumor suppression compared to sham treated control animals. Treatment began on day 3 (tumor inoculation day=day 0) when the tumor volume range from 50 to 100 mm$^3$. By 14 days after the start of treatment (17 days after tumor inoculation), the average tumor volume in 15 mg/kg IA-trimer compound-treated mice had increased relatively slowly and attained less than ⅓ of the average tumor volume in PBS-treated control mice. The tumor volume showed a statistically observable dose dependent pattern for each of the IA-monomer, IA-dimer and IA-trimer. This is reflected in the statistical tumor growth model by a statistically significant (p<0.025) estimate of model parameter B=−2.14×10-4±9.5× 10-5 PD[uM]-1 day-1, where growth of the control tumor is given by the parameter A=0.15±3.2×10-3 day-1 (p<10-15). Among the three test compounds, the average tumor size in the IA-trimer group was significantly smaller (2.3-fold, 1.7-fold) than the tumor size in the IA-monomer and IA-dimer groups. The tumor volume in the IA-trimer test group (dose 30 mg/kg) reached an average volume of 1800 (s.d. 800) mm$^3$, while those of the IA-dimer and IA-monomer and control animals attained 2500 (s.d. 1000) mm$^3$, 3300 (s.d. 1200) mm$^3$ and 5500 (s.d. 1300) mm$^3$, respectively. Multivalency improved outcome despite the fact that these groups were given roughly the same pharmacophore. This is reflected in the fitting parameter controlling how the tumor growth model responds to valency, C=−1.22×10-1.7×10-4 ED[uM]-1 day-1 (p<10-12). Physically, this implies that increasing valency (e.g., from monomer to dimer) has a statistically observable greater impact in reducing tumor growth than an equivalent increase (doubling) of monomer dose. FIG. 31D showed collected tumor tissues; the tumor size is visibly dose and valency dependent. The tumor weight at endpoint is shown in FIG. 32A. For the 30 mg/kg groups, the IA-trimer induced a 71±7% reduction in tumor mass compared to control, while the IA-dimer gave a 49 t 8% reduction and the IA monomer a 36±9% reduction. Before sacrifice, the mice body weights showed no significant change except in the control animal group (FIG. 32B). Only two mice died in the PBS injected control group within 12 days due to excessive tumor burden, while in the mouse groups receiving IA-monomer, IA-dimer, IA-trimer, all of animals survived for at least 2 weeks after treatment. Thus, despite the low expected tumor cell toxicity, the IA derivatives showed demonstrable anti-tumor effectiveness dependent on both pharmacological drug dose and multivalency.

Discussion

In this example, the therapeutic efficacy of multivalent IAs was characterized, and it was shown that multivalency of IA enhanced the anti-tumoral efficacy in mice. IA-monomer IA-dimer and IA-trimer were used for the in vitro and in vivo efficacy study. Surprisingly, neither the IA nor its multivalent derivatives had any large impact on the proliferation of tumor cells (B16F10) in vitro, despite the overexpression of integrin $\alpha_v\beta_3$ in this cell line (Smolarczyk et al., 2006). In vivo, the anti-tumor efficacies of the IA monomer, dimer and trimer were evaluated in subcutaneous B16F10 melanoma tumor-bearing mice. IA compounds were given by intraperitoneal injection for 14 days in three different doses, and significantly impaired tumor growth in a dose and valency dependent manner. One explanation for these observed effects is that the IAs impair tumor growth by blocking angiogenesis and by impairing endothelial cell function rather than by impeding tumor cell growth directly. Human endothelial cells express integrin $\alpha_v\beta_3$ receptors on the luminal aspect of their membrane (Conforti et al., 1992). In vitro testing with an endothelial cell line (HUVEC) appears to support this hypothesis, with a dose and multivalency dependent reduction in endothelial cell viability and proliferation as well as endothelial tubular network formation. The anti-tumor effect does not appear to be limited to $\alpha_v\beta_3$-positive tumors, and appears to be applicable to any tumor that is actively recruiting endothelial cells.

Previous studies showed RGD multivalency results in increasing binding affinity, which was then leveraged for improved imaging (Liu et al., 2009; Mittra et al., 2011; Shi et al., 2008) and integrin targeted therapeutic delivery (Chen and Chen, 2011; Chen et al., 2005). However, despite the many studies over years, there are no reports that have demonstrated improved therapeutic effectiveness of multivalent RGDs over RGD monomer. The present invention is the first unequivocal demonstration of a significant improvement in therapeutic effect of integrin antagonists due to multivalency alone. Theoretical simulations not only reveal the atomic basis in the improved bindings but also indicate room to further increase binding affinity by optimizing the structures of IA unit and linkers. These simulations were very much in line with the results of binding assays. Despite this success, neither the chemical affinity assays nor the theoretical modeling predicted much improvement in going from dimer to trimer, yet both cell culture and in vivo studies demonstrated a clear improvement. This demonstrates the inherent risks in extrapolating results from chemical assays to biological systems.

Non-peptide multivalent integrin αvβ3 antagonists have been designed and their therapeutic efficacy evaluated using B16F10 tumor bearing mice. Using molecular modeling approaches, the inventors have shown that the multivalent compounds have one IA unit bound to the original active site with the other parts contacting with residues in vicinity that contributed to the extra binding affinities. Biological study showed that multivalency in these compounds increases their binding affinity and strongly enhances their antiangiogenic and antitumoral efficacy, resulting in slower tumor growth.

Glioblastoma multiforme (GBM) is the most common primary brain tumor, as well as the deadliest (Parsons et al., 2008). Malignant gliomas present some of the greatest challenges in the management of cancer patients worldwide, despite notable recent achievements in oncology. Even with aggressive surgical resections using state-of-the-art preoperative and intraoperative neuroimaging, along with recent advances in radiotherapy and chemotherapy, the prognosis for GBM patients remains dismal. Mean survival after diagnosis is about 1 year (Kanu et al., 2009). Preclinical data indicate that angiogenesis is essential for the proliferation and survival of malignant glioma cells, which suggests that inhibition of angiogenesis, might be an effective therapeutic strategy.

NIRF imaging has been proven to be a very powerful tool for noninvasive imaging of various diseases in preclinical models especially in rodents (Ntziachristos et al., 2003). In an effort to leverage this robust modality, the present inventors have applied NIRF imaging techniques to study an important molecular target, integrin αvβ3, which is expressed by glioblastoma cells. The invention provides imaging and therapeutic agents that are targeted to integrin αvβ3, and can be used for the early detection, treatment, and monitoring of glioblastoma as well as other malignancies.

Computer assisted approaches to identify new inhibitors via pharmacophore, molecular modeling, docking, structural interaction fingerprints is rapidly becoming an integral part of rational approaches to drug design. In silico assessment of the free energy and the binding affinity of receptor-inhibitors prior to synthesis permits sophisticated and efficient methods to design drugs. Hood et al. demonstrated that the integrin antagonist, 4-[2-(3,4,5,6-tetrahydropyrimidine-2-lamino)ethyloxy]benzoyl-2-(S)-amino ethyl sulfonyl-amino-h-alanine (IA) can be used as a targeting agent for gene delivery to tumor neovasculature (2002). A rationally designed bivalent IA by computer modeling could theoretically have better binding affinity and thus greater avidly to target cells expressing this receptor. In an effort to develop the bivalent IA probe for tumor angiogenesis imaging an extensive simulation with varying linker lengths and composition was carried out. The results (summarized in Table 3), demonstrated that bivalent IAs with linkers containing 5 to 8 carbons (n=2~5) exhibited a descending conformational energy while the linker shorter than 5 carbon (n<2) had a significantly higher energy. Based on these simulation results, the 8 carbon linker (n=5) was selected, which has the lowest conformational energy to construct the first bivalent IA. Among various commercially-available linkers, 2-aminododecanedioic acid (which carries two carboxylic acid groups at each end with a total of eight carbons [n=5]) was chosen as the ideal linker for the prototype construct. This analysis predicted that the bivalent IA with an 8-carbon linker (n=5) containing the NIR fluorophore, Cy5.5 dye, would not sterically impact the binding to the integrin protein.

In vitro binding assays have shown that the bivalent IA (IC50=0.40±0.11 nM) exhibited significantly improved integrin αvβ3 affinity when compared to the parent compound IA (IC50=22.33±4.51 nM), resulting in a 50-fold improvement in receptor affinity (IC50) over that of the parent compound IA and a 10-fold improvement over c-[RGDfV] (IC50=4.80±3.01 nM). NIR imaging probe, bivalent-IA-Cy5.5 conjugate also demonstrated significantly increased binding affinity (IC50=0.13±0.02 nM). Fluorescence microscopy studies demonstrated integrin-mediated endocytosis of the bivalent-IA-Cy5.5 conjugate in U-87 cells that was effectively blocked by non-fluorescent bivalent IA. This result provides strong supporting evidence that bivalent-IA-Cy5.5 binds specifically to the αvβ3 integrin receptor expressed on the tumor cell surface.

Systemically administered bivalent-IA-Cy5.5 in tumor-bearing mice resulted in modest accumulation at the tumor site with improved tumor: normal tissue signal over time (up to 48 hrs). This effect was best explained by the relatively slow clearance of the probe from the circulation as evident from the high fluorescence observed throughout the test animals at earlier time points (up to 24 hrs). Consistent with prior studies using a monomeric integrin peptidomimetic conjugated to a chelator for radioisotope imaging, tumor accumulation was time-dependent and required washout from normal tissue for optimal contrast (Burnett et al., 2005). Although the tissue penetration of excitation and emission photons of NIR light is superior to wavelengths of the visible spectrum, a substantial percentage of light is attenuated as a function of tissue depth. Hence, fluorescence measurements likely underestimate the true accumulation of integrin-specific probes at the target tissue.

The experimental results presented here demonstrate the ability to noninvasively image integrin αvβ3 overexpression in live whole animals using a bivalent small molecule with improved receptor binding properties generated by in silico design. A major impetus for the chosen experimental design was to prepare a new class of targeted imaging agents by leveraging known structure activity relationships and in silico modeling to further improve the receptor-binding properties of existing molecules. Prior multivalency studies have clearly shown the utility of expanding the repertoire of drugs by reconfiguring molecules as multimers (Rao et al., 1998; Mulder et al., 2004).

Example 2—Synthesis and Evaluation of Bivalent, Peptidomimetic Antagonists of the $\alpha_v\beta_3$ Integrins Targeting the integrin $\alpha_v\beta_3$ by directly interfering with its function is considered to be an effective and non-cytotoxic strategy for the treatment of tumor. In this example, a series of bivalent analogs of peptidomimetic integrin antagonists IA 1 and IAC 2 were designed, synthesized and evaluated for their ability to inhibit the integrin $\alpha_v\beta_3$. All the bivalent ligands exhibited increased potency compared to that of their monomeric counterparts for the integrin $\alpha_v\beta_3$ with low nanomolar range binding affinity. The best bivalent ligand 6 tested in the series has an $IC_{50}$=0.09 nM evaluated by ELISA assay. The results demonstrate that multivalency is providing a useful template for the development novel integrin $\alpha_v\beta_3$ antagonists as potential therapeutics Materials and Methods All NMR spectra were recorded at 500 or 300 MHz for $^1$H NMR with TMS as an internal standard, and the chemical shifts are given in δ values. Mass spectra was performed on Thermo LCQ-Fleet mass spectrometers. All other solvents were reagent grade.

2-(2-(2-(1H-imidazole-1-carbonyloxy)ethoxy)ethoxy) ethyl 1H-imidazole-1-carboxylate (13) Triethlylene glycol 9 (0.15 g, 1.0 mmol) was dissolved in DCM (5 mL) under nitrogen, and the solution was cooled at 0° C. DIPEA (2.0 mmol) and CDI 12 (0.34 g, 2.1 mmol) were added, and the reaction mixture was stirred at ambient temperature for 6 hr. The mixture was cooled to 0° C., and washed with ice-cold water (2×5 mL), brine (5 mL) The organic phase was dried over NaSO4 (anhydrous), filtered and concentrated under reduced pressure. Purification by silica gel chromatography afforded 13 as a colorless oil (0.277 g, 82%). 1H NMR (300 MHz, CDCl3): 1H NMR (300 MHz, CDCl3): 8.15 (s, 2H), 7.43 (s, 2H), 7.06 (s, 2H), 4.55 (m, 4H), 3.82 (m, 4H), 3.69 (m, 4H).

2-(2-(2-(2-(1H-imidazole-1-carbonyloxy)ethoxy)ethoxy)ethoxy)ethyl 1H-imidazole-1-carboxylate (Compound 14) The procedure was the same as described above as the synthesis of compound 13. Compound 14 was obtained as a colorless oil (0.325 g, 85%). 1H NMR (300 MHz, CDCl3): 1H NMR (500 MHz, CDCl3): 8.37 (s, 2H), 7.44 (s, 2H), 7.07 (s, 2H), 4.55 (m, 4H), 3.82 (m, 4H), 3.51 (m, 8H).

2-(2-(2-(2-(2-(1H-imidazole-1-carbonyloxy)ethoxy)ethoxy)ethoxy)ethoxy)ethyl 1H-imidazole-1-carboxylate (15) The procedure was the same as described above as the synthesis of Compound 13. Compound 15 was obtained as a colorless oil (0.341 g, 80%). 1H NMR (300 MHz, CDCl3): 8.37 (s, 2H), 7.64 (s, 2H), 7.07 (s, 2H), 4.55 (m, 4H), 3.82 (m, 4H), 3.54 (m, 24H).

Compound 3 IA 1 (0.137 g, 0.3 mmol) was dissolved in DMSO (0.5 mL) under nitrogen, and the solution was cooled at 0° C. DIPEA (0.3 mmol) and 13 (0.05 g, 0.15 mmol) were added, and the reaction mixture was heated to 120° C. under microwave irradiation for 30 min. The solvent was then removed and re-crystallized in methanol and acetone (1:1) to give pure Compound 3 as a white solid (0.127 g, 76%). 1H NMR (500 MHz, D2O): 7.68 (d, 4H, J=7.5), 6.96 (d, 4H, J=7.5), 4.21 (m, 3H), 4.10 (m, 6H), 3.79 (m, 3H), 3.56 (m, 18H), 3.24 (s, 12H), 1.82 (s, 4H). MS (ESI, m/z): 1115.41 (100, [M+H]+, calculated: 1114.14.).

Compound 4 The procedure was the same as described above as the synthesis of Compound 3. Compound 4 was obtained as a white solid (0.176 g, 68%). 1H NMR (500 MHz, D2O): 7.68 (d, 4H, J=7.5), 6.95 (d, 4H, J=7.5), 4.22 (m, 3H), 4.10 (m, 6H), 3.78 (m, 3H), 3.56 (m, 22H), 3.24 (m, 12H), 1.82 (s, 4H). MS (ESI, m/z): 1159.25 (100, [M+H]+, calculated: 1158.43).

Compound 5 The procedure was the same as described above as the synthesis of 3. Compound 5 was obtained as a white solid (0.109 g, 61%). 1H NMR (500 MHz, D2O): 7.71 (d, 4H, J=8), 6.99 (d, 4H, J=8), 4.20 (m, 3H), 4.10 (m, 6H), 3.78 (m, 3H), 3.59 (m, 28H), 3.50 (m, 10H), 3.29 (m, 4H), 3.24 (t, 8H, J=5.5), 1.82 (t, 4H, J=5.5). MS (ESI, m/z): 1335.56 (100, [M+H]+, calculated: 1334.54.).

Compound 6 The procedure was the same as described above as the synthesis of 3. The compound 6 was obtained as a white solid (0.144 g, 70%). 1H NMR (500 MHz, D2O): 7.71 (d, 4H, J=8), 6.99 (d, 4H, J=8), 4.18 (m, 9H), 3.79 (m, 3H), 3.64 (m, 11H), 3.48 (m, 10H), 3.29 (m, 12H), 2.92 (m, 3H), 2.67 (s, 2H), 1.82 (t, 4H, J=5.5), 0.78 (s, 12H). MS (ESI, m/z): 1373.42 (100, [M+H]+, calculated: 1372.56.).

Compound 7 The procedure was the same as described above as the synthesis of 3. Compound 7 was obtained as a white solid (0.135 g, 63%). 1H NMR (500 MHz, D2O): 7.70 (m, 4H), 6.99 (m, 4H), 4.18 (m, 9H), 3.78 (m, 3H), 3.66 (m, 15H), 3.48 (m, 10H), 3.24 (m, 12H), 2.90 (m, 3H), 2.67 (s, 2H), 1.82 (s, 4H), 0.78 (s, 12H). MS (ESI, m/z): 1417.56 (100, [M+H]+, calculated: 1416.59.).

Compound 8 The procedure was the same as described above as the synthesis of 3. Compound 8 was obtained as a white solid (0.120 g, 55%). 1H NMR (300 MHz, D2O): 7.71 (m, 4H), 6.99 (m, 4H), 4.13 (m, 8H), 3.75 (m, 3H), 3.60 (m, 28H), 3.49 (m, 12H), 3.24 (m, 14H), 2.92 (m, 3H), 2.72 (s, 2H), 1.82 (s, 4H), 0.78 (s, 12H). MS (ESI, m/z): 1593.47 (100, [M+H]+, calculated: 1592.69.).

Results

Figure 12:
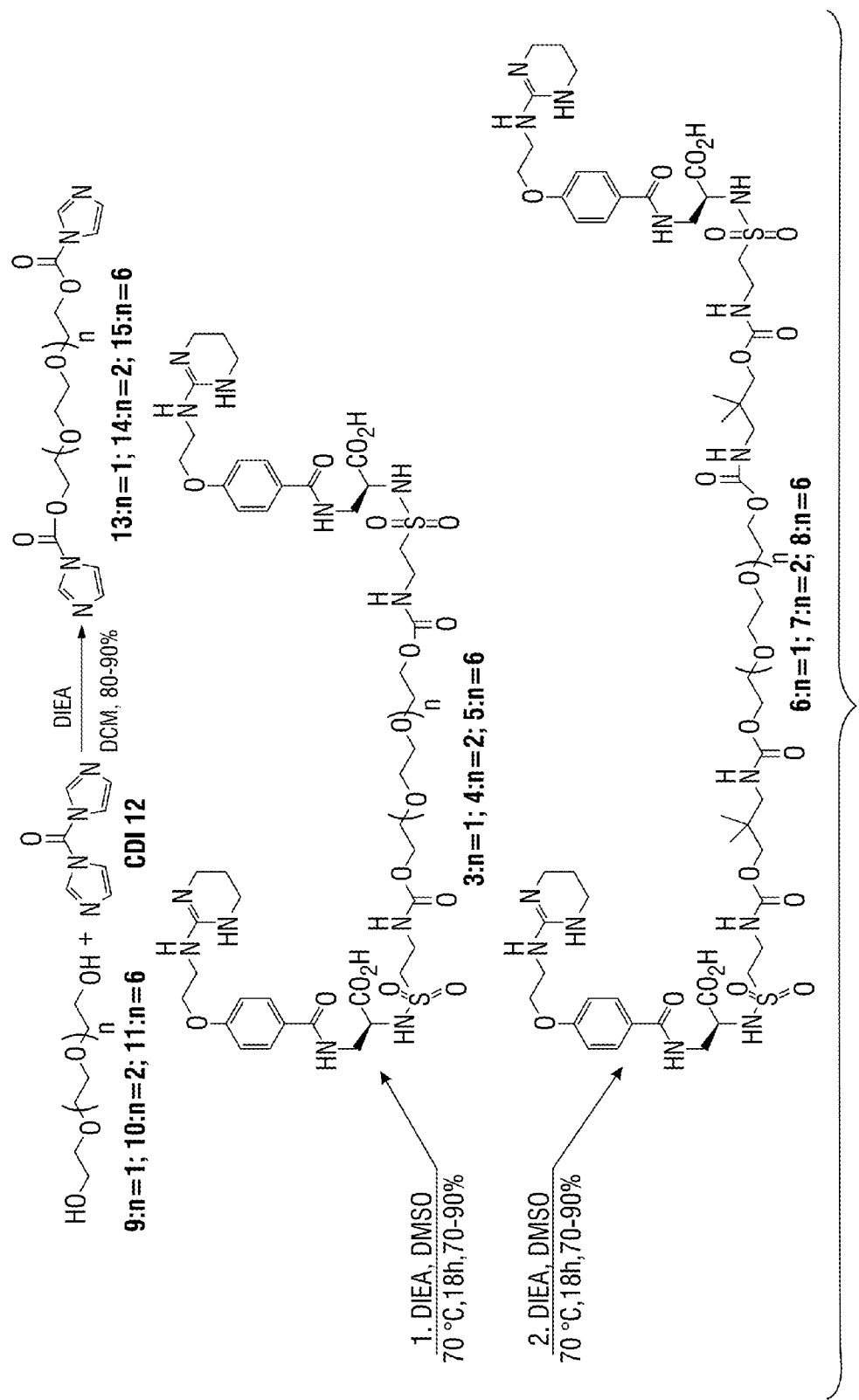
FIG. 12 shows a generalized illustrative synthetic pathway for the synthesis of bivalent ligand compounds (3), (4), (5), (6), (7), and (8) in accordance with one aspect of the present invention.
Figure 13A:
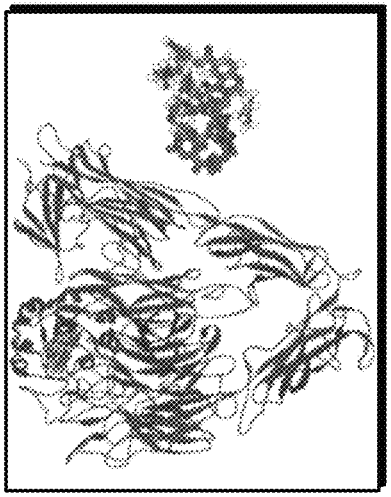
FIG. 13A, FIG. 13B, FIG. 13C, FIG. 13D, FIG. 13E, and FIG. 13F show illustrative examples of the binding of selected antagonists with integrin in accordance with one aspect of the present invention. In each representation, the corresponding structural conformations of the interacting antagonists are offset and enlarged to better show their molecular details.
Figure 13D:
Figure 13B:
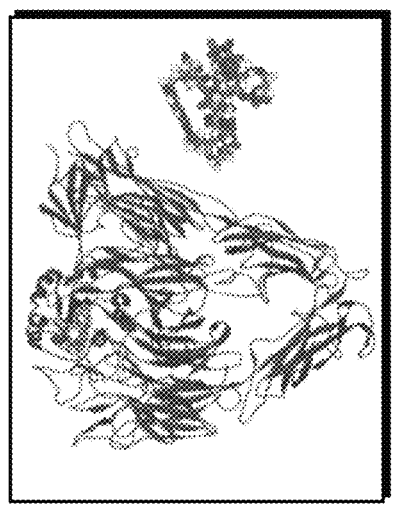
Figure 13E:
Figure 13C:
Figure 13F:
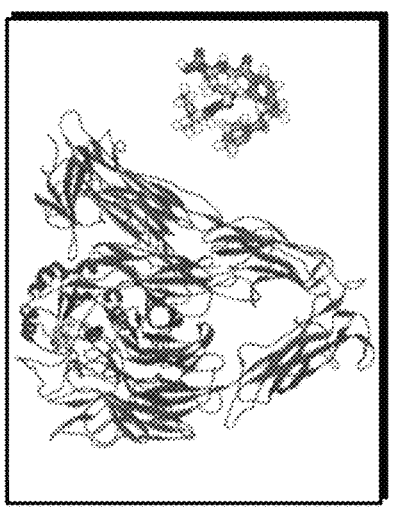
Figure 14:
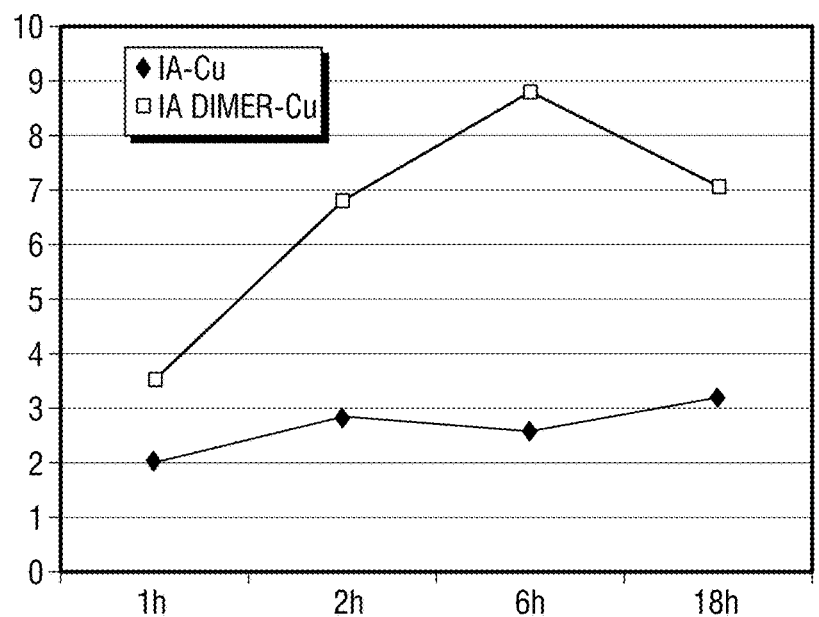
FIG. 14 shows an exemplary quantitative analysis of tumor uptake at different time point after i.v. injection.
Figure 15:
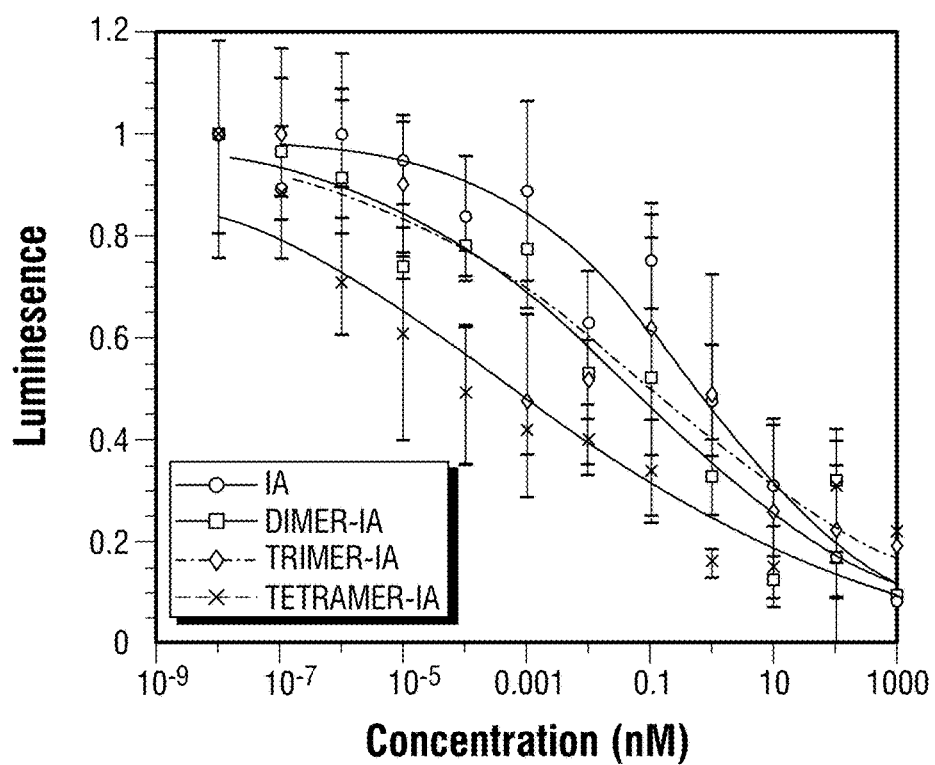
FIG. 15 shows the results of an illustrative ELISA assay of IA, IA Dimer, IA trimer, and IA tetramer.
Figure 16:
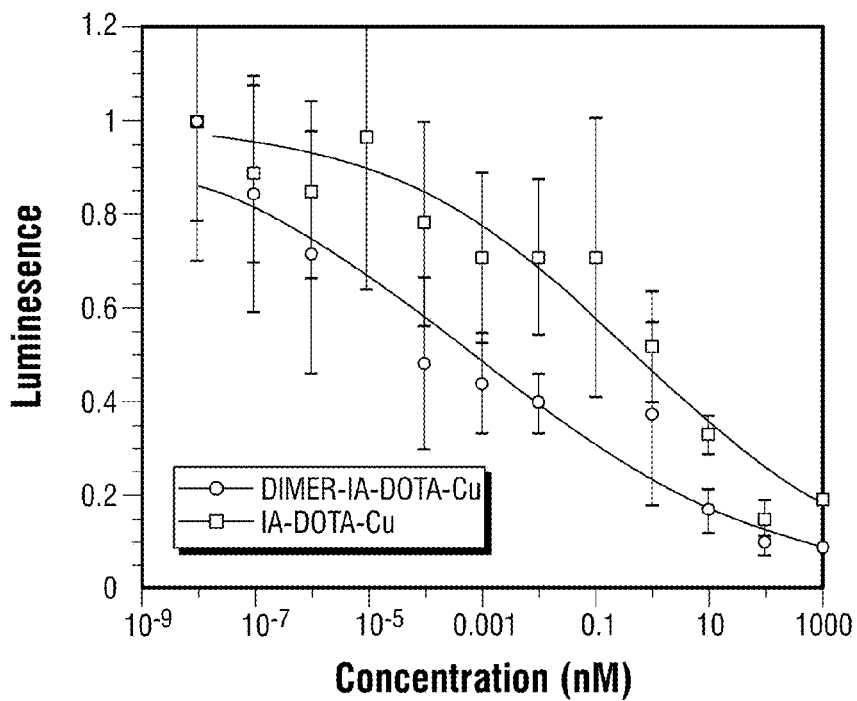
FIG. 16 shows the results of an illustrative ELISA assay for another embodiment of the present invention in which IA monomer DOTA-Cu conjugate (IA-DOTA-Cu) and IA dimer DOTA-Cu conjugate (Dimer-IA-DOTA-Cu) were assayed. All of the points were done in triplicate.
Figure 17A:
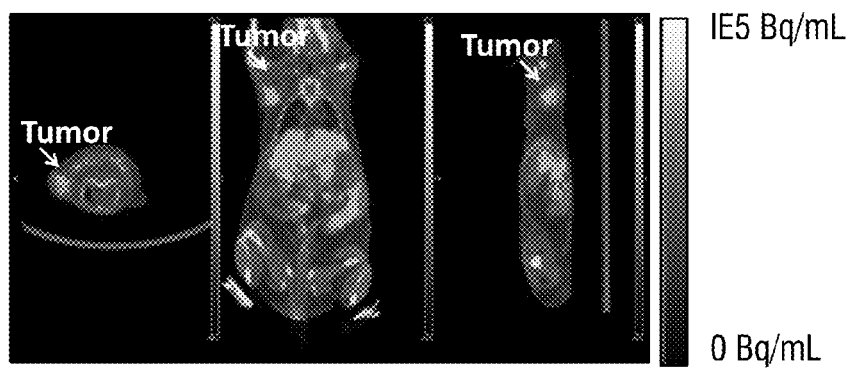
FIG. 17A and FIG. 17B illustrate an integrin targeting Cu-64 PET radiotracer study. Shown are the results of PET imaging (2 hrs' post-imaging) of tumorigenic mice for one illustrative embodiment of the invention. In this study, MicroPET images of M21 tumor-bearing mice at 2 h after intravenous injection of Cu-64 radiolabeled IA dimer and Cu-64 radiolabeled IA monomer were utilized. IA dimer had significantly higher integrin avb3-binding affinity and specificity than IA monomer, Cu-64 radiolabeled IA dimer had higher tumor uptake than Cu-64 radiolabeled IA monomer in the tumor models tested.
Figure 17B:
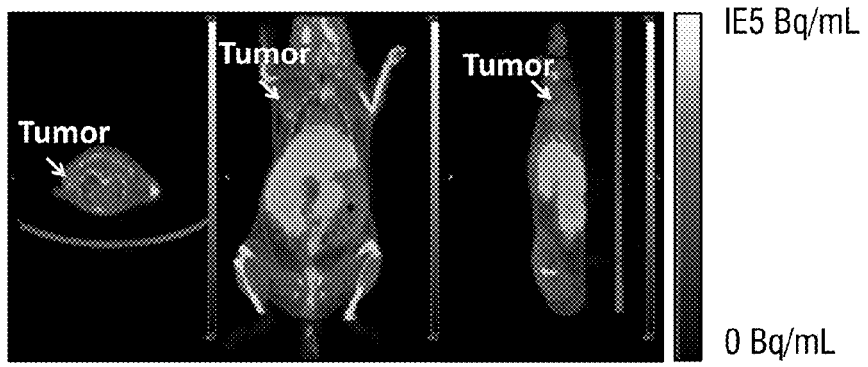
Figure 19:
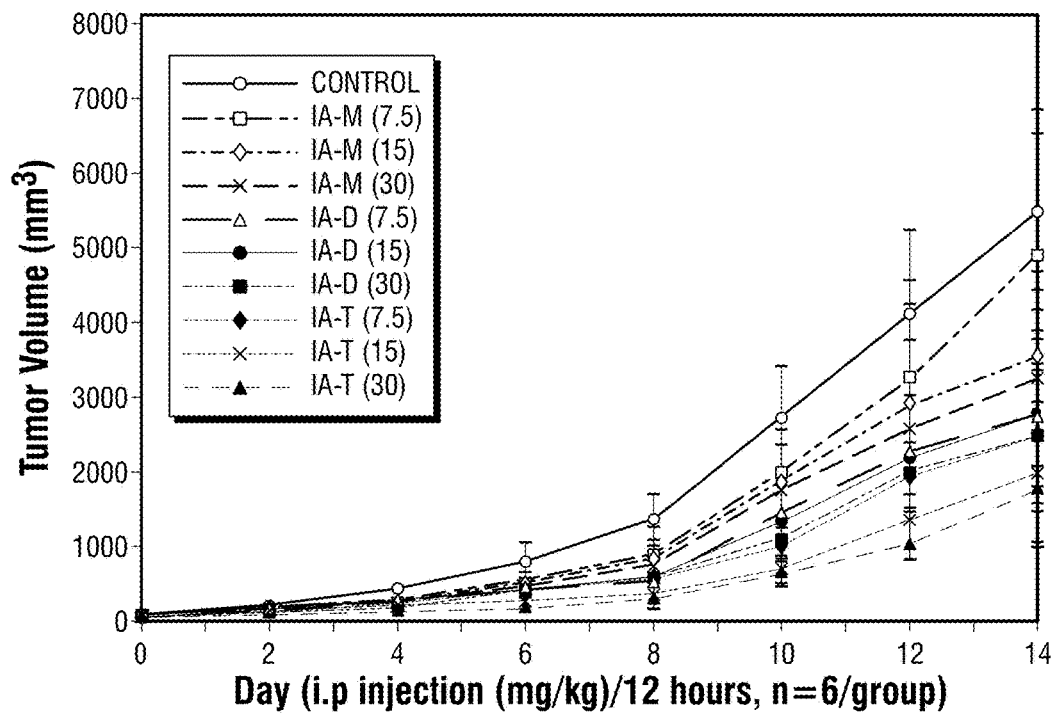
FIG. 19 shows the exemplary antitumor effects of IA-derivatives on a B16F10 melanoma tumor model in accordance with one illustrative aspect of the present invention. In vivo tumor volume after injection of PBS (control), IA monomer (IA-M), IA dimer (IA-D) and IA trimer (IA-T) with 3 dosages respectively (7.5 mg/kg, 15 mg/kg, 30 mg/kg) on B16F10 melanoma tumor bearing mice. Each sample was administered twice per day (once/12 hr) for 14 days.
Figure 20:
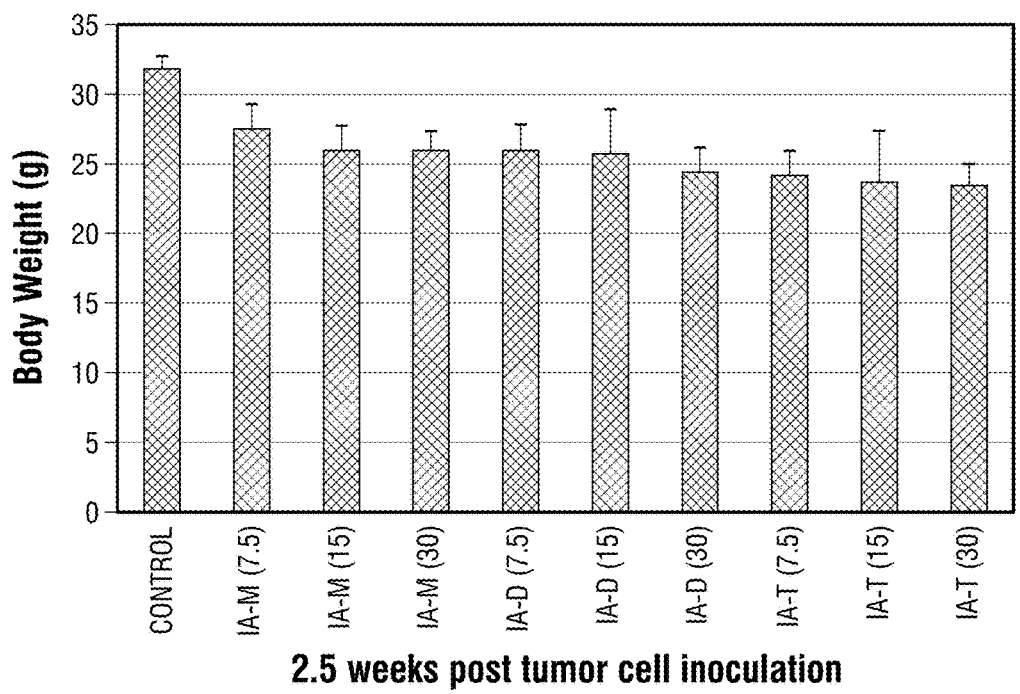
FIG. 20 shows an exemplary study demonstrating in vivo tumor volume after injection of either PBS (control), IA monomer (IA-M), IA dimer (IA-D) or IA trimer (IA-T) using three different dosages (7.5 mg/kg, 15 mg/kg, or 30 mg/kg, respectively) in B16F10 melanoma tumor-bearing mice. Each compound was administered twice per day (every 12 hr) for 14 days.
Figure 21:
FIG. 21 shows exemplary collected tumor tissues in accordance with one aspect of the present invention following 14 days treatment with either IA monomer (IA-M), IA dimer (IA-D), or IA trimer (IA-T)
Figure 22:
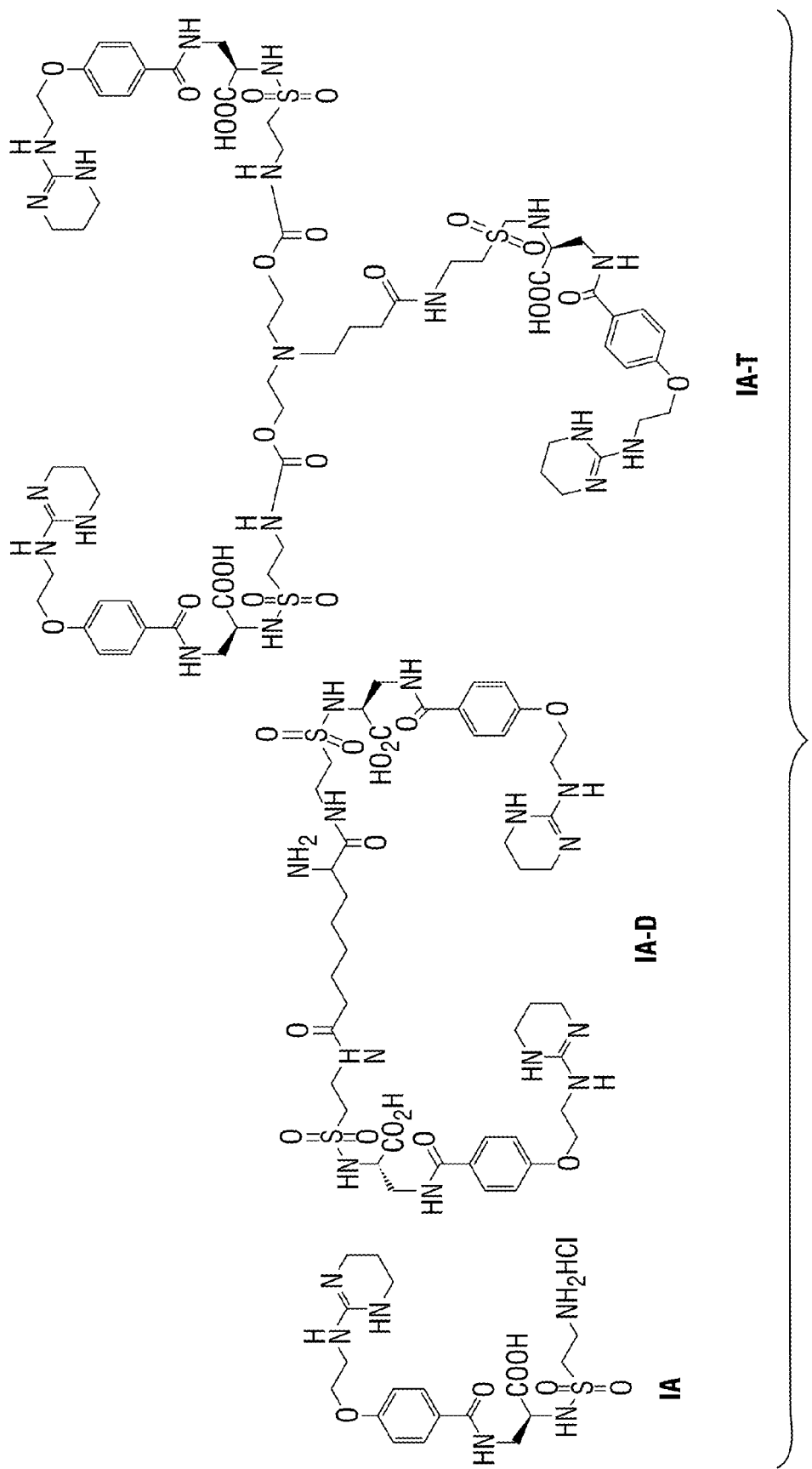
FIG. 22 shows the chemical structures of an exemplary IA monomer (IA), an IA exemplary dimer (IA-D), and an exemplary IA trimer (IA-T) in accordance with one aspect of the present invention.
Figure 23:
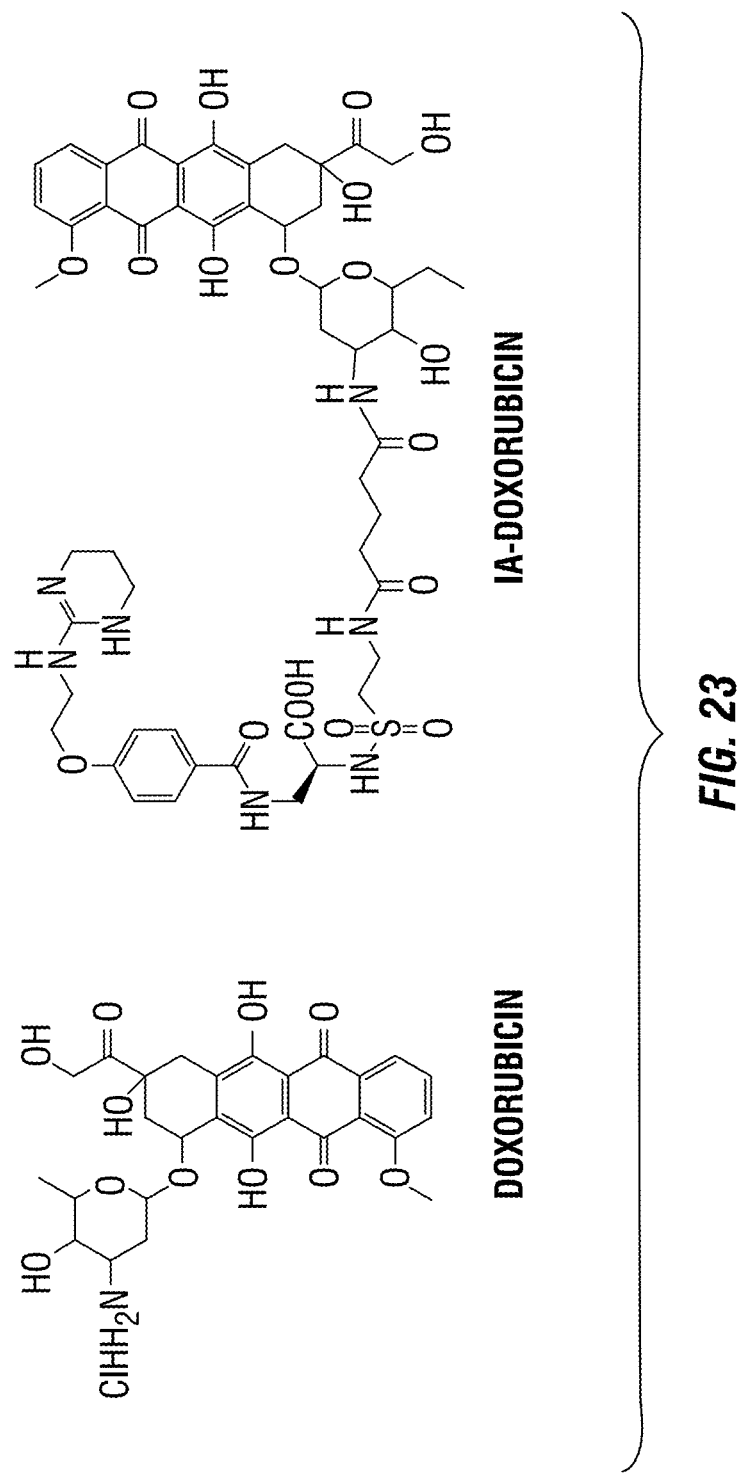
FIG. 23 shows the chemical structure of the chemotherapeutic doxorubicin alone, or bound to IA (IA-doxorubicin)

The bivalent ligands, Compounds 3 through 8 (FIG. 11) were synthesized using the procedure described in FIG. 12, starting with commercially available triethylene glycol 9, tetraethylene glycol 10, and octaethylene glycol 11. The PEGs were first activated as bis-carbonylimidazoles derivatives 13-15, and their chemical structures and purity verified by NMR. The activated alcohols were then coupled to the free amines 1 and 2, respectively in DMSO to provide bivalent ligands 3-8. All compounds were purified to homogeneity by semi-preparative RP-HPLC (Phenomenex C18 column), and their structures were confirmed by NMR and ESI ion trap mass spectrometry.

All final compounds were tested for their ability to competitively inhibit the attachment of the natural ligand vitronectin to purified human $\alpha v\beta 3$ by ELISA assay.

In vitro Binding Affinity Assay. Purified integrin $\alpha v\beta 3$ protein (Chemicon International, Temecula, Calif., USA) was applied to 96-well polystyrene microtiter plates at 1 µg/well. After overnight incubation at 4° C., the plates were washed and then blocked with milk solution (KPL, Inc., Gaithersburg, Md., USA) at room temperature for 2 hr. The blocking buffer was removed, and the plates were inoculated in quadruplicate with bivalent IAs with a typical starting concentration of 125 nM. Serial dilutions were prepared in the 96-well plates using multichannel pipettes. Biotinylated vitronectin solution (0.1 µg/well) was added to each well as a standard competitor.

The plates were incubated at room temperature for 3 hr, washed, and the bound vitronectin was detected using NeutrAvidin-HRP conjugate at 0.01 µg/well (Pierce, Rockford, Ill., USA) and LumiGlo® chemiluminescent substrate system (KPL, Inc.). The luminescence was read using a FLUOstar OPTIMA Microplate Reader (Durham, N.C., USA). The concentration of inhibitor producing 50% inhibition (IC50) of vitronectin binding to $\alpha v\beta 3$ was calculated based on a curve fitting model using KaleidaGraph® 3.5 (Synergy Software, Reading, Pa., USA). It measured competitive binding of the integrin antagonist and biotinylated human vitronectin for the immobilized receptor $\alpha_v\beta_3$. The results are listed in Table 4:

TABLE 4

IN SILICO CONFORMATIONAL ENERGY AND FREE ENERGY OF PEG-LINKED INTEGRIN ANTAGONISTS AND IN VITRO EVALUATION

| Compounds | n | In silico Conformational Energy (kcal/mol) | In silico Free Energy (kcal/mol) | In vitro EL1SA IC$_{50}$, nM$^a$ |
|---|---|---|---|---|
| IA 1 | — | −17.0 (±2.0) | −3.1 (±0.8) | 22.3 (±4.5) |
| IAC 2 | — | −41.5 (±2.0) | −10.2 (±1.6) | 2.07 (±0.9) |
| 3 | 1 | −100.9 (±2.0) | −6.9 (±1.2) | 0.16 (±0.12) |
| 4 | 2 | −98.0 (±2.0) | −6.1 (±1.2) | 0.16 (±0.05) |
| 5 | 6 | −99.3 (±2.0) | −5.7 (±1.2) | 0.16 (±0.10) |
| 6 | 1 | −140.9 (±2.0) | −8.2 (±1.2) | 0.09 (±0.08) |
| 7 | 2 | −138.7 (±2.0) | −1.6 (±0.6) | 0.11 (±0.02) |
| 8 | 6 | −153.4 (±2.0) | −2.1 (±0.6) | 0.32 (±0.09) |

$^a$Values are averages of at least three determinations.

The computer modeling used molecular dynamics (MD) with explicit solvent. In the modeling study, bivalent IA and IAC with varying linker lengths and compositions were constructed and molecular dynamics simulation was performed with CHARMM 35 force field. From calculations of binding energies and ligand spatial distributions, the prediction of favored protein-ligand binding modes, interaction strengths, and binding specificity can be obtained with AutoDock simulations. Ten (10) LGA (Lamarckian genetic algorithm) docking runs were performed for each protein-ligand pair, with each run producing one possible binding mode or solution. The solutions were first sorted in terms of the binding mode, i.e., the position and orientation of the ligand relative to the protein target. The solutions were clustered based on rms (root mean square) deviations in ligand atomic positions, with structures with rmsd of less than 0.5 Å grouped into a cluster. The total number of generated low-energy clusters measures the specificity of binding (Goodsell et al., 1990; Morris et al., 1996; Morris et al., 1998; and Xiong et al., 2002). A small number of clusters indicate that the ligand has only a few possible binding modes and interacts with a specific site (or sites) on the target protein. On the other hand, a large number of clusters imply existence of a wide range of binding modes and lack of specific ligand-target interactions. The second step in sorting solutions involves identification of the solution of lowest binding energy within each cluster and ranking the different clusters according to this energy value. The solution with the lowest energy in the top-ranked cluster and all solutions with energies higher by up to 5.0 kcal/mol were considered as possible binding modes for ligand to target. The docking of each antagonist to the integrin αvβ3 produced 3 clusters out of 10 runs. There were five solutions in the first cluster with an average docking energy of IA, IAC and its dimmers. A summary of the AutoDock results is presented in Table 4 and the docked structures of the first and second clusters are shown in FIG. 13.

In general, all bivalent ligands (3 through 8) showed significantly improved affinity for the $\alpha_v\beta_3$ as compared to the monomer 1 and 2. In particular, bivalent ligands 3 through 5 ($IC_{50}$=0.16 nM) exhibited remarkable potency for the $\alpha_v\beta_3$, and showed 139 fold higher binding affinity as compared to that of the monomer 1 ($IC_{50}$=22.3 nM). Bivalent ligand 6 ($IC_{50}$=0.09 nM) had almost 23-fold higher affinity as compared to the corresponding monomer 2. In fact, 6 is one of the most potent $\alpha_v\beta_3$ antagonists reported to date ($IC_{50}$=0.09 nM). Although the binding affinity of parent monomer 2 is 10 times more potent than monomer 1, the binding affinity of corresponding dimers did not show much difference. This observation suggests that the structure of the parent lead compound is not the only basis for the improved integrin $\alpha_v\beta_3$ binding of the dimers. In view of these results, it is now possible to design multivalent ligands with high binding affinity that are based on weak "parent" compounds. The hypothesis for the significantly-increased binding affinity of dimers as compared to the corresponding monomer was that the local IA concentration was significantly "enriched" in the vicinity of the neighboring integrin $\alpha_v\beta_3$ sites, Once the first IA motif is bound to an integrin $\alpha_v\beta_3$, bivalency may lead to a faster rate of receptor binding and/or a slower rate of dissociation from the receptor. In computer modeling, the binding site defined by the cluster is in the cleft between the RGD binding-domains of integrin $\alpha_v\beta_3$. It was observed that all the ligands stay at that site in the presence of the whole protein. This cluster presented the best model for a possible antagonist interaction to the integrin $\alpha_v\beta_3$. The modeling results suggested that IA dimers should have higher binding affinity than IA monomer because they have lower conformational energy and free energy compared with IA monomer. It also suggested IA dimers with PEGs linker (n=1, 2, or 6) should have similar binding affinity because they have similar energy level in silico. Furthermore, among the bivalent conformations, the simulations suggest that IAC dimer 6 (n=1) has a higher specificity and better fit into the known active site than other conformations. The ELISA results correlates well with these predictions. However, ELISA results may not necessarily correlate perfectly with molecular modeling results. For example, although IAC had the lowest free energy on computer modeling the ELISA result was much less impressive. Without being limited by any particular theory, it appeared that the microscopic reason for these effects was a lack of fit between different IA conformation and the inhibitor/substrate binding site. While the docking results are an approximation, the scoring was based on an empirical energy function, salvation effects treated with a highly simplified model, and only ligand flexibility taken into account, with the protein structure kept fixed (Morris et al., 1996; Morris et al., 1998; and Xiong et al., 2002).

In summary, a series of bivalent antagonists of the $\alpha_v\beta_3$ integrin have been designed and synthesized through tethering IA and IAC with polyethylene glycol, respectively. Biological evaluation of six bivalent ligands shows that all dimers inhibited integrin $\alpha_v\beta_3$ with increased potency as compared to that of their monomeric counterparts IA and IAC. The bivalent ligands 3-5 of IA with different linker length showed similar binding affinity for integrin $\alpha_v\beta_3$ with $IC_{50}$=0.16 nM, 139 times higher in comparison with IA ($IC_{50}$=22.3 nM). In addition, the exemplary bivalent ligand 6 (with a triethylene glycol linker) had the highest binding affinity in the series tested based on ELISA assay ($IC_{50}$=0.09 nM) results.

Example 3—Multivalency of Non-Peptide Integrin $\alpha_v\beta_3$ Antagonists Slowed Tumor Growth To date, more than 200 angiogenesis inhibitors have been reported. These include only a few antiangiogenic peptide drugs. In addition, many molecules upregulated on angiogenic endothelial cells have been explored in the past decades. One of these is integrin $\alpha_v\beta_3$, which recognizes RGD (Arg-Gly-Asp) motifs in extracellular protein components. Targeting the $\alpha_v\beta_3$ integrin with drugs may provide an opportunity to destroy tumor vessels without harmful effects on microvessels of normal tissues.

Multivalency is a powerful strategy for achieving high-affinity molecular binding of compounds to increase their therapeutic potency or imaging potential. In this example, multivalent non-peptide integrin $\alpha_v\beta_3$ antagonists (IA) were designed for anti-tumor therapy. Docking and molecular dynamics were employed to explore the binding modes of IA monomer, dimer and trimer. In silico, one IA unit binds tightly in the active site with similar pose to native ligand RGD and other parts of dimer and trimer contribute extra binding affinities by interacting with residues in vicinity of the original site. In vitro studies demonstrated that increasing valency results in increasing anti-proliferative and anti-organizational effects against endothelial cells (HUVECs), and a much weaker effect on melanoma B16F10 cells. The anti-tumor efficacies of the IA multivalent compounds were evaluated in subcutaneous B16F10 melanoma tumor-bearing mice. At 30 mg/kg dose, the mean masses of tumors harvested 18 days after inoculation were reduced by 36±9%, 49±8%, and 71±7% for the IA-monomer, dimer, and trimer groups, relative to control. The importance of multivalency was demonstrated to be highly significant beyond the additive effect of the extra pharmacological sites (p=0.00011). These results suggest that the major target of these anti-αvβ3 compounds is the neovasculature rather than the cancer cells, and the success of a multivalent strategy depends on the details of the components and linker. This is the first integrin αvβ3 multivalent ligand showing clear enhancement in anti-tumor effectiveness.

In the present study, a multivalent nonpeptide integrin αvβ3 antagonist (multivalent IA, 4-[2-(3,4,5,6-tetrahydropyrimidine-2-ylamino)ethyloxy]benzoyl-2-(S)-aminoethylsulfonyl-amino-halanine monomer, dimer and trimer) was synthesized, and its anti-tumor therapeutic potential assayed. The anti-tumor efficacies of the IA multivalent compounds were evaluated in B16F10 melanoma tumor-bearing mice. Tumors were inoculated subcutaneously and allowed to progress before treating. IA compounds were given by intraperitoneal injection every 12 hours for 14 days. It was observed that 30 mg/kg of IA-trimer showed higher antitumor efficacy and lower toxicity compared to IA-Monomer and IA-Dimer, as shown by changes in tumor volume against control group (IA-Trimer: 32.05%>IA-Dimer: 45.33%>IA-Monomer: 59.29%>PBS:=100%).

In this example, IA was used as a parent compound, and multivalent ligands were constructed to mimic, compete with, and/or inhibit natural interactions. The anti-tumor efficacies of the IA multivalent compounds were evaluated in tumor bearing mice. The results showed that multivalency in these compounds strongly enhanced their anti-angiogenic and anti-tumoral efficacy.

Materials and Methods

All solvents and reagents were purchased from commercial sources and used without further purification. $^1$H NMR data were recorded on a Bruker Ultrashield 500 instrument at 500 MHz for proton using $CDCl_3$-$d_6$ or $D_2O$. Chemical shifts were reported in ppm ($\delta$) downfield of tetramethylsilane and coupling constants were given in hertz. The purification of the crude product was carried out on a semi-preparative reversed-phase high-performance liquid chromatography (HPLC) system equipped with a diode array UV-vis absorbance detector (Agilent 1200 HPLC system). Mass spectral data were recorded on a Thermo Finnigan LCQ Fleet using electrospray as the ionization method.

Synthesis of IA Dimer.

To a solution of the 2-(((9Hfluoren-9-yl)methoxy)carbonylamino)octanedioic acid (100 mg, 0.24 mmol) in EtOAc (20 mL), dicyclohexylcarbodiimide (110 mg, 0.53 mmol), and N-hydroxysuccinimide (60 mg, 0.52 mmol) were added at 0° C. The mixture was stirred at 0° C. for 8 hr (detected by TLC). Solvent was evaporated under reduced pressure to get the crude intermediate. The intermediate was dissolved in DMSO (9 mL) for next step reaction without further purification. To this DMSO solution, IA (250 mg, 0.50 mmol) and diisopropylethylamine (0.2 mL, 1 mmol) were added, and the mixture was stirred at ambient temperature for 24 hr. After removing solvent at reduced pressure, 10 mL of water was added, and the white solid was removed by filtration. The aqueous solution was lyophilized, and the residue re-crystallized in methanol and acetone (1:3) to give pure bivalent IA 3 with 50% yield as a white solid. 1H NMR (300 MHz, D2O): 7.65 (m, 4H), 6.93 (m, 4H), 4.16 (m, 7H), 3.84 (m, 4H), 3.30 (m, 10H), 3.21 (m, 10H), 2.05 (t, 2H, J 7.0 Hz), 1.80 (m, 6H), 1.43 (m, 2H), 1.18 (m, 4H). MS (electrospray): m/z 1066.3 (100, [M+H]+, calculated 1065.4.).

Synthesis of IA Trimer

Triethylamine (4.0 mL, 28 mmol) was added to a stirred solution of triethanol amine (0.45 g, 3 mmol) in anhydrous CH2Cl2 (50 mL) 1,1'-carbonyldiinidazole (CDI, 4.06 g, 24 mmol) was added and the mixture was stirred at room temperature for 12 h and the reaction was quenched by adding 50 mL water. The organic phase was separated and dried over MgSO4. Solvent was evaporated under reduced pressure to get the crude intermediate 2,2',2"-nitrilotris(ethane-2,1-diyl)tris(1H-imidazole-1-carboxylate) (1.16 g, 2.69 mmol, 90%) as a colorless oil. IA (100 mg, 0.20 mmol) was added to a solution of 2,2',2"-nitrilotris(ethane-2,1-diyl) tris(1H-imidazole-1-carboxylate) (30 µL, 0.03 mmol) in DMSO (2 mL). Triethylamine (0.1 mL, 0.70 mmol) was added and the mixture was stirred overnight at ambient temperature, the reaction was quenched by adding 200 µL of trifluoroacetic acid (TFA). The purification of the crude product was carried out on a HPLC. The peak containing the IA trimer was collected, lyophilized and stored in the dark at −20° C. until use. 1H NMR (500 MHz, D2O): 7.55 (d, 6H, J=8.4), 6.81 (d, 6H, J=8.4), 4.20 (m, 8H), 3.99 (m, 6H), 3.70 (m, 3H), 3.37 (m, 22H), 3.16 (t, 6H, J=6), 3.13 (m, 12H), 1.70 (m, 6H). The ms spectrum of IA trimer: m/z 1596.4 ([M+H]+, calculated 1595.6.).

Assay of In Vitro Cytotoxicity.

Mouse melanoma B16F10 cells (Caliper.CO,) and human melanoma M21 cells were maintained in RPMI 1640 (Caliper) containing 10% (vol./vol.) fetal bovine serum (Invitrogen, Ontario, Canada), 100 U/mL penicillin G, and 100 µg/mL streptomycin for general cell growing condition. For cell cytotoxicity assay, the cells were then seeded into 96-well flat-bottomed tissue-culture plates at $1 \times 10^4$ cells/well and incubated for 24 hr or 72 hr in humidified atmosphere of 5% (vol./vol.) $CO_2$ at 37° C. in the presence of each compound. The multivalent compounds (monomer, dimer, trimer) sample solutions were diluted with culture medium (1% FBS added) to obtain the concentration of each compound in the range of 0.1 to 100 µg/mL. The cytotoxic effects of monomer, dimer and trimer compounds solution were evaluated by adding a mixture of 100 µL of each sample and 100 µL of culture medium to each well. After 24-hr or 72-hr incubation, cell viability was evaluated by mitochondrial conversion of 3-(4,5-dimethylthiazol-2-yl)-2, 5-diphenyl tetrazolium bromide (MTT assay).

In Vivo Antitumor Efficacy of IA Multivalent Compounds.

All animal procedures were approved by the appropriate regulatory agencies. The therapeutic test for antitumor efficacy of IA multivalent compounds was evaluated using tumor-bearing mice that were prepared by the subcutaneous injection in the dorsa of nu/nu female mice (6 weeks old; 20-25 g). The mouse melanoma cancer cell line B16F10 was obtained from Caliper, and tested negative for rodent pathogens. The cells were maintained in vitro as described above. Mice were inoculated with a suspension of $1 \times 10^6$ B16F10 cells in 100 µL complete medium (10% FBS added). Four days after subcutaneous inoculation (the tumor diameter was approximately 5-8 mm, the tumor volume was approximately 50 to 100 $mm^3$), tumor-bearing mice (n=7 per group) were inoculated intraperitoneally (i.p.) with each IA compound (Monomer, Dimer, Trimer) in PBS or PBS alone for control group. All compounds were serially diluted with PBS and were given 2 times per day (every 12 hr) so that compounds doses would be 100 µL of 7.5, 15, 30 mg/kg (maximum tolerated dose) for 14 days. The tumor size was calculated as:

$$a \times b2/2,$$

where a is the largest and b the smallest diameter.

In addition, the survival and body weight of the mice were recorded.

Statistics.

The statistical significance of differences between experimental and control groups was determined using one-way ANOVA. P<0.05 was considered significant, and significant differences are shown by asterisks in the relevant drawings.

Results

Biological Activity of IA Multivalent Agents In Vitro.

The in vitro biological activities of exemplary monomer IA, dimer IA, and trimer IAs were characterized by cell cytotoxicity assays. The cytotoxicity of each compound was evaluated using an MTT colorimetric assay. Results demonstrated these 3 types of IA derivatives showed little toxicity against the B16F10 tumor cell line, although IA-monomer and IA-dimer did not show as much toxicity as the IA-trimer. Less than 90% of the cells were viable after a 1-day exposure to 10 µg/mL IA-trimer, whereas more than 99% of the cells remained viable when exposed to same concentration of IA-monomer and IA-dimer. At higher concentration, cell viability was reduced to 80% for the IA-trimer (100 µg/mL), but there were no significant changes of cell viability in the IA-monomer or IA-dimer.

In Vivo Antitumor Therapeutic Effect.

The in vivo antitumor efficacies of IA derivatives, IA-monomer and IA-dimer with IA-trimer were studied in B16F10 tumor-bearing mice. The inventors theorized that such a therapeutic effect, if detected in vivo, would point to an indirect mechanism of action rather than direct killing of cancer cells themselves, since the in vitro toxicity of the compounds themselves against B16F10 was very low. Mice were treated with PBS, IA-monomer, IA-dimer, IA-trimer administered by intraperitoneal injection to 10 groups (n=7). The dose of IA derivatives in each sample was 7.5 mg/kg, 15 mg/kg, 30 mg/kg, and each sample was administered twice per day (once/12 hr) for 2 weeks. The results obtained indicated that no significant differences in tumor sizes were observed in control animals receiving PBS. However, group receiving IA derivatives showed powerful tumor suppression. By 14-days' post-injection, the average tumor volume in 15 mg/kg IA-trimer compound-treated mice had increased relatively slowly and attained only 2000 mm$^3$ (for 30 mg/kg IA-trimer treated animals, only 1800 mm$^3$ tumor volume was observed). These results were less than one-third of the average tumor volumes recorded in vehicle (PBS)-treated control mice. The tumor volume showed a statistically-observable, dose-dependent pattern for each of the three compounds: IA-monomer, IA-dimer, and IA-trimer. Among these three test compounds, the average tumor size in the IA-trimer group was significantly smaller (2.3-fold or 1.7-fold) than the tumor size in the IA-monomer and IA-dimer groups, respectively. Tumor volume in the IA-trimer test group reached average volume of 2000 mm$^3$, while those of the IA-dimer and IA-monomer and control animals attained 3000 mm$^3$, 5000 mm$^3$ and 6000 mm$^3$, respectively. In collected tumor tissues, the size was demonstrably dose- and group-dependent. Before sacrifice, the mice body weights showed no significant change except in the control animal group. Only two mice died in the PBS injected control group within 12 days due to excessive tumor burden, while in the mouse groups receiving IA-monomer, IA-dimer, IA-trimer, all of animals survived for at least 2 weeks. Thus, despite the low expected cell toxicity, the IA derivatives showed demonstrable anti-tumor effectiveness dependent on both drug dose and multivalency.

Discussion

Integrins are the key regulators of tumor angiogenesis and metastasis. The large collection of literature that reports on anti-angiogenic cancer therapy based on integrin antagonism confirms the utility of integrin $\alpha_v\beta_3$ as an anti-cancer target. Targeting tumor vasculature in cancers with antiangiogenic peptides is promising way forward both for tumor therapy and tumor imaging because it is known that tumor microvessels over-express specific target molecules, particularly integrins such as $\alpha v\beta 3$. Small peptides containing RGD sequences have been developed to target $\alpha v\beta 3$ integrin on angiogenic endothelium; such peptides offer an exciting strategy for delivering cytotoxic drugs and radiolabeled or fluorophore-labeled imaging probes to tumors in projects involving cancer therapy and imaging. The main disadvantage of these small RGD peptides, however, is that they show rapid renal clearance in rodents and humans. This is likely also true of the small molecule compounds tested herein, a fact that led the inventors to impose the rather harsh regimen of 12-hr i.p. injections carried out over 2 weeks in order to demonstrate a significant therapeutic effect.

In anti-angiogenic therapies, one of the most specific targets is the $\alpha v\beta 3$ integrin, which is found on the luminal surface of endothelial cells and mediates many cell processes including cell migration, invasion, proliferation, angiogenesis, and metastasis. To efficiently deliver $\alpha v\beta 3$ integrin antagonists to tumors, as next step, the inventors have prepared and characterized an intraperitoneal formulation for non-peptidic integrin multivalent delivery using integrin antagonist (IA) to improve high therapeutic efficiency in vivo evaluation. In this study, non-peptidic integrin antagonists were prepared using modified bivalent compounds, and the monomer, dimer and trimer forms were evaluated. The results showed prolonged and sustained release of IA for at least 2 weeks. Multivalent IA displayed anti-tumoral efficacy by inhibiting $\alpha v\beta 3$ integrin in vivo. Among those (IA-monomer, IA-dimer and IA-trimer), IA-trimer markedly suppressing $\alpha v\beta 3$ integrin induced angiogenesis as well as by decreasing tumor suppress in therapeutic effect by IA-monomer and IA-dimer in vivo. Multivalent IA via intraperitoneal administration significantly decreased tumor growth compared to control PBS injected either intraperitoneally. The small RGD peptide analogs mainly accumulate in liver, kidney, and spleen, and these organs are closely associated with the rapid and enhanced clearance of the analogs. However, in the present study, only $\alpha v\beta 3$ antagonist multivalent IA derivatives were used and these multivalent IA derivatives were shown to be an efficient in viva therapeutic system. Based on the results obtained in these studies, it was concluded that multivalent IAs, including the compounds described herein represent valuable anti-angiotherapeutic agents, and offer improved local and regional tumor therapies, particularly when compared to RGD peptide-based methods.

TABLE 5

BINDING FREE ENERGIES (KCAL/MOL), IC$_{50}$ (NM) OF IA, IA DIMER AND IA TRIMER TO INTEGRIN A$_v$B$_3$

| IA Ligand | Binding Free Energy | | IC$_{50}$ (nM) |
|---|---|---|---|
| | GB/SA | PB/SA | ELISA |
| IA | −46.5 ± 6.1 | −43.5 ± 7.3 | 11.00 ± 2.49 |
| IA dimer | −68.9 ± 5.7 | −72.2 ± 8.2 | 0.44 ± 0.13 |
| IA trimer | −97.6 ± 6.2 | −64.5 ± 7.5 | 0.22 ± 0.09 |

6. REFERENCES

The following references, to the extent that they provide exemplary procedural or other details supplementary to those set forth herein, are specifically incorporated herein in their entirety by express reference thereto:

Allison, R C et al., "Thermodilution measurement of lung water," *Clin. Chest Med.,* 6:439-457 (1985).

Arap, W. et al., "Cancer treatment by targeted drug delivery to tumor vasculature in a mouse model," *Science,* 279: 377-380 (1998).

Bernard, B et al., "Radiolabeled RGD-DTPA-Tyr3-octreotate for receptor-targeted radionuclide therapy," *Cancer Biother. Radiopharm.,* 19(2):173-80 (2004).

Bradbrook, M et al., "X-ray and molecular dynamics studies of concanavalin-A glucoside and mannoside complexes; relating structure to thermodynamics of binding," *J. Chem. Soc., Faraday Transact.*, 94(11):1603-1611 (1998).

Brooks, P C et al., "Requirement of vascular integrin $\alpha_v\beta_3$ for angiogenesis," *Science*, 264:569-571 (1994).

Broxterman, H J et al., "Resistance to cytotoxic and anti-angiogenic anticancer agents: similarities and differences," *Drug Resist. Updat*, 6(3):111-127 (2003).

Burnett, C A et al., "Synthesis, in vitro, and in vivo characterization of an integrin $\alpha V\beta 3$-targeted molecular probe for optical imaging of tumor," *Bioorg. Med. Chem.*, 13:3763-3771 (2005).

Capello, A et al., "Increased cell death after therapy with an Arg-Gly-Asp-linked somatostatin analog," *J. Nucl. Med.*, 45(10):1716-20 (2004).

Case, D A et al., "AMBER 11. University of California, San Francisco 2010.

Chen, K and X. Chen, "Integrin targeted delivery of chemotherapeutics," *Theranostics*, 1:189-200 (2011).

Chen, X et al., "In vivo near-infrared fluorescence imaging of integrin $\alpha_v\beta_3$ in brain tumor xenografts," *Cancer Res.*, 64:8009-8014 (2004).

Chen, X et al., "Integrin $\alpha v\beta 3$-targeted imaging of lung cancer," *Neoplasia*, 73:271-279 (2005).

Chen, X et al., "MicroPET and autoradiographic imaging of breast cancer $\alpha v$-integrin expression using $^{18}$F- and $^{64}$Cu-labeled RGD peptide," *Bioconjug. Chem.*, 15(1):41-49 (2004).

Chen, X et al., "MicroPET imaging of brain tumor angiogenesis with 18F-labeled PEGylated RGD peptide," *Eur. J. Nucl. Med. Mol. Imaging*, 31(8):1081-1089 (2004).

Chen, X et al., "Pegylated Arg-Gly-Asp peptide: $^{64}$Cu labeling and PET imaging of brain tumor $\alpha v\beta 3$-integrin expression," *J. Nucl. Med.*, 45(10):1776-1783 (2004).

Chen, X et al., "Pharmacokinetics and tumor retention of 125I-labeled RGD peptide are improved by PEGylation," *Nucl. Med. Biol.*, 31(1):11-19 (2004).

Chen, X et al., MicroPET imaging of breast cancer $\alpha v$-integrin expression with 64Cu-labeled dimeric RGD peptides," *Mol. Imaging. Biol.*, 6(5):350-359 (2004).

Chen, X, "Integrin targeted imaging and therapy," *Theranostics*, 1:28-29 (2011).

Cheng, Z et al., "Near-infrared fluorescent deoxyglucose analogue for tumor optical imaging in cell culture and living mice," *Bioconjug. Chem.*, 17:662-669 (2006).

Cheng, Z et al., "Near-infrared fluorescent RGD peptides for optical imaging of integrin $\alpha V\beta 3$ expression in living mice," *Bioconjug. Chem.*, 16:1433-41 (2005).

Cieplak, P et al., "Application of the multimolecule and multiconformational RESP methodology to biopolymers: Charge derivation for DNA, RNA, and proteins," *J. Comput. Chem.*, 16(11):1357-1377 (1995).

Conforti, G et al, "Human endothelial cells express integrin receptors on the luminal aspect of their membrane," *Blood*, 80(2):437-46 (1992).

Darden, T et al., "Particle Mesh Ewald—an NLog(N) method for Ewald sums in large systems,"*J. Chem. Phys.*, 98(12):10089-10092 (1993).

Delbaldo, C et al., "Phase I and pharmacokinetic study of etaracizumab (Abegrin), a humanized monoclonal antibody against $\alpha v\beta 3$ integrin receptor, in patients with advanced solid tumors," *Invest. New Drugs*, 26:35-43 (2008).

DeNardo, S J et al., "Neovascular targeting with cyclic RGD peptide (cRGDf-ACHA) to enhance delivery of radioimmunotherapy," *Cancer Biother. Radiopharm.*, 15(471-79 (2000).

Duan, Y et al., "A point-charge force field for molecular mechanics simulations of proteins based on condensed-phase quantum mechanical calculations," *J. Comput. Chem.*, 24(16): 1999-2012 (2003).

Dupradeau, F-Y et al., "The R.E.D. tools: advances in RESP and ESP charge derivation and force field library building," *Phys. Chem. Chemical Phys.*, 12(28):7821-7839 (2010).

Folkman, J, "Angiogenesis in cancer, vascular, rheumatoid and other disease," *Nat. Med.*, 1:27-31 (1995).

Garanger E et al., "Tumor targeting with RGD peptide ligands-design of new molecular conjugates for imaging and therapy of cancers," *Anticancer Agents Med. Chem.*, 7(5):552-8 (2007).

Gestwicki, J E et al., "Influencing receptor-ligand binding mechanisms with multivalent ligand architecture," *J. Am. Chem. Soc.*, 124:14922-14933 (2002).

Gilbert, M R et al., "Cilengitide in patients with recurrent glioblastoma: the results of NABTC 03-02, a phase II trial with measures of treatment delivery," *J. Neurooncol.*, 106(1):147-53 (2011).

Goncalves, V et al., "Rational design, structure, and biological evaluation of cyclic peptides mimicking the vascular endothelial growth factor," *J. Med. Chem.*, 50:5135-5146 (2007).

Goodsell, D S and Olson, A J, "Automated docking of substrates to proteins by simulated annealing," *Proteins*, 8:195-202 (1990).

Guerrero, C A et al, "Integrin alpha(v)beta(3) mediates rotavirus cell entry," *Proc. Natl. Acad. Sci. USA*, 97:14644-14649 (2000).

Halekoh, V et al., "The R Package geepack for Generalized Estimating Equations (2) *J. Stat. Soft.*, 15(2):1-11 (2006).

Harris, T D et al., "Design, synthesis, and evaluation of radiolabeled integrin $\alpha v\beta 3$ receptor antagonists for tumor imaging and radiotherapy," *Cancer Biother, Radiopharm.*, 18(4):627-641 (2003).

Haubner R et al., "Radiolabeled $\alpha v\beta 3$ integrin antagonists: a new class of tracers for tumor targeting," *J. Nucl. Med.*, 40(6):1061-1071 (1999).

Haubner, R et al, "Glycosylated RGD-containing peptides: tracer for tumor targeting and angiogenesis imaging with improved biokinetics," *J. Nucl. Med.*, 42(2):326-336 (2001).

Haubner, R et al., "Radiolabeled $\alpha_v\beta_3$ integrin antagonists: a new class of tracers for tumor targeting," *J. Nucl. Med.*, 40(6):1061-1071 (1999).

Haubner, R et al., "Synthesis and biological evaluation of a $^{99m}$Tc-labelled cyclic RGD peptide for imaging the $\alpha v\beta 3$ expression," *Nuklearmedizin*, 43(1):26-32 (2004).

Haubner, R et al., "Structural and functional aspects of RGD-containing cyclic pentapeptides as highly potent and selective integrin antagonists," *J. Am. Chem. Soc.*, 118:7461-7472 (1996).

Honig, B and Nicholls, A "Classical electrostatics in biology and chemistry," *Science*, 268(5214):1144-1149 (1995).

Hood, J D et al., "Tumor regression by targeted gene delivery to the neovasculature," *Science*, 296:2404-2407 (2002).

Hynes, R O, "Integrins: versatility, modulation, and signaling in cell adhesion" *Cell*, 69(1):11-25 (1992).

Izaguirre, J et al., "Langevin stabilization of molecular dynamics," *J. Chem. Phys.*, 114(5):2090-2098 (2001).

Janssen, M et al., "Improved tumor targeting of radiolabeled RGD peptides using rapid dose fractionation," Cancer Biother. Radiopharm., 19(4):399-404 (2004).

Jorgensen, W et al., "Comparison of simple potential functions for simulating liquid water," J. Chem. Phys., 79(2): 926-935 (1983).

Kanu, O O et al., "Glioblastoma multiforme: a review of therapeutic targets," Expert Opin. Ther. Targets, 13(6): 701-18 (2009).

Kim J H et al., "Self-assembled glycol chitosan nanoparticles for the sustained and prolonged delivery of antiangiogenic small peptide drugs in cancer therapy," Biomaterials, 29(12):1920-30 (2008).

Kollman, P A et al., "Calculating structures and free energies of complex molecules: combining molecular mechanics and continuum models," Accounts Chem. Res., 33(12): 889-897 (2000).

Li, F et al., "Synthesis and evaluation of a near-infrared fluorescent non-peptidic bivalent integrin alpha(v)beta(3) antagonist for cancer imaging," Bioconjugate Chem., 21:270-278 (2010).

Liu, Z et al., "(68)Ga-labeled cyclic RGD dimers with Gly3 and PEG4 linkers: promising agents for tumor integrin alphavbeta3 PET imaging," Eur. J. Nucl. Med. Mol. Imaging, 36(6):947-57 (2009).

Magrath, I T, "Targeted approaches to cancer therapy," Int. J. Cancer, 56(2):163-166 (1994).

Mammen, M et al., "Polyvalent Interactions in Biological Systems: Implications for Design and Use of Multivalent Ligands and Inhibitors," Angew. Chem. Int. Ed., 37:2754-2794 (1998).

Mittra, E S et al., "Pilot pharmacokinetic and dosimetric studies of $^{18}$F-FPPRGD2: a PET radiopharmaceutical agent for imaging alpha(v)beta(3) integrin levels," Radiology, 260(1):182-91 (2011).

Morris, G M et al., "Automated docking using a Lamarckian genetic algorithm and empirical binding free energy function," J. Comput. Chem., 19:1639-1662 (1998).

Morris, G M et al., "Distributed automated docking of flexible ligands to proteins: parallel applications of AutoDock 2.4," J. Comput. Aided Mol. Des., 10:293-304 (1996).

Mulder, A et al., "Multivalency in supramolecular chemistry and nanofabrication. Org. Biomol. Chem., 2:3409-24 (2004).

Nabors, L B et al., "A safety run-in and randomized phase 2 study of cilengitide combined with chemoradiation for newly diagnosed glioblastoma (NABTT 0306)," Cancer, 118(22):5601-5607 (2012).

Noiri E et al., "Biodistribution and clearance of 99 mTc-labeled Arg-Gly-Asp (RGD) peptide in rats with ischemic acute renal failure," J. Am. Soc. Nephrol., 7:2682-2688 (1996).

Ntziachristos, V et al., "Fluorescence imaging with near-infrared light: new technological advances that enable in vivo molecular imaging," Eur. Radiol., 13:195-208 (2003).

Onthank, D C et al., "90Y and 111In complexes of a DOTA-conjugated integrin $\alpha_v\beta_3$ receptor antagonist: different but biologically equivalent," Bioconjug. Chem., 15(2):235-241 (2004).

Park, K et al., "Antiangiogenic effect of bile acid acylated heparin derivative," Pharm. Res., 24(1):176-85 (2007).

Parsons, D W et al., "An integrated genomic analysis of human glioblastoma multiforme," Science, 321:1807-12 (2008).

Pasqualini, R et al., "Alpha v integrins as receptors for tumor targeting by circulating ligands," Nat. Biotechnol., 15(6): 542-546 (1997).

Pierschbacher, M D and E Ruoslahti, "Cell attachment activity of fibronectin can be duplicated by small synthetic fragments of the molecule," Nature, 309:30-33 (1984).

Rao, J, et al., "A trivalent system from vancomycin. D-ala-D-Ala with higher affinity than avidin.biotin," Science, 280(5364):708-11 (1998).

Ruoslahti, E and MD Pierschbacher, "Arg-Gly-Asp: a versatile cell recognition signal," Cell, 44(4):517-518 (1986).

Ryckaert, J et al., "Numerical integration of the cartesian equations of motion of a system with constraints: molecular dynamics of n-alkanes," J. Comput. Phys., 23(3):327-341 (1977).

Schnitzer, J E, "Vascular Targeting as a Strategy for Cancer Therapy," New. Engl. J. Med, 339:472-474 (1998).

Schottelius, M et al., "Ligands for mapping (alpha)v(beta) 3-integrin expression in vivo," Acc. Chem. Res., 42(7): 969-80 (2009).

Sevick-Muraca, E M et al., "Fluorescence-enhanced, near infrared diagnostic imaging with contrast agents," Curr. Opin. Chem. Biol., 6:642-50 (2002).

Shi, J et al., "Improving tumor uptake and excretion kinetics of $^{99m}$Tc-labeled cyclic arginine-glycine-aspartic (RGD) dimers with triglycine linkers," J. Med. Chem., 51(24): 7980-90 (2008).

Sivolapenko, G B et al., "Imaging of metastatic melanoma utilizing a technetium-99m labeled RGD-containing synthetic peptide," Eur. J. Nucl. Med., 25:1383-1389 (1998).

Smolarczyk, R et al., "Antitumor effect of RGD-4C-GG-D (KLAKLAK)2 peptide in mouse B16(F10) melanoma model," Acta Biochim. Pol., 53(4):801-5 (2006).

Takagi, J and Springer, T A, "Integrin activation and structural rearrangement," Immunol. Rev., 186:141-163 (2002).

DEVELOPMENT CORE TEAM "R: a language and environment for statistical computing," VIENNA AUSTRIA, R Foundation for Statistical Computing (2012).

van Hagen, P M et al., "Evaluation of a radiolabelled cyclic DTPA-RGD analogue for tumour imaging and radionuclide therapy," Int. J. Cancer, 90(4):186-198 (2000).

Wang, J et al., "Development and testing of a general amber force field," J. Comput. Chem., 25(9):1157-74 (2004).

Wickham, T J et al., "Integrins alpha v beta 3 and alpha v beta 5 promote adenovirus internalization but not virus attachment," Cell, 73:309-319 (1993).

Wu, Y et al., "MicroPET imaging of glioma integrin $\alpha v\beta 3$ expression using 64Cu-labeled tetrameric RGD peptide," J. Nucl. Med., 46(10):1707-1718 (2005).

Xie, J et al., "Tumor angiogenic endothelial cell targeting by a novel integrin-targeted nanoparticle," Int. J. Nanomedicine, 2:479-85 (2007).

Xiong, J-P et al., "Crystal structure of the extracellular segment of integrin $\alpha V\beta 3$ in complex with an Arg-Gly-Asp Ligand," Science, 296(5565):151-155 (2002).

All of the compositions and methods disclosed and claimed herein can be made and executed without undue experimentation in light of the present disclosure. While the compositions and methods of this invention have been described in terms of exemplary embodiments, it will be apparent to those of skill in the art that variations may be applied to the composition, methods and in the steps or in the sequence of steps of the method described herein without departing from the concept, spirit and scope of the invention. More specifically, it will be apparent that certain agents that are both chemically- and physiologically-related may be substituted for the agents described herein while the same or similar results would be achieved. All such similar substitutes and modifications apparent to those of ordinary skill in the art are deemed to be within the spirit, scope and concept of the invention as defined by the appended claims. Accordingly, the exclusive rights sought to be patented are as described in the claims below.

What is claimed is:

1. A bifunctional compound comprising a first bivalent integrin $\alpha_v\beta_3$ antagonist moiety having the formula:

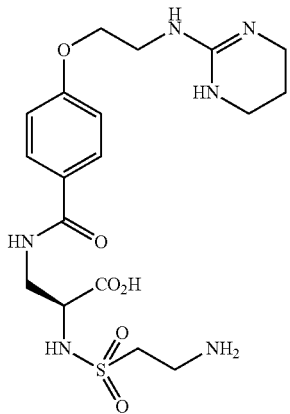

IA-1

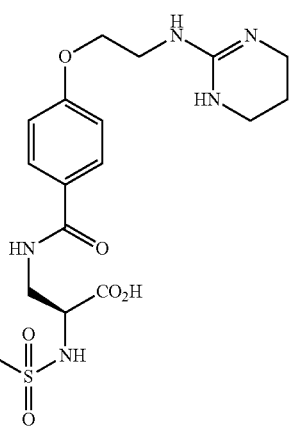

IA-C3 (n = 1); IA-C4 (n = 2); IA-C5 (n = 6)

and

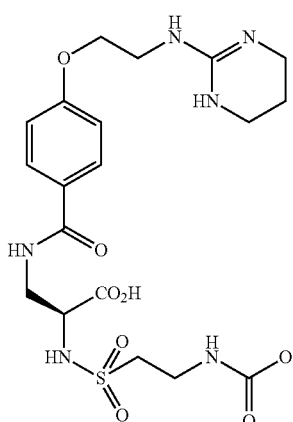

IA-C2

-continued

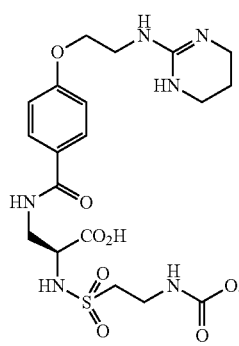 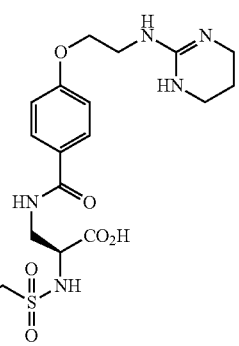

IA-C6 (n = 1); IA-C7 (n = 2); IA-C8 (n = 6)

operably linked via a linker moiety comprising 2-aminooctanedioic acid to a) an $^{18}$F-radiolabelled detection agent, and b) a therapeutic agent that comprises doxorubicin.

2. A kit comprising:
(a) the bifunctional compound of claim 1, formulated in a pharmaceutically-acceptable diluent or buffer, or in a vehicle comprising a population of nanoparticles; and
(b) instructions for administering the formulation to a mammal in need thereof.

3. The kit of claim 2, wherein the population of nanoparticles comprises one or more polymerized liposomes.

4. A composition comprising the bifunctional compound of claim 1, and a pharmaceutically-acceptable diluent, buffer, or vehicle.

5. The composition of claim 4, further comprising a population of nanoparticles.

6. The kit of claim 2, or the composition of claim 4, further comprising a compound selected from the group consisting of a nanoparticle, a microparticle, a nanocapsule, a microbubble, a microcapsule, a nanosphere, a microsphere, a surfactant, a neutral lipid, a lipid complex formed from at least two lipids, a liposome, a niosome, an ethosome, a transferosome, a phospholipid, a sphingosome, and any combination thereof.

7. The kit of claim 2, or the composition of claim 4, wherein the therapeutic agent comprises doxorubicin and at least one compound selected from the group consisting of an immunomodulating agent, a neuroactive agent, an anti-inflammatory agent, an anti-lipidemic agent, a hormone, a hormone receptor, a receptor agonist, a receptor antagonist, an anti-infective agent, a protein, a peptide, an antibody, an enzyme, an RNA, a DNA, an siRNA, an mRNA, an RNAi, a ribozyme, a cofactor, a steroid, an antisense oligonucleotide, and any combination thereof.

8. The kit of claim 2, or the composition of claim 4, further comprising a detection agent, an imaging agent, a contrast agent, a gas, and any combination thereof.

9. The kit of claim 2, or the composition of claim 4, further comprising a compound selected from the group consisting of a neutral lipid, a cephalin, a ceramide, a cerebroside, a cholesterol, a diacylglycerol, a diacylphosphatidylcholine, a diacylphosphatidyl ethanolamine, a phosphatidylcholine, a phosphatidylethanolamine, a sphingolipid, a sphingomyelin, a tetraether lipid, and any combination thereof.

\* \* \* \* \*